(12) United States Patent
Parikh

(10) Patent No.: US 8,492,518 B2
(45) Date of Patent: Jul. 23, 2013

(54) MUCIN HYPERSECRETION INHIBITORS AND METHODS OF USE

(75) Inventor: Indu Parikh, Chapel Hill, NC (US)

(73) Assignee: Biomarck Pharmaceuticals Ltd., Raleigh, NC (US)

( * ) Notice: Subject to any disclaimer, the term of this patent is extended or adjusted under 35 U.S.C. 154(b) by 365 days.

(21) Appl. No.: 12/430,662

(22) Filed: Apr. 27, 2009

(65) Prior Publication Data
US 2010/0197607 A1    Aug. 5, 2010

Related U.S. Application Data

(62) Division of application No. 11/335,564, filed on Jan. 20, 2006, now Pat. No. 7,524,926.

(60) Provisional application No. 60/645,293, filed on Jan. 20, 2005.

(51) Int. Cl.
C07K 7/06      (2006.01)

(52) U.S. Cl.
USPC ........................................ 530/329; 530/330

(58) Field of Classification Search
USPC ................................. 530/329, 330
See application file for complete search history.

(56) References Cited

U.S. PATENT DOCUMENTS

| | | | |
|---|---|---|---|
| 4,753,945 A | 6/1988 | Gilbard et al. | |
| 4,873,346 A | 10/1989 | Anderson | |
| 5,292,498 A | 3/1994 | Boucher | |
| 5,298,506 A | 3/1994 | Stamler et al. | |
| 5,436,243 A | 7/1995 | Sachs et al. | |
| 5,849,706 A | 12/1998 | Molina y Vedia et al. | |
| 5,849,719 A | 12/1998 | Carson et al. | |
| 5,858,784 A | 1/1999 | Debs et al. | |
| 5,858,981 A | 1/1999 | Schreiber et al. | |
| 5,861,502 A | 1/1999 | Prockop et al. | |
| 6,245,320 B1 | 6/2001 | Kim | |
| 6,407,058 B1 | 6/2002 | Staddon et al. | |
| 6,506,779 B1 | 1/2003 | Cheng et al. | |
| 7,265,088 B1 | 9/2007 | Li et al. | |
| 7,524,926 B2 | 4/2009 | Parikh | |
| 7,919,469 B2 | 4/2011 | Li et al. | |
| 2001/0033827 A1 | 10/2001 | Kim | |
| 2003/0013652 A1 | 1/2003 | Martin et al. | |
| 2004/0180836 A1 | 9/2004 | Martin et al. | |
| 2006/0040301 A1 | 2/2006 | Deirmengian | |
| 2006/0153834 A1* | 7/2006 | Carbonell et al. | 424/133.1 |
| 2006/0205664 A1 | 9/2006 | Parikh | |
| 2006/0217307 A1 | 9/2006 | Takashi et al. | |
| 2008/0020031 A1 | 1/2008 | Li et al. | |
| 2009/0275520 A1 | 11/2009 | Parikh | |

FOREIGN PATENT DOCUMENTS

| | | |
|---|---|---|
| AU | 766800 | 10/2003 |
| EP | 0 551 200 A1 | 7/1993 |
| EP | 1 154 786 | 8/2000 |
| EP | 1 538 162 A2 | 6/2005 |
| EP | 1 538 162 A3 | 6/2005 |
| WO | WO 93/00353 A1 | 1/1993 |
| WO | WO 95/27496 A1 | 10/1995 |
| WO | WO 96/18103 A1 | 6/1996 |
| WO | WO 00/50062 A2 | 8/2000 |
| WO | WO 01/20998 A1 | 3/2001 |
| WO | WO 03/000027 A2 | 1/2003 |
| WO | WO 03/000027 A3 | 5/2003 |
| WO | WO 2006/078899 A2 | 7/2006 |
| WO | WO 2006/078899 A3 | 12/2006 |
| WO | WO 2007/103368 A2 | 9/2007 |

OTHER PUBLICATIONS

Battersby (J. Am. Chem. Soc. 122, 2138-39, 2000).*
Abstract of JP 2004-049133, Feb. 2004.*
Lukton, Office Action, 3 pages, U.S. Appl. No. 12/430,624, United States Patent and Trademark Office (Jun. 2, 2011).
Graff et al., "Myristoylated and Nonmyristoylated Forms of a Protein Are Phosphorylated by Protein Kinase C," Science 246(4929):503-506 (1989).
Predel et al., "Isolation and structural elucidation of eight kinins from the retrocerebral complex of the American Cockroach, *Periplaneta americana*," Regulatory Peptides: 71(3):199-205 (1997).
Brinckerhoff et al., "Terminal Modifications Inhibit Proteolytic Degradation of an Immunogenic Mart-$1_{27\text{-}35}$ Peptide: Implications for Peptide Vaccines," Int. J. Canc. 83(3):326-334 (1999).
European Search Report, EP Appl. No. 11171749.2, 11 pages (Mar. 16, 2012).
Abdullah et al., "P2u purinoceptor regulation of mucin secretion in SPOC1 cells, a goblet cell line from the airways," Biochem. J. vol. 316, 1996, pp. 943-951.
Abdullah et al., "Protein kinase C and Ca2+ activation of mucin secretion in airway goblet cells," Am. Physiol. Soc. 273:L201-L210 (1997).
Aderem, "The MARCKS family of protein kinase-C substrates," Biochem. Soc. Trans. 23:587-591 (1995).
Adler et al., "Effects of inflammatory mediators and drugs on mucus secretion and mucociliary function," Res. Immunol. 149(3):245-248 (1998).
Adler et al., "Hypersecretion of Mucin in Response to inflammatory Mediators by Guinea Piog Tracheal Epithelial Cells In Vitro is Blocked by Inhibition of Nitric Oxide Synthase," Am. J. Respir. Cell Mol. Biol. 13:526-530 (1995).
Adler et al., "Myristoylated alanine-rich C-kinase substrate protein: A major intracellular regulatory molecule controlling secretion of mucin by human airway goblet cells," Chest 117(5 suppl. 1):266S-267S (2000).

(Continued)

*Primary Examiner* — David Lukton
(74) *Attorney, Agent, or Firm* — Cooley LLP

(57) ABSTRACT

Peptides are provided that comprise less than 24 amino acids. The peptides have an amino acid sequence selected from the group consisting of: (a) an amino acid sequence having from 4 to 6 contiguous amino acids of a reference sequence PEPTIDE 1; (b) an amino acid sequence substantially identical to the sequence defined in (a); and (c) a variant of the amino acid sequence defined in (a). Also provided is a non-myristoylated MANS peptide. Various methods of using the peptides are also provided.

18 Claims, No Drawings

OTHER PUBLICATIONS

Aigner et al., "Depletion of 43-kD growth associated protein in primary sensory neurons leads to diminished formation and spreading of growth cones," J. Cell Biol. 123(2):417-429 (1993).

Aragona et al., "Effects of a stable analogue pf PGE2 (11-deoxy-13, 14-didehydro-16 (S)-Methylester Methyl PGE2: FCE20700) on the secretory processes of conjunctival goblet cells of rabbit," Exp. Eye Res. 45(5):647-654 (1987).

Barnes, P.J., "Current and future therapies for airway mucus hypersecretion," Novartis Found Symp. 248:237-253 (2002).

Blackshear et al., "The MARCKS family of cellular protein kinase C substrates," J. Biol. Chem. 268(3):1501-1504 (1993).

Bouffard et al., National Center for Biotechnology Information Database, Accession No. G20124. Sep. 28, 1998.

Calle et al., "Glucose-induced phosphorylation of mytistoylated alanine-rich C kinase substrate (MARCKS) in isolated rat pancreatic islets," J. Biol. Chem. 267(26):18723-18727 (1992).

Coffey et al., "Glutamate exocytosis and MARCKS phosphorylation are enhanced by a metabotropic glutamate receptor coupled to a protein kinase C synergistically activated by diacylglycerol and arachidonic acid," J. Neurochem. 63(4):1303-1310 (1994).

Cross et al., "Antioxidant Protection: A Function of Tracheobronchial and Gastrointestinal Mucus," The Lancet, Jun. 16, 1984, pp. 1328-1329.

Dizier et al., "Genome screen for asthma and related phenotypes in the French EGEA study," American Journal Respiratory and Critical Care Medicine 162:1812-1818 (2000).

Dray-Charier et al., "Regulation of mucin secretion in human gallbladder epithelial cells: Predominant role of calcium and protein kinase C," Gastroenterology 112(3):978-990 (1997).

Driot et al., "Beneficial effects of a retinoic acid analog, CBS-211 A, on an experimental model of keraoconjunctivitis Sicca.," Invest Opthalmol. Vis. Sci. 33(1):190-195 (1992).

Elzagallaai, A., et al. "Platelet Secretion Induced by Phorbol Esters Stimulation is Mediated Though Phosphorylation of MARCKS: a MARCKS-Derived Peptide Blocks MARCKS Phosphorylation and Serotonin Release without Affecting Pleckstrin Phosphotylation," Hemostatis, Thrombosis, and Vascular Biology. 95(3):894-902. (Feb. 1, 2000).

European Search Report for application No. 02756467.3 dated Sep. 3, 2004.

Fischer et al., "Tumor Necrosis Factor-α Stimulates Mucin Secretion and Cyclic GMP Production by Guinea Pig Tracheal Epithelial Cells In Vitro," Am. J. Respir. Cell Mol. Biol.. vol. 20. 1999, pp. 413-422.

Garcher et al., "CA 19-9 ELISA test. A new method for studying mucus changes in tears," Br. J. Ophthalmol. 82(1):88-90 (1998).

Gipson et al., "Cellular origin of mucins of the ocular surface tear film," Adv. Exp. Med. Biol. 438:221-227 (1998).

Graff et al., "Protein Kinase C Substrate and Inhibitor Characteristics of Peptides Derived from the Myristoylated Alanine-rich C Kinase Substrate (MARCKS) Protein Phosphorylation Site Domain," J. Biol. Chem. 266(22):14390-14398 (1991).

Harlan et al., "The human myristoylated alanine-rich C kinase substrate (MARCKS) gene (MACS)," J. Biol. Chem. 266(22)14399-14405 (1991).

Huse, "Partial European Search Report," 4 pages, from European Patent application No. 04024019.4, European Patent Office, The Hague, The Netherlands (mailed May 3, 2005).

International Search Report corresponding to PCT/US02/22270 mailed on Jan. 22, 2003.

International Search Report corresponding to PCT/US07/05688 mailed on Feb. 24, 2009.

International Search Report for PCT/US03/21963; mailed Sep. 9, 2004.

International Search Report for PCT/US07/74514; mailed Jul. 14, 2008.

Kessler et al., "Stimulation of goblet cell mucous secretion by activation of nerves in rat conjunctiva," Curr. Eye Res. 14(11):985-992 (1995).

Kim et al., "Airway goblet cell mucin: its structurestructureand regulation of secretion," Eur. Resp. J. 10(11):2644-2649 (1997).

Kim et al., "Airway Mucus," Eur. Respir. J. vol. 10, 1997, p. 1438.

King et al., "Alteration of Airway Reactivity by Mucus, Respiration Physiology," vol. 62, 1985, pp. 47-59.

Ko et al., "ATP-induced mucin release from cultured airway goblet cells involves, in part, activation of protein kinase C," Am. J. Resp. Cell Mol. Biol. 16:194-198 (1997).

Krunkosky et al., "Effects of TNFα on Expression of ICAM-1 in Human Airway Epithelial Cells In Vitro," Am. J. Respir. Cell Mol. Biol., vol. 22, 2000, pp. 685-692.

Larivee et al., "Platelet-Activating Factor Induces Airway Mucin Release via Activation of Protein Kinase C: Evidence of Translocation of Protein Kinase C to Membranes," Am. J. Respir. Cell Mol. Biol., vol. 11 ,1994, pp. 194-205.

Lethem et al., "Nucleotide Regulation of Goblet Cells in Human Airway Epithelial Explants: Normal Exocytosis in Cystic Fibrosis," Am. J. Respir. Cell Mol. Biol., vol. 9, 1993, pp. 315-322.

Li, Y., et al., "MARCKS Protein is a Key Molecule Regulation Mucin Secretion by Human Airway Epithelial Cells in Vitro," The Journal of Biological Chemistry. 276(44):40982-40990. (Nov. 2, 2001).

Linsen et al., "Physiology of the lacrimal system," Bull. Soc. Belge. Ophtalmol. 238:35-44 (1990).

Liu et al., "Arginine vasopressin (AVP) causes the reversible phosphorylation of the myristoylated alanine-rich C kinase substrate (MARCKS) protein in the ovine anterior pituitary: evidence that MARCKS phosphorylation is associated with adrenocorticotropin (ACTH) secretion," Mol. Cell. Endocrinol. 105:217-226 (1994).

Liu et al., "Arginine vasopressin (AVP) causes the reversible phosphorylation of the myristoylated alanine-rich C kinase substrate (MARCKS) protein in the ovine anterior pituitary: evidence that MARCKS phosphorylation is associated with adrenocorticotropin (ACTH) secretion." Mol. Cell. Endocrinol. 101:247-256 (1994).

Lu et al., "Regulation of angiotensin II-induced neuromodulation by MARCKS in brain neurons," J. Cell Biol. 142(1):217-227(1998).

Mastropasqua et al., "Tear deficiency in Fuchs' intermediate uveitis," Can. J. Ophthalmol. 31(1):18-20 (1996).

Murray et al., National Center for Biotechnology Information Database, Accession No. G08525. Feb. 5, 1997.

Murray et al., National Center for Biotechnology Information Database, Accession No. G08539. Feb. 5, 1997.

Myat et al., "Identification of the basolateral targeting determinant of a peripheral membrane protein, MacMARCKS, in polarized cells," Current Biology 8(12):677-683 (1998).

Nakamura et al., "Mucin-like glycoprotein secretion is mediated by cyclic-AMP and protein kinase C signal transduction pathways in rat corneal epithelium," Exp. Eye Res. 66(5):513-519 (1998).

Nichols et al., "Demonstration of the mucous layer of the tear film by electron microscopy," Invest. Ophthahnol. Vis. Sci. 26(4):464-473 (1985).

Prescott et al, "Chronic Mucus Hypersecretion in COPD and Death From Pulmonary Infection," Eur. Respir. J., vol. 8, 1995, pp. 1333-1338.

Ralph, "Conjunctival goblet cell density in normal subjects and in dry eye syndromes," Invest. Ophthalnol. Vis. Sci. 14(4):299-302 (1975).

Raufman et al., "Expression and phosphorylation of a MARCKS-Like Protein in Gastric Chief Cells: Further evidence for modulation of pepsinogen secretion by interaction of $CA^{2+}$/Calmodulin with protein kinase C," J. Cell. Biochem. 64:514-523 (1997).

Rogers, "Mucus hypersecretion in chronic obstructive pulmonary disease. Chronic Obstructive Pulmonary Disease: Pathogenesis to Treatment," Novartis Foundation. Symposium 234. vol. 234. (2001).

Rogers, D.F. "Airway Goblet Cell Hyperplasia in Asthma: Hypersecretory and Anti-Inflammatory?" Clinical and Experimental Allergy. Editorial 32: 1124-1127 (2002).

Rogers, D.F., "Pulmonary mucus: Pediatric Perspective," Pediatric Pulmonology 36:178-188 (2003).

Shellans et al., "Conjunctival goblet cell response to vasoconstrictor use," J. Ocul. Pharmacol. 5(3):217-220 (1989).

Singer et al., "A MARCKS-related peptide blocks mucus hypersecretion in a moue model of asthma," Nat. Med. 10:193-196 (2004).

Steiger et al., "Concurrent Increases in the Storage and Release of Mucin-like Molecules by Rat Airway Epithelial Cells in Response to Bacterial Endotoxin," Am. J. Respir. Cell Mol. Biol., vol. 12, 1995, pp. 307-314.

Stein, "International Search Report," 5 pages, from international patent application PCT/US00/05050, European Patent Office, Rijswijk, The Netherlands (mailed Sep. 9, 2000).

Stormshak et al., "Dynamics of molecular mechanisms underlying ovarian oxytocin secretion," J. Reprod. Fertil. Suppl. 49:379-390 (1995).

Stumpo et al., "Molecular cloning, characterization, and expression of a cDNA encoding the '80-87-kDA' myristoylated alanine-rich C kinase substrate: A major cellular substrate for protein kinase C," Proc. Natl. Acad. Sci. USA 86:4012-4016 (1989).

Thelen et al., "Regulation by phosphorylation of the reversible association of a myristoylated protein kinase C substrate with the plasma membrane," Nature 351:320-322 (1991).

Theles et al., "Tumor necrosis factor alpha modifies agonist-dependent responses in human neutrophils by inducing the synthesis and myristoylation of a specific protein kinase C substrate," Proc. Natl. Acad. Sci. USA 87(15):5603-5607 (1990).

Thornton et al., "Identifcation of Two Glycoforms of the MUC5B Mucin in Human Respiratory Mucus," The Journal of Biological Chemistry, vol. 272, No. 14, Apr. 4, 1997, pp. 9561-9566.

Tseng "Topical tretinoin treatment for severe dry-eye disorders," J. Am. Acad. Dermatol. 15(4 part 2):860-866 (1986).

Vergeres et al., "The myristoyl moiety of myristoylated alanine-rich C kinase substrate (MARCKS) and MARCKS-related protein is embedded in the membrane," J. Biol. Chem. 270(34)19879-19887 (1995).

Vishwanath et al., "Adherence of *Pseudomonas aeruginosa* to Human Tracheobronchial Mucin," Infection and Immunity, vol. 45, No. 1, Jul. 1984, pp. 197-202.

Ward, P.A. and Mulligan M.S., "Blocking of adhesion molecules in vivo as anti-inflammatory therapy." Ther. Immunol. 1(3):165-171 (1994).

Wjst et al., "A genome-wide search for linkage to asthma," Genomics 58:1-8, 1999.

Xu et al., "Genome-wide screen and identification of gene-gene interactions for asthma-susceptibility in three U.S. populations: Collaborative study on the genetics of asthma," American Journal of Human Genetics. 68:1437-1446 (2001).

Zhao, Y., et al. "Role of MARCKS in regulating endothelial cell proliferation." Am J Physiol Cell Physiol. 279:C1611-C1620. (2000).

* cited by examiner

MUCIN HYPERSECRETION INHIBITORS AND METHODS OF USE

CROSS-REFERENCE TO RELATED APPLICATION

This application is a divisional application under 37 C.F.R. §1.53(b) of patent application Ser. No. 11/335,564 filed Jan. 20, 2006, now U.S. Pat. No. 7,524,926, issued on Apr. 28, 2009, which claims benefit of Provisional Application No. 60/645,293, filed Jan. 20, 2005, all of which are herein incorporated in their entirety by reference.

BACKGROUND OF THE INVENTION

The invention generally relates to compositions comprising peptides and methods for their use.

FIELD OF THE INVENTION

Mucus is a biological liquid that is capable of forming gels. It is a mixture of components, including water and secretory products from a variety of cells. Mucins, also called mucus glycoproteins or epithelial glycoproteins, are a major component of mucus and are glycoconjugates characterized by numerous oligosaccharide side chains linked to a peptide core by N- and O-linkages. Hypersecretion of mucin (the glycoprotein component of mucus) occurs in several respiratory diseases including asthma, chronic bronchitis, and cystic fibrosis (CF), and is a risk factor for mortality in patients with these diseases.

In the airways, mucins are released onto the airway surface from goblet cells in the surface epithelium, and from mucus cells of submucosal glands. The total amount of surface liquid (mucus) in the airways is the result of the rate of mucus secretion in conjunction with the rate of clearance of mucus (by epithelial reabsorption, evaporation, ciliary transport, and cough transport), i.e., the result of a difference between the rate of mucus secretion and the rate of clearance of mucus. Under "normal" conditions, the rate of secretion and clearance of mucus are balanced so that only a thin surface layer of liquid covers the tracheobronchial tree. Mucus hypersecretion (if not accompanied by a concomitant increase in mucus clearance) results in a net increase in the amount of mucous relative to normal conditions and leads to accumulation of airway mucus, which can result in airflow obstruction and increased retention of inhaled particulate and microbial matter.

Hypersecretion of mucus contributes to the pathogenesis of a large number of airway inflammatory diseases in both humans and non-human animals. Increased mucus secretion is seen in chronic disease states such as asthma, chronic obstructive pulmonary disease (COPD) and chronic bronchitis; in genetic diseases such as cystic fibrosis; in allergic conditions (atopy, allergic inflammation); in bronchiectasis; and in a number of acute, infectious respiratory illnesses such as pneumonia, rhinitis, influenza, and the common cold.

Accompanying hypersecretion of mucus in many of these respiratory diseases is the increased presence of inflammatory cells in the airways. These cells contribute greatly to the pathology of these diseases via the tissue damage and destruction done by the inflammatory mediators released from these cells. One example of such destruction via this chronic inflammation occurs in cystic fibrosis patients where mediators released from neutrophils (i.e. myeloperoxidase) induce the desquamation of the airway epithelial tissue.

Mammalian airways are lined by a thin layer of mucus produced and secreted by airway epithelial (goblet) cells and submucosal glands. In diseases such as asthma, COPD, chronic bronchitis, and cystic fibrosis, hypersecretion of mucus is a common lesion. Excess mucus can contribute to obstruction, susceptibility to infection, and even to destruction of airway walls and contiguous tissues. The major components of mucus are mucin glycoproteins synthesized by secretory cells (i.e., goblet cells and mucus cells) and stored within cytoplasmic membrane-bound granules. Mucins are a family of glycoproteins secreted by the epithelial cells including those at the respiratory, gastrointestinal and female reproductive tracts. Mucins are responsible for the viscoelastic properties of mucus and at least eight mucin genes are known. See U.S. patent application Ser. No. 10/180,753 (Publication No. U.S. 2003/0013652). Mucociliary impairment caused by mucin hypersecretion and/or mucus cell hyperplasia leads to airway mucus plugging that promotes chronic infection, airflow obstruction and sometimes death. Many airway diseases such as chronic bronchitis, chronic obstructive pulmonary disease, bronchiectacis, asthma, cystic fibrosis and bacterial infections are characterized by mucin overproduction. See U.S. patent application Ser. No. 10/180,753 (Publication No. U.S. 2003/0013652). Upon appropriate stimulation, mucin granules are released via an exocytotic process in which the granules translocate to the cell periphery where the granule membranes fuse with the plasma membrane, allowing for luminal secretion of the contents.

Despite the obvious pathophysiological importance of this process, intracellular signaling mechanisms linking stimulation at the cell surface to mucin granule release have only recently been elucidated. See Li et al., *Journal of Biological Chemistry*, 276: 40982-40990 (2001). The myristoylated, alanine-rich C kinase substrate (MARCKS) protein is believed to be required for mucus secretion by human bronchial epithelial cells. It has been hypothesized that MARCKS binds, at different sites, to secretory granule membranes and to the actin cytoskeleton to serve as a physical link between the contractile cytoskeleton and mucin granules, and could have a role in guiding secretory granules to docking sites on the cell membrane. See Singer et al., "A MARCKS-related peptide blocks mucus hypersecretion in a mouse model of asthma", *Nature Medicine*, 10: 193-196 (2004). MANS peptide (myr-peptide 1) is a myristoylated N-terminal 24 amino acid sequence of a protein called the "Myristoylated Alanine Rich C-Kinase Substrate" which is normally abbreviated as MARCKS protein. A 0.24 amino-acid fragment of MARCKS, myristoylated N-terminal sequence (MANS) peptide, has been shown to inhibit mucin release in vitro and has also been shown to block mucus hypersecretion in a mouse model of asthma. See Li et al. and Singer et al., supra.

The importance of myristoylation to promote translocation of peptides across membranes through the lipid bilayer is known. A recent study demonstrated this importance by showing that non-myristoylated peptides do not get through the cell membrane as compared to myristoylated peptides. See A. Harishchandran et al., "Interaction of a Pseudosubstrate Peptide of Protein Kinase C and its Myristoylated Form with Lipid Vesicles . . . Only the Myristoylated Form Translocates into Lipid Bilayer," *Biochem. Biopys. Acta*, 1713: 73-82 (2005).

SUMMARY OF THE INVENTION

In one aspect, a peptide is provided that consists of less than 24 amino acids and has an amino acid sequence selected from the group consisting of: (a) an amino acid sequence having from 4 to 23 contiguous amino acids of a reference amino acid sequence defined as PEPTIDE 1, which is also known as the MANS peptide, and (b) an amino acid sequence substantially identical to the amino acid sequence defined in (a). One or more amino acids of the peptide are optionally independently chemically modified, and the peptide has a mucin-inhibiting effect when administered to a mammal in a mucin-inhibiting amount.

In another aspect, a peptide is provided that consists of less than 24 amino acids and has an amino acid sequence selected from the group consisting of (a) an amino acid sequence having from 4 to 23 contiguous amino acids of a reference amino acid sequence defined as PEPTIDE 1; and (b) an amino acid sequence substantially identical to the sequence defined in (a). The N-terminal and C-terminal amino acids of the peptide are optionally independently chemically modified. The peptide has a mucin-inhibiting effect when administered to a mammal in a mucin-inhibiting amount and has a greater mucin-inhibiting effect on a mammal than MANS peptide when administered at equal concentrations.

In a further aspect, a peptide is provided that consists of less than 24 amino acids and has an amino acid sequence selected from the group consisting of: (a) an amino acid sequence having from 4 to 23 contiguous amino acids of a reference amino acid sequence defined as PEPTIDE 1; and (b) an amino acid sequence substantially identical to the sequence defined in (a). The N-terminal and C-terminal amino acids of the peptide are optionally independently chemically modified. The peptide has greater aqueous solubility than MANS peptide and has a mucin-inhibiting effect when administered to a mammal in a mucin-inhibiting amount.

In yet another aspect, a method of inhibiting mucin hypersecretion in a mammal is provided. The method comprises administering to the mammal a mucin-inhibiting amount of a peptide that inhibits mucin secretion. The peptide consists of less than 24 amino acids and has an amino acid sequence selected from the group consisting of: (a) an amino acid sequence having from 4 to 23 contiguous amino acids of a reference amino acid sequence defined as PEPTIDE 1; and (b) an amino acid sequence substantially identical to the sequence defined in (a). One or more amino acids of the peptide are optionally independently chemically modified.

In a further aspect, a method of inhibiting mucin hypersecretion in a mammal is provided. The method comprises administering to the mammal a mucin-inhibiting amount of a peptide that inhibits mucin secretion. The peptide consists of less than 24 amino acids and has an amino acid sequence selected from the group consisting of: (a) an amino acid sequence having from 4 to 23 contiguous amino acids of a reference amino acid sequence defined as PEPTIDE 1; and (b) an amino acid sequence substantially identical to the sequence defined in (a). The N-terminal and C-terminal amino acids of the peptide are optionally independently chemically modified, and the peptide has a greater mucin-inhibiting effect on a mammal than MANS peptide when administered at equal concentrations.

In yet a further aspect, a method of inhibiting mucin hypersecretion in a mammal is provided. The method comprises administering to the mammal a mucin-inhibiting amount of a peptide that inhibits mucin secretion. The peptide consists of less than 24 amino acids and has an amino acid sequence selected from the group consisting of: (a) an amino acid sequence having from 4 to 23 contiguous amino acids of a reference amino acid sequence defined as PEPTIDE 1; and (b) an amino acid sequence substantially identical to the sequence defined in (a). The N-terminal and C-terminal amino acids of the peptide are optionally independently chemically modified, and the peptide has greater aqueous solubility than MANS peptide.

In another aspect, a peptide is provided that consists of less than 24 amino acids and has an amino acid sequence consisting of a variant of an amino acid sequence having from 4 to 23 contiguous amino acids of a reference amino acid sequence defined as PEPTIDE 1. The N-terminal and C-terminal amino acids of the peptide are optionally chemically modified. The peptide has a mucin-inhibiting effect when administered to a mammal in a mucin-inhibiting amount, has greater aqueous solubility than MANS peptide, and has a greater mucin-inhibiting effect on a mammal than MANS peptide when administered at equal concentrations.

The peptides of the current invention are useful to reduce mucin hypersecretion and/or inhibit (i.e., reduce to normal levels or to less than normal levels) mucin hypersecretion in the treatment of diseases and in the treatment of disease symptoms in which mucin hypersecretion is exhibited such as is seen in chronic disease states such as asthma, chronic obstructive pulmonary disease (COPD) and chronic bronchitis; in genetic diseases such as cystic fibrosis; in allergic conditions (atopy, allergic inflammation); in bronchiectasis; and in a number of acute, infectious respiratory illnesses such as pneumonia, rhinitis, influenza, and the common cold.

In a further embodiment, a peptide is provided that consists of a sequence selected from the group consisting of: (a) an amino acid sequence having the sequence, GAQFSKTAAKGEAAAERPGEAAVA (SEQ ID NO. 1); and (b) an amino acid sequence substantially identical to the sequence defined in (a); wherein the N-terminal amino acid of the peptide is not myristoylated and the C-terminal amino acid of the peptide is optionally independently chemically modified, the peptide having a mucin hypersecretion-inhibiting effect when administered to a mammal in a mucin hypersecretion-inhibiting amount. This peptide is useful for treating mucus hypersecretion in pulmonary diseases.

DETAILED DESCRIPTION OF THE PREFERRED EMBODIMENTS

The present invention relates to methods and compositions for various uses, including the inhibition of mucin hypersecretion (i.e., the inhibition of mucin release) and mucus production (sometimes referred to herein as inhibition of mucus secretion) in a mammal. Prior to describing this invention in further detail, however, the following terms will first be defined.

Definitions

"Mucin-inhibiting effect", "mucin-inhibiting activity", or "inhibiting mucin secretion" means a reduction in the amount of mucin secretion (i.e., mucin release), and does not necessarily mean the complete cessation of mucin secretion. Administration of a composition having a mucin-inhibiting effect results in decreased mucin secretion compared to that which would occur, or would be expected, in the absence of such composition. In one aspect, the amount of the decrease in mucin secretion may be from about 5% of the amount which is secreted or hypersecreted above normal levels to about 100% of the amount which is secreted or hypersecreted above normal levels of secretion. In another aspect, the amount of the decrease in mucin secretion may be from about 5% of the amount which is secreted or hypersecreted above normal levels (i.e., from about 5% of the amount secreted above normal levels) to an amount which is below normal level of secretion, such as to about 50% of the amount secreted at normal levels of secretion.

"Mucus-inhibiting effect", "mucus-inhibiting activity", or "inhibiting mucus production" means a reduction in the amount of mucus production, and does not necessarily mean the complete cessation of mucus production. Administration of a composition having a mucus-inhibiting effect results in decreased mucus production compared to that which would occur, or would be expected, in the absence of such composition.

"Mucin-inhibiting amount" of a composition is that amount that reduces or inhibits mucin secretion (i.e., mucin release) as compared to that which would occur in the absence of the composition, such as an amount which reduces mucin secretion from about 5% to about 100% of the amount of mucin which is hypersecreted above normal levels.

"Mucus-inhibiting amount" of a composition is that amount that reduces or inhibits mucus production as compared to that which would occur in the absence of the composition.

In the reference peptide, GAQFSKTAAKGEAAAER-PGEAAVA (SEQ ID NO. 1), at the N-terminal position of the reference peptide, G is at position 1; adjacent to G at position 1 is A at position 2; adjacent to A at position 2 is Q at position 3; adjacent to Q at position 3 is F at position 4; adjacent to F at position 4 is S at position 5; adjacent to S at position 5 is K at position 6; adjacent to K at position 6 is T at position 7; adjacent to T at position 7 is A at position 8; adjacent to A at position 8 is A at position 9; adjacent to A at position 9 is K at position 10; adjacent to K at position 10 is G at position 11; adjacent to G at position 11 is E at position 12; adjacent to E at position 12 is A at position 13; adjacent to A at position 13 is A at position 14; adjacent to A at position 14 is A at position 15; adjacent to A at position 15 is E at position 16; adjacent to E at position 16 is R at position 17; adjacent to R at position 17 is P at position 18; adjacent to P at position 18 is G at position 19; adjacent to G at position 19 is E at position 20; adjacent to E at position 20 is A at position 21; adjacent to A at position 21 is A at position 22; adjacent to A at position 22 is V at position 23; and adjacent to V at position 23 is A at position 24, wherein position 24 is the C-terminal position of the reference peptide.

A "variant" of a reference peptide or a variant of a 4 to 23 amino acid segment of a reference peptide is a peptide which has an amino acid sequence which differs from the amino acid sequence of the reference peptide or from the amino acid sequence of the segment of the reference peptide, respectively, in at least one amino acid position in the reference peptide or reference peptide segment amino acid sequence, respectively, but which retains mucin- or mucus-inhibiting activity, which activity is typically between 0.1 to 10 times the activity of the reference peptide or segment, respectively, preferably between 0.2 to 6 times the activity of the reference peptide or segment, respectively, more preferably between 0.3 to 5 times the activity of the reference peptide or segment, respectively. A "variant" of a reference amino acid sequence or a variant of a 4 to 23 amino acid segment of a reference amino acid sequence is an amino acid sequence that differs by at least one amino acid from the reference amino acid sequence or from the segment of the reference amino acid sequence, respectively, but has an amino acid sequence of a peptide that retains mucin- or mucus-inhibiting activity of the peptide or segment, respectively, encoded by the reference amino acid sequence, which activity is typically between 0.1 to 10 times the activity of the peptide or segment, respectively, of the reference sequence, preferably between 0.2 to 6 times the activity of the peptide or segment of the reference sequence, respectively, more preferably between 0.3 to 5 times the activity of the peptide or segment of the reference sequence, respectively. A substitution variant peptide or a substitution variant amino acid sequence may vary (i.e., differ) from a reference peptide or reference amino acid sequence by one or more amino acid substitutions in the reference amino acid sequence; a deletion variant peptide or a deletion variant amino acid sequence may vary (i.e., differ) from a reference peptide or reference amino acid sequence by one or more amino acid deletions in the reference amino acid sequence; and an addition variant peptide or an addition variant amino acid sequence may vary (i.e., differ) from a reference peptide sequence or reference amino acid sequence by one or more amino acid additions in the reference sequence. A variant peptide or variant amino acid sequence can result from a substitution of one or more amino acids (e.g., substitution of at least 1, 2, 3, 4, 5, 6, 7, or 8 amino acids) in a reference sequence, or can result from a deletion of one or more amino acids (e.g., deletion of at least 1, 2, 3, 4, 5, 6, 7, or 8 amino acids) in a reference sequence, or can result from an addition of one or more amino acids (e.g., addition of at least 1, 2, 3, 4, 5, 6, 7, or 8 amino acids) in a reference sequence, or a combination thereof in any order. A substitution variant 4 to 23 amino acid peptide segment or a substitution variant 4 to 23 amino acid segment sequence may vary (i.e., differ) from a reference 4 to 23 amino acid peptide segment or reference 4 to 23 amino acid segment sequence by one or more amino acid substitutions in the reference amino acid segment sequence; a deletion variant 4 to 23 amino acid peptide segment or a 4 to 22 amino acid deletion variant amino acid segment sequence may vary (i.e., differ) from a 5 to 23 reference peptide segment or a 5 to 23 amino acid reference amino acid segment sequence by one or more amino acid deletions in the reference amino acid segment sequence; and an 4 to 23 amino acid addition variant peptide or a 4 to 23 amino acid addition variant amino acid sequence may vary (i.e., differ) from a 4 to 22 amino acid reference peptide sequence or a 4 to 22 amino acid reference amino acid sequence by one or more amino acid additions in the reference sequence. A 4 to 23 amino acid variant peptide or a 4 to 23 amino acid variant amino acid sequence can result from a substitution of one or more amino acids (e.g., substitution of at least 1, 2, 3, 4, 5, 6, 7, 8 amino acids) in a 4 to 23 amino acid segment of a reference amino acid sequence, or can result from a deletion of one or more amino acids (e.g., deletion of at least 1, 2, 3, 4, 5, 6, 7, or 8 amino acids) in a respectively larger reference amino acid sequence, or can result from an addition of one or more amino acids (e.g., addition of at least 1, 2, 3, 4, 5, 6, 7, or 8 amino acids) in a respectively smaller reference amino acid sequence, or from a combination thereof. Preferably, a variant peptide or amino acid sequence varies from a reference peptide or from a segment of a reference peptide or from a reference amino acid sequence or from a segment of a reference amino acid sequence, respectively, by less than 10 amino acid substitutions, deletions, and/or additions; more preferably less than 8 amino acid substitutions, deletions, and/or additions; even more preferably less than 6 amino acid substitutions, deletions, and/or additions; and even more preferably less than 5 amino acid substitutions, deletions, and/or additions; and yet even more preferably less than 4 amino acid substitutions, deletions, and/or additions. Most preferably the variant amino acid sequence differs from a reference peptide or segment amino acid sequence by one or two or three amino acids.

"Sequence identity" means, with respect to amino acid sequences of two peptides, the number of positions with identical amino acids divided by the number of amino acids in the shorter of the two sequences.

"Substantially identical" means, with respect to comparison of the amino acid sequences of two peptides or comparison of the amino acid sequences of two peptide segments (e.g. segments of a reference peptide amino acid sequence), that the amino acid sequence of the peptides or segments of peptides have at least 75% sequence identity, preferably at least 80% sequence identity, more preferably at least 90% sequence identity, and most preferably at least 95% sequence identity.

The term "peptide" as used herein includes the peptide as well as pharmaceutically acceptable salts of the peptide.

An "isolated" peptide, as used herein, means a naturally-occurring peptide that has been separated or substantially separated from the cellular components (e.g., nucleic acids and other peptides) that naturally accompany it by purification, recombinant synthesis, or chemical synthesis, and also encompasses non-naturally-occurring recombinantly or chemically synthesized peptides that have been purified or substantially purified from cellular components, biological materials, chemical precursors, or other chemicals.

The following three-letter and one-letter amino acid abbreviations are used throughout the text: Alanine: (Ala) A; Arginine: (Arg) R; Asparagine: (Asn) N; Aspartic acid: (Asp) D; Cysteine: (Cys) C; Glutamine: (Gln) Q; Glutamic acid: (Glu) E; Glycine: (Gly) G; Histidine: (His) H; Isoleucine: (Ile) I; Leucine: (Leu) L; Lysine: (Lys) K; Methionine: (Met) M; Phenylalanine: (Phe) F; Proline: (Pro) P; Serine: (Ser) S; Threonine: (Thr) T; Tryptophan: (Trp) W; Tyrosine: (Tyr) Y; Valine: (Val) V. Additional three letter symbols of amino acids useful herein include, in brackets, (Hyp) for hydroxyproline, (Nle) for norleucine, (Orn) for ornithine, (Pyr) for pyroglutamic acid and (Sar) for sarcosine. By convention, the amino (or N-terminal) end of a peptide appears at the left end of a written amino acid sequence of the peptide and the carboxy (or C-terminal) end appears at the right end of a written amino acid sequence. The amino acid sequence of a peptide can be written in single letter symbols to represent the amino acids which are covalently linked by peptide amide bonds in the peptide.

Table IX contains a list of amino acid sequences in single letter abbreviation format together with a respectively corresponding peptide number and SEQ ID NO. The reference peptide amino acid sequence is listed as peptide 1. Amino acid sequences of peptides of the invention having an amino acid sequence of from 4 to 23 contiguous amino acids of the reference amino acid sequence are listed in as peptides 2 to 231, together with the amino acid sequence of a random N-terminal sequence (RNS) comprising amino acids of the MANS peptide as peptide 232. Amino acid sequences of representative variants of amino acid sequences of peptides of the invention as described herein are also listed as peptides 233 to 245 and 247 to 251. This variant peptides listed are not intended to be a limiting group of peptides, but are presented only to serve as representative examples of variant peptides of the invention. Also presented is a representative reverse amino acid sequence and a representative random amino acid sequence of peptide of the invention. The reverse and random amino acid sequences in the table are not intended to be representative of the invention.

An amino acid sequence of a peptide listed in Table IX can be chemically modified. For example, if an amino acid sequence of a peptide listed in Table IX is chemically modified at the N-terminal amine to form an amide with a carboxylic acid, the resulting peptide is sometimes referred to herein by a combination of an identifier for the carboxylic acid as a prefix linked by a hyphen to the peptide number. For example, with respect to peptide 79 as an example, an N-terminal myristoylated peptide 79 may sometimes be referred to herein as "myristoylated-peptide 79" or "myr-peptide 79"; an N-terminal acetylated peptide 79 may sometimes be referred to herein as "acetyl-peptide 79" or "Ac-peptide 79". A cyclic version of peptide 79 may be referred to as "cyclic-peptide 79" or "cyc-peptide 79". Also, for example, if an amino acid sequence of a peptide listed in Table IX is chemically modified at the C-terminal carboxylic group, for example by an amine such as ammonia to form a C-terminal amide, the resulting peptide is sometimes referred to herein by a combination of an identifier for the amine residue as a suffix linked by a hyphen to the peptide number. Thus, for example, a C-terminal amide of peptide 79 can be sometimes referred to as "peptide-$NH_2$". When the N-terminal amine of the peptide (e.g., peptide 79) is chemically modified by, for example, a myristoyl group and the C-terminal carboxylic group is chemically modified by, for example, an ammonia group to form an amide as above, the resulting peptide can be sometimes referred to, using both prefix and suffix notation, as "myr-peptide 79-$NH_2$".

The invention involves peptides having amino acid sequences comprising less than 24 amino acids with amino acid sequences related to the amino acid sequence of MANS peptide (i.e., the MANS peptide is myristoyl-PEPTIDE 1 and the reference 24-amino acid sequence of the MANS peptide is PEPTIDE 1). The peptides of the current invention consist of amino acid sequences containing less than 24 amino acids, and may consist of from 8 to 14, from 10 to 12, from 9 to 14, from 9 to 13, from 10 to 13, from 10 to 14, at least 9, at least 10, or the like amino acids. The peptides are typically straight chains, but may be cyclic peptides as well. In addition, the peptides may be isolated peptides.

With respect to PEPTIDE 1, the reference 24 amino acid sequence, a segment of 23 continuous amino acids of the reference amino acid sequence is sometimes referred to herein as a 23-mer. Analogously, a segment of 22 continuous amino acids of the reference sequence is sometimes referred to herein as a 22-mer; a 21 amino acid sequence as a 21-mer; a 20 amino acid sequence as a 20-mer; a 19 amino acid sequence as a 19-mer; an 18 amino acid sequence as an 18-mer; a 17 amino acid sequence as a 17-mer; a 16 amino acid sequence as a 16-mer; a 15 amino acid sequence as a 15-mer; a 14 amino acid sequence as a 14-mer; a 13 amino acid sequence as a 13-mer; a 12 amino acid sequence as a 12-mer; an 11 amino acid sequence as an 11-mer; a 10 amino acid sequence as a 10-mer; a 9 amino acid sequence as a 9-mer; an 8 amino acid sequence as an 8-mer; a 7 amino acid sequence as a 7-mer; a 6 amino acid sequence as a 6-mer; a 5 amino acid sequence as a 5-mer; and a 4 amino acid sequence as a 4-mer. In one aspect, any of these "4- to 23-mer" amino acid sequences, which are themselves peptides (sometimes herein denoted as $H_2N$-peptide-COOH), can be independently chemically modified, for example, by chemical modification, which chemical modification can be selected from the group consisting of (i) amide formation at the N-terminal amine group ($H_2N$-peptide-) such as with, for example, a C1 or preferably with a C2 (acetic acid) to C22 carboxylic acid; (ii) amide formation at the C-terminal carboxylic group (-peptide-COOH) such as with, for example, ammonia or with a C1 to C22 primary or secondary amine; and (iii) a combination of thereof.

The peptides have an amino acid sequence selected from the group consisting of (a) an amino acid sequence having from 4 to 23 contiguous amino acids of the reference sequence, PEPTIDE 1; (b) a sequence substantially similar to the amino acid sequence defined in (a); and (c) a variant of the amino acid sequence defined in (a), which variant is selected from the group consisting of a substitution variant, a deletion variant, an addition variant, and combinations thereof. In some embodiments, the peptides have an amino acid sequence selected from the group consisting of: (a) an amino acid sequence having from 8 to 14 contiguous amino acids of the reference sequence, PEPTIDE 1; (b) an amino acid sequence substantially identical to the sequence defined in (a); and (c) a variant of the amino acid sequence defined in (a), which variant is selected from the group consisting of a substitution variant, a deletion variant, an addition variant, and combinations thereof. In yet other embodiments, the peptides have an amino acid sequence selected from the group consisting of: (a) an amino acid sequence having from 10 to 12 contiguous amino acids of the reference sequence, PEPTIDE 1; (b) an amino acid sequence substantially identical to the sequence defined in (a); and (c) a variant of the amino acid sequence defined in (a), which variant is selected from the group consisting of a substitution variant, a deletion variant, an addition variant, and combinations thereof. In further embodiments, the peptides have an amino acid sequence having at least 9, at least 10, from 9 to 14, from 9 to 13, from 10 to 13, from 10 to 14, or the like contiguous amino acids of the reference sequence, PEPTIDE 1; an amino acid sequence substantially identical thereto; or a variant thereof, which variant is selected from the group consisting of a substitution variant, a deletion variant, an addition variant, and combinations thereof. As explained further below, one or more of the amino acids of the peptides (e.g., the N-terminal and/or C-terminal amino acids) may be optionally independently chemically modified; in some embodiments, one or more amino acids of a peptide will be chemically modified while in other embodiments none of the amino acids of the peptide will be chemically modified. In one aspect, preferred modification can occur at the amine ($H_2N$—) group of the N-terminal amino acid of the peptide or peptide segment (which amine group would form a peptide amide bond if present internally within a peptide sequence rather than at the N-terminal position). In another aspect, preferred modification can occur at the carboxy (—COOH) group of the C-terminal amino acid of the peptide or peptide segment (which carboxy group would form a peptide amide bond if present internally within a peptide sequence rather than at the C-terminal position). In another aspect, preferred modification can occur at both the N-terminal amine ($H_2N$—) group and at the C-terminal carboxylic (—COOH) group.

In some embodiments, the amino acid sequence of the peptide begins from the N-terminal amino acid of the reference sequence PEPTIDE 1. For example, the peptides may have an amino acid sequence selected from the group consisting of (a) an amino acid sequence having from 4 to 23 contiguous amino acids of the reference sequence PEPTIDE 1, wherein the amino acid sequence begins from the N-terminal amino acid of the reference sequence (i.e., PEPTIDE 2, PEPTIDE 4, PEPTIDE 7, PEPTIDE 11, PEPTIDE 16, PEPTIDE 22, PEPTIDE 29, PEPTIDE 37, PEPTIDE 46, PEPTIDE 56, PEPTIDE 67, PEPTIDE 79, PEPTIDE 92, PEPTIDE 106, PEPTIDE 121, PEPTIDE 137, PEPTIDE 154, PEPTIDE 172, PEPTIDE 191, or PEPTIDE 211); (b) a sequence substantially similar to the amino acid sequence defined in (a); and (c) a variant of the amino acid sequence defined in (a).

In other embodiments, the amino acid sequence of the peptide ends at the C-terminal amino acid of the reference sequence PEPTIDE 1. For example, the peptides may have an amino acid sequence selected from the group consisting of (a) an amino acid sequence having from 4 to 23 contiguous amino acids of the reference sequence PEPTIDE 1, wherein the amino acid sequence ends at the C-terminal amino acid of the reference sequence (i.e., PEPTIDE 3, PEPTIDE 6, PEPTIDE 10, PEPTIDE 15, PEPTIDE 21, PEPTIDE 28, PEPTIDE 36, PEPTIDE 45, PEPTIDE 55, PEPTIDE 66, PEPTIDE 78, PEPTIDE 91, PEPTIDE 105, PEPTIDE 120, PEPTIDE 136, PEPTIDE 153, PEPTIDE 171, PEPTIDE 190, PEPTIDE 210, or PEPTIDE 231); (b) a sequence substantially similar to the amino acid sequence defined in (a); and (c) a variant of the amino acid sequence defined in (a).

In other embodiments, the amino acid sequence of the peptide does not begin at the N-terminal amino acid of the reference sequence PEPTIDE 1 but rather begins at the amino acid at position 2 through the amino acid at position 21 of the reference sequence PEPTIDE 1. For example, the peptides may have an amino acid sequence selected from the group consisting of (a) an amino acid sequence having from 4 to 23 contiguous amino acids of the reference sequence PEPTIDE 1, wherein the amino acid sequence begins at any amino acid between position 2 through position 21 of the reference sequence. These peptides may be between 4 and 23 contiguous amino acids long and may represent peptides in the middle of the reference sequence (PEPTIDE 1; (b) a sequence substantially similar to the amino acid sequence defined in (a); and (c) a variant of the amino acid sequence defined in (a). These peptides are disclose in Table IX.

Peptide amino acid sequences which are useful in the current invention to inhibit mucin hypersecretion in a mammal, and which are useful to reduce the amount of mucin hypersecretion in a mammal, and which are useful in the methods of inhibition of mucin hypersecretion and in the methods of reduction of mucin hypersecretion include amino acid sequences of isolated peptides and amino acid sequences of peptides which optionally contain N-terminal- and/or C-terminal-chemically modified groups of the current invention, which peptide amino acid sequences are selected from the group consisting of the 23-mers (i.e., peptides having a 23 amino acid sequence): PEPTIDE 2; and PEPTIDE 3; the 22-mers (i.e., peptides having a 22 amino acid sequence): PEPTIDE 4; PEPTIDE 5; and PEPTIDE 6; the 21-mers (i.e., peptides having a 21 amino acid sequence): PEPTIDE 7; PEPTIDE 8; PEPTIDE 9; and PEPTIDE 10; the 20-mers (i.e., peptides having a 20 amino acid sequence): PEPTIDE 11; PEPTIDE 12; PEPTIDE 13; PEPTIDE 14; and PEPTIDE 15; the 19-mers (i.e., peptides having a 19 amino acid sequence): PEPTIDE 16; PEPTIDE 17; PEPTIDE 18; PEPTIDE 19; PEPTIDE 20; and PEPTIDE 21; the 18-mers (i.e., peptides having a 18 amino acid sequence): PEPTIDE 22; PEPTIDE 23; peptide 25; peptide 26; peptide 27; and peptide 28; the 17-mers (i.e., peptides having a 17 amino acid sequence): peptide 29; peptide 30; peptide 31; peptide 32; peptide 33; peptide 34; peptide 35; and peptide 36; the 16-mers (i.e., peptides having a 16 amino acid sequence): peptide 37; peptide 38; peptide 39; peptide 40; peptide 41; peptide 42; peptide 43; peptide 44; and peptide 45; the 15-mers (i.e., peptides having a 15 amino acid sequence): peptide 46; peptide 47; peptide 48; peptide 49; peptide 50; peptide 51; peptide 52; peptide 53; peptide 54; and peptide 55; the 14-mers (i.e., peptides having a 14 amino acid sequence): peptide 56; peptide 57; peptide 58; peptide 59; peptide 60; peptide 61; peptide 62; peptide 63; peptide 64; peptide 65; and peptide 66; the 13-mers (i.e., peptides having a 13 amino acid sequence): peptide 67; peptide 68; peptide 69; peptide 70; peptide 71; peptide 72; peptide 73; peptide 74; peptide 75; peptide 76; peptide 77; and peptide 78; the 12-mers (i.e., peptides having a 12 amino acid sequence): peptide 79; peptide 80; peptide 81; peptide 82; peptide 83; peptide 84; peptide 85; peptide 86; peptide 87; peptide 88; peptide 89; peptide 90; and peptide 91; the 11-mers (i.e., peptides having a 11 amino acid sequence): peptide 92; peptide 93; peptide 94; peptide 95; peptide 96; peptide 97; peptide 98; peptide 99; peptide 100; peptide 101; peptide 102; peptide 103; peptide 104; and peptide 105; the 10-mers (i.e., peptides having a 10 amino acid sequence): peptide 106; peptide 107; peptide 108; peptide 109; peptide 110; peptide 111; peptide 112; peptide 113; peptide 114; peptide 115; peptide 116; peptide 117; peptide 118; peptide 119; and peptide 120; the 9-mers (i.e., peptides having a 9 amino acid sequence): peptide 121; peptide 122; peptide 123; peptide 124; peptide 125; peptide 126; peptide 127; peptide 128; peptide 129; peptide 130; peptide 131; peptide 132; peptide 133; peptide 134; peptide 135; and peptide 136; the 8-mers (i.e., peptides having a 8 amino acid sequence): peptide 137; peptide 138; peptide 139; peptide 140; peptide 141; peptide 142; peptide 143; peptide 144; peptide 145; peptide 146; peptide 147; peptide 148; peptide 149; peptide 150; peptide 151; peptide 152; and peptide 153; the 7-mers (i.e., peptides having a 7 amino acid sequence): peptide 154; peptide 155; peptide 156; peptide 157; peptide 158; peptide 159; peptide 160; peptide 161; peptide 162; peptide 163; peptide 164; peptide 165; peptide 166; peptide 167; peptide 168; peptide 169; peptide 170; and peptide 171; the 6-mers (i.e., peptides having a 6 amino acid sequence): peptide 172; peptide 173; peptide 174; peptide 175; peptide 176; peptide 177; peptide 178; peptide 179; peptide 180; peptide 181; peptide 182; peptide 183; peptide 184; peptide 185; peptide 186; peptide 187; peptide 188; peptide 189; and peptide 190; the 5-mers (i.e., peptides having a 5 amino acid sequence): peptide 191; peptide 192; peptide 193; peptide 194; peptide 195; peptide 196; peptide 197; peptide 198; peptide 199; peptide 200; peptide 201; peptide 202; peptide 203; peptide 204; peptide 205; peptide 206; peptide 207; peptide 208; peptide 209; and peptide 210; and the 4-mers (i.e., peptides having a 4 amino acid sequence): peptide 211; peptide 212; peptide 213; peptide 214; peptide 215; peptide 216; peptide 217; peptide 218; peptide 219; peptide 220; peptide 221; peptide 222; peptide 223; peptide 224; peptide 225; peptide 226; peptide 227; peptide 228; peptide 229; peptide 230; and peptide 231.

Preferred amino acid sequences of isolated peptides and of N-terminal- and/or C-terminal-chemically modified peptides of the current invention are selected from the group consisting of the 23-mers: PEPTIDE 2; and PEPTIDE 3; the 22-mers: PEPTIDE 4; PEPTIDE 5; and PEPTIDE 6; the 21-mers: PEPTIDE 7; PEPTIDE 8; PEPTIDE 9; and PEPTIDE 10; the 20-mers: PEPTIDE 11; PEPTIDE 12; PEPTIDE 13; PEPTIDE 14; and PEPTIDE 15; the 19-mers: PEPTIDE 16; PEPTIDE 17; PEPTIDE 18; PEPTIDE 19; PEPTIDE 20; and PEPTIDE 21; the 18-mers: PEPTIDE 22; PEPTIDE 23; peptide 24; peptide 25; peptide 26; peptide 27; and peptide 28; the 17-mers: peptide 29; peptide 30; peptide 31; peptide 32; peptide 33; peptide 34; peptide 35; and peptide 36; the 16-mers: peptide 37; peptide 38; peptide 39; peptide 40; peptide 41; peptide 42; peptide 43; peptide 44; and peptide 45; the 15-mers: peptide 46; peptide 47; peptide 48; peptide 49; peptide 50; peptide 51; peptide 52; peptide 53; and peptide 54; the 14-mers: peptide 56; peptide 57; peptide 58; peptide 59; peptide 60; peptide 61; peptide 62; peptide 63; and peptide 64; the 13-mers: peptide 67; peptide 68; peptide 69; peptide 70; peptide 71; peptide 72; peptide 73; peptide 74; and peptide 75; the 12-mers: peptide 79; peptide 80; peptide 81; peptide 82; peptide 83; peptide 84; peptide 85; peptide 86; and peptide 87; the 11-mers: peptide 92; peptide 93; peptide 94; peptide 95; peptide 96; peptide 97; peptide 98; peptide 99; and peptide 100; the 10-mers: peptide 106; peptide 107; peptide 108; peptide 109; peptide 110; peptide 111; peptide 112; peptide 113; and peptide 114; the 9-mers: peptide 122; peptide 123; peptide 124; peptide 125; peptide 126; peptide 127; peptide 128; and peptide 129; the 8-mers: peptide 139; peptide 140; peptide 141; peptide 142; peptide 143; peptide 144; and peptide 145; the 7-mers: peptide 157; peptide 158; peptide 159; peptide 160; peptide 161; and peptide 162; the 6-mers: peptide 176; peptide 177; peptide 178; peptide 179; and peptide 180; the 5-mers: peptide 196; peptide 197; peptide 198; and peptide 199; and the 4-mers: peptide 217; and peptide 219.

More preferred amino acid sequences of isolated peptides and of N-terminal- and/or C-terminal-chemically modified peptides of the current invention are selected from the group consisting of the 23-mers: peptide 2; and peptide 3; the 22-mers: peptide 4; peptide 5; and peptide 6; the 21-mers: peptide 7; peptide 8; peptide 9; and peptide 10; the 20-mers: peptide 11; peptide 12; peptide 13; peptide 14; and peptide 15; the 19-mers: peptide 16; peptide 17; peptide 18; peptide 19; peptide 20; and peptide 21; the 18-mers: peptide 22; peptide 23; peptide 24; peptide 25; peptide 26; peptide 27; and peptide 28; the 17-mers: peptide 29; peptide 30; peptide 31; peptide 32; peptide 33; peptide 34; peptide 35; and peptide 36; the 16-mers: peptide 37; peptide 38; peptide 39; peptide 40; peptide 41; peptide 42; peptide 43; peptide 44; and peptide 45; the 15-mers: peptide 46; peptide 47; peptide 48; peptide 49; peptide 50; peptide 51; peptide 52; peptide 53; and peptide 54; the 14-mers: peptide 56; peptide 57; peptide 58; peptide 59; peptide 60; peptide 61; peptide 62; peptide 63; and peptide 64; the 13-mers: peptide 67; peptide 68; peptide 69; peptide 70; peptide 71; peptide 72; peptide 73; peptide 74; peptide 80; peptide 81; peptide 82; peptide 83; peptide 84; peptide 85; peptide 86; and peptide 87; the 11-mers: peptide 92; peptide 93; peptide 94; peptide 95; peptide 96; peptide 97; peptide 98; peptide 99; and peptide 100; the 10-mers: peptide 106; peptide 108; peptide 109; peptide 110; peptide 111; peptide 112; peptide 113; and peptide 114; the 9-mers: peptide 124; peptide 125; peptide 126; peptide 127; peptide 128; and peptide 129; the 8-mers: peptide 141; peptide 142; peptide 143; peptide 144; and peptide 145; the 7-mers: peptide 159; peptide 160; peptide 161; and peptide 162; the 6-mers: peptide 178; peptide 179; and peptide 180; the 5-mers: peptide 198; and peptide 199; and the 4-mer: peptide 219.

In yet other embodiments, the amino acid sequence of the peptide includes the contiguous residues A, K, G, and E as in peptide 219 of the reference sequence PEPTIDE 1. For example, the peptides may have an amino acid sequence selected from the group consisting of (a) an amino acid sequence having from 4 to 23 contiguous amino acids of the reference sequence PEPTIDE 1, wherein the amino acid sequence of the peptide includes the contiguous residues A, K, G, and E as in peptide 219 of the reference peptide PEPTIDE 1 (e.g., PEPTIDE 219, PEPTIDE 45, PEPTIDE 79, PEPTIDE 67, PEPTIDE 80, etc.); (b) a sequence substantially similar to the amino acid sequence defined in (a); and (c) a variant of the amino acid sequence defined in (a).

Examples of peptide segments which contain the amino acid sequence AKGE of the reference peptide amino acid sequence, PEPTIDE 1, include (a) the 23-mers: peptide 2; and peptide 3; the 22-mers: peptide 4; peptide 5; and peptide 6; the 11-mers: peptide 7; peptide 8; peptide 9; and peptide 10; the 20-mers: peptide 11; peptide 12; peptide 13; peptide 14; and peptide 15; the 19-mers: peptide 16; peptide 17; peptide 18; peptide 19; peptide 20; and peptide 21; the 18-mers: peptide 22; peptide 23; peptide 24; peptide 25; peptide 26; peptide 27; and peptide 28; the 17-mers: peptide 29; peptide 30; peptide 31; peptide 32; peptide 33; peptide 34; peptide 35; and peptide 36; the 16-mers: peptide 37; peptide 38; peptide 39; peptide 40; peptide 41; peptide 42; peptide 43; peptide 44; and peptide 45; the 15-mers: peptide 46; peptide 47; peptide 48; peptide 49; peptide 50; peptide 51; peptide 52; peptide 53; and peptide 54; the 14-mers: peptide 56; peptide 57; peptide 58; peptide 59; peptide 60; peptide 61; peptide 62; peptide 63; and peptide 64; the 13-mers: peptide 67; peptide 68; peptide 69; peptide 70; peptide 71; peptide 72; peptide 73; peptide 74; and peptide 75; the 12-mers: peptide 79; peptide 80; peptide 81; peptide 82; peptide 83; peptide 84; peptide 85; peptide 86; and peptide 87; the 11-mers: peptide 93; peptide 94; peptide 95; peptide 96; peptide 97; peptide 98; peptide 99; and peptide 100; the 10-mers: peptide 108; peptide 109; peptide 110; peptide 111; peptide 112; peptide 113; and peptide 114; the 9-mers: peptide 124; peptide 125; peptide 126; peptide 127; peptide 128; and peptide 129; the 8-mers: peptide 141; peptide 142; peptide 143; peptide 144; and peptide 145; the 7-mers: peptide 159; peptide 160; peptide 161; and peptide 162; the 6-mers: peptide 178; peptide 179; and peptide 180; the 5-mers: peptide 198; and peptide 199; and the 4-mer: peptide 219, (b) a sequence substantially similar to the amino acid sequence defined in (a); and (c) a variant of the amino acid sequence defined in (a), which variant is selected from the group consisting of a substitution variant, a deletion variant, an addition variant, and combinations thereof, wherein the segment comprises or consists of from 4 to 23 contiguous amino acids.

In another embodiment, preferred peptide sequences have an amino acid sequence selected from the group consisting of (a) an amino acid sequence having from 10 to 23 contiguous amino acids of the reference sequence, peptide 1; (b) a sequence substantially similar to the amino acid sequence defined in (a); and (c) a variant of the amino acid sequence defined in (a), which variant is selected from the group consisting of a substitution variant, a deletion variant, an addition variant, and combinations thereof, wherein the preferred amino acid sequences comprise the 23-mer: peptide 2; the 22-mer: peptide 4; the 21-mer: peptide 7; the 20-mer: peptide 11; the 19-mer: peptide 16; the 18-mer: peptide 22; the 17-mer: peptide 29; the 16-mer: peptide 37; the 15-mer: peptide 46; the 14-mer: peptide 56; the 13-mer: peptide 67; the 12-mer: peptide 79; the 11-mer: peptide 92; and the 10-mer: peptide 106.

In further embodiments, the amino acid sequence of the peptide begins from the N-terminal amino acid of the reference sequence PEPTIDE 1 and includes the contiguous residues A, K, G, and E as in peptide 219 of the reference sequence PEPTIDE 1, while in other embodiments the amino acid sequence of the peptide ends at the C-terminal amino acid of the reference sequence PEPTIDE 1 and includes the contiguous residues A, K, G, and E as in peptide 219 of the reference sequence PEPTIDE 1.

The peptides may include one or more amino acid deletions, substitutions, and/or additions with respect to the reference amino acid sequence. Preferably, the substitutions may be conservative amino acid substitutions, or the substitutions may be non-conservative amino acid substitutions. In some embodiments, the peptides, including the peptides with amino acid sequences that are substantially identical to or variants of the reference amino acid sequence, will not have deletions or additions as compared to the corresponding contiguous amino acids of the reference amino acid sequence, but may have conservative or non-conservative substitutions. Amino acid substitutions that may be made to the reference amino acid sequence in the peptides of the invention include, but are not limited to, the following: alanine (A) may be substituted with lysine (K), valine (V), leucine (L), or isoleucine (I); glutamic acid (E) may be substituted with aspartic acid (D); glycine (G) may be substituted with proline (P); lysine (K) may be substituted with arginine (R), glutamine (Q), or asparagine (N); phenylalanine (F) may be substituted with leucine (L), valine (V), isoleucine (I), or alanine (A); proline (P) may be substituted with glycine (G); glutamine (Q) may be substituted with glutamic acid (E) or asparagine (N); arginine (R) may be substituted with lysine (K), glutamine (Q), or asparagine (N); serine (S) may be substituted with threonine; threonine (T) may be substituted with serine (S); and valine (V) may be substituted with leucine (L), isoleucine (I), methionine (M), phenylalanine (F), alanine (A), or norleucine (Nle). For example, substitutions that could be made to the reference amino acid sequence in the peptides of the invention include substituting alanine (A) for phenylalanine (F) (e.g., at amino acid position 4 of the reference amino acid sequence), glutamic acid (E) for glutamine (Q) (e.g., at amino acid position 3 of the reference amino acid sequence), lysine (K) for alanine (A) (e.g., at amino acid positions 2 and/or 8 of the reference amino acid sequence), and/or serine (S) for threonine (T) (e.g., at amino acid position 7 of the reference amino acid sequence).

When substitutions are included in the amino acid sequences of the peptides of the invention (which peptides comprise unmodified as well as peptides which are chemically modified for example by N-terminal and/or C-terminal modification such as by amide formation) with respect to the reference amino acid sequence, there is preferably at least 80% sequence identity between the amino acid sequence of the peptide and the reference amino acid sequence. Peptides having 5 to 23 amino acids and including one amino acid substitution with respect to the reference amino acid sequence will have between about 80% to about 96% (i.e., ~95.7%) sequence identity to the reference amino acid sequence. Peptides having 10 to 23 amino acids and including one amino acid substitution with respect to the reference amino acid sequence will have between about 90% to about 96% (i.e., ~95.7%) sequence identity to the reference amino acid sequence. Peptides having 20 to 23 amino acids and including one amino acid substitution with respect to the reference amino acid sequence will have between about 95% to about 96% (i.e., ~95.7%) sequence identity to the reference amino acid sequence. Peptides having 10 to 23 amino acids and including two amino acid substitutions with respect to the reference amino acid sequence will have between about 80% to about 92% (i.e., ~91.3%) sequence identity to the reference amino acid sequence. Peptides having 16 to 23 amino acids and including two amino acid substitutions with respect to the reference amino acid sequence will have between about 87.5% to about 92% (i.e., ~91.3%) sequence identity to the reference amino acid sequence. Peptides having 20 to 23 amino acids and including two amino acid substitutions with respect to the reference amino acid sequence will have between about 90% to about 92% (i.e., ~91.3%) sequence identity to the reference amino acid sequence. Peptides having 15 to 23 amino acids and including three amino acid substitutions with respect to the reference amino acid sequence will have between about 80% to about 87% sequence identity to the reference amino acid sequence. Peptides having 20 to 23 amino acids and including three amino acid substitutions with respect to the reference amino acid sequence will have between about 85% to about 87% sequence identity to the reference amino acid sequence. Peptides having 20 to 23 amino acids and including four amino acid substitutions with respect to the reference amino acid sequence will have between about 80% to about 83% (i.e., ~82.6%) sequence identity to the reference amino acid sequence.

In peptides of the current invention, with respect to the contiguous amino acid sequence of the reference peptide (which is a 24-mer) substitution of one amino acid in a contiguous 23 amino acid sequence (a 23-mer) selected from the reference 24 amino acid sequence provides a peptide with an amino acid sequence which has a 95.65% (or ~96%) sequence identity to the amino acid segment in the reference peptide with which the 23-mer has identity. Analogously, substitution of two, three, four, and five amino acids in said 23-mer provides a peptide with an amino acid sequence which has a 91.30% (or ~91%), 86.96% (or ~87%), 82.61% (or ~83%), and 78.27% (or ~78%) sequence identity, respectively, to the reference peptide amino acid sequence. Analogously, substitution of one, two, three, four, and five amino acids in a 22-mer provides a peptide with an amino acid sequence which has a 95.45% (or ~95%), 90.91% (or ~91%), 86.36% (or ~86%), 81.82% (or ~82%), and 77.27% (or ~77%) sequence identity, respectively, to the reference peptide amino acid sequence. Analogously, substitution of one, two, three, four, and five amino acids in a 21-mer provides a peptide with an amino acid sequence which has a 95.24% (~95%), 90.48 (~91%), 85.71% (~86%), 80.95 (~81%), and 76.19% (~76%) sequence identity, respectively, to the reference peptide amino acid sequence. Analogously, substitution of one, two, three, four, and five amino acids in a 20-mer provides a peptide with an amino acid sequence which has a 95.00% (95%), 90.00% (90%), 85.00% (85%), 80.00% (80%), and 75.00% (75%) sequence identity, respectively, to the reference peptide amino acid sequence. Analogously, substitution of one, two, three, and four amino acids in a 19-mer provides a peptide with an amino acid sequence which has a 94.74% (~95%), 89.47% (~89%), 84.21% (~84%), and 78.95% (~79%) sequence identity, respectively, to the reference peptide amino acid sequence. Analogously, substitution of one, two, three, and four amino acids in an 18-mer provides a peptide with an amino acid sequence which has a 94.44% (~94%), 88.89% (~89%), 83.33% (~83%), and 77.78% (~78%) sequence identity, respectively, to the reference peptide amino acid sequence. Analogously, substitution of one, two, three, and four amino acids in an 17-mer provides a peptide with an amino acid sequence which has a 94.12% (~94%), 88.23% (~88%), 82.35% (~82%), and 76.47% (~76%) sequence identity, respectively, to the reference peptide amino acid sequence. Analogously, substitution of one, two, three, and four amino acids in a 16-mer provides a peptide with an amino acid sequence which has a 93.75% (~94%), 87.50% (~88%), 81.25% (~81%), and 75.00% (75%) sequence identity, respectively, to the reference peptide amino acid sequence. Analogously, substitution of one, two, and three amino acids in a 15-mer provides a peptide with an amino acid sequence which has a 93.33% (~93%), 86.67% (~87%), and 80.00% (80%) sequence identity, respectively, to the reference peptide amino acid sequence. Analogously, substitution of one, two, and three amino acids in a 14-mer provides a peptide with an amino acid sequence which has a 92.86% (~93%), 85.71% (~86%), and 78.57% (79%) sequence identity, respectively, to the reference peptide amino acid sequence. Analogously, substitution of one, two, and three amino acids in a 13-mer provides a peptide with an amino acid sequence which has a 92.31% (~92%), 84.62% (~85%), and 76.92% (~77%) sequence identity, respectively, to the reference peptide amino acid sequence. Analogously, substitution of one, two, and three amino acids in a 12-mer provides a peptide with an amino acid sequence which has a 91.67% (~92%), 83.33% (~83%), and 75.00% (75%) sequence identity, respectively, to the reference peptide amino acid sequence. Analogously, substitution of one and two amino acids in an 11-mer provides a peptide with an amino acid sequence which has a 90.91% (~91%) and 81.82% (~82%) sequence identity, respectively, to the reference peptide amino acid sequence. Analogously, substitution of one and two amino acids in a 10-mer provides a peptide with an amino acid sequence which has a 90.00% (90%) and 80.00% (80%) sequence identity, respectively, to the reference peptide amino acid sequence. Analogously, substitution of one and two amino acids in a 9-mer provides a peptide with an amino acid sequence which has a 88.89% (~89%) and 77.78% (~78%) sequence identity, respectively, to the reference peptide amino acid sequence. Analogously, substitution of one and two amino acids in an 8-mer provides a peptide with an amino acid sequence which has a 87.50% (~88%) and 75.00% (75%) sequence identity, respectively, to the reference peptide amino acid sequence. Analogously, substitution of one amino acid in a 7-mer, 6-mer, 5-mer, and 4-mer provides a peptide with an amino acid sequence which has a 85.71% (~86%), 83.33% (~83.3%), 80.00% (80%), and 75.00% (75%) sequence identity, respectively, to the reference peptide. Preferred amino acid sequences of this invention have greater than 80% sequence identity to the amino acid sequence in the reference sequence, more preferably between 81% and 96% sequence identity to the amino acid sequence in the reference sequence, and more preferably between 80% and 96% sequence identity to the amino acid sequence in the reference sequence. The preferred amino acid sequences can be optionally N-terminally chemically bonded at the terminal peptide amino group to a $C_2$ to $C_{22}$ linear aliphatic carboxylic acid moiety, more preferably to a $C_2$ to $C_{16}$ linear aliphatic carboxylic acid moiety, most preferably to a $C_2$ or $C_{16}$ linear aliphatic carboxylic acid moiety, by an amide bond, and optionally C-terminally chemically bonded at the terminal peptide carboxylic group to an amine such as ammonia or a primary or secondary amine such as a C1 to C16 linear aliphatic primary amine, by an amide bond.

Examples of substitution variants of peptide 79, a 12-mer, include, for example, peptide 238, where Q at position 3 in peptide 79 has been substituted by E in sequence 238; peptide 233, where A at position 2 in peptide 79 has been substituted by K in peptide 233; peptide 234, where A at position 8 in peptide 79 has been substituted by K in peptide 234; peptide 235, where A at positions 2 and 8 in peptide 79 have been substituted by K in peptide 235; peptide 237, where F at position 4 in peptide 79 has been substituted by A in peptide 237; peptide 239, where K at position 10 in peptide 79 has been substituted by A in peptide 239; peptide 240, where G at position 11 in peptide 79 has been substituted by A in peptide 240; and peptide 241, where E at position 12 in peptide 79 has been substituted by A in peptide 241.

Examples of substitution variants of peptide 106, a 10-mer, include, for example, peptide 236, where F at position 4 in peptide 106 has been substituted by A in peptide 236; peptide 242, where G at position 1 in peptide 106 has been substituted by A in peptide 242; peptide 243, where Q at position 3 in peptide 106 has been substituted by A in peptide 243; peptide 244, where S at position 5 in peptide 106 has been substituted by A in peptide 244; peptide 245, where K at position 6 in peptide 106 has been substituted by A in peptide 245; peptide 247, where T at position 7 in peptide 106 has been substituted by A in peptide 247; peptide 248, where K at position 10 in peptide 106 has been substituted by A in peptide 248; peptide 249, where K at positions 6 and 10 in peptide 106 have both been substituted, each by A, in peptide 249.

Examples of a substitution variant of peptide 137, an 8-mer, include for example, peptide 250, where F at position 4 in peptide 137 has been substituted by A in peptide 250.

Examples of a substitution variant of peptide 219, a 4-mer, include for example, peptide 251, where K at position 2 in peptide 219 has been substituted by A in peptide 251.

A substitution variant peptide such as described herein can be in the form of an isolated peptide or in the form of a chemically modified peptide such as, for example, an N-terminal amide such as a myristoyl amide, an acetyl amide, and the like as described herein, and such as, for example, a C-terminal amide such as an amide formed with ammonia, and such as both an N-terminal amide and a C-terminal amide.

When deletions are included in the amino acid sequences of the peptides of the invention with respect to the reference amino acid sequence, there is preferably at least 80% sequence identity between the amino acid sequence of the peptide to the reference amino acid sequence. Peptides having 5 to 23 amino acids and including one amino acid deletion with respect to the reference peptide will have between 80% to about 96% (i.e., ~95.7%) sequence identity to the reference amino acid sequence. Peptides having 10 to 23 amino acids and including one amino acid deletion with respect to the reference peptide will have between about 90% to about 96% (i.e., ~95.7%) sequence identity to the reference amino acid sequence. Peptides having 20 to 23 amino acids and including one amino acid deletion with respect to the reference peptide will have between 95% to about 96% (i.e., ~95.7%) sequence identity to the reference amino acid sequence. Peptides having 10 to 23 amino acids and including two amino acid deletions with respect to the reference peptide will have between about 80% to about 92% (i.e., ~91.3%) sequence identity to the reference amino acid sequence. Peptides having 16 to 23 amino acids and including two amino acid deletions with respect to the reference peptide will have between about 87.5% to about 92% (i.e., ~91.3%) sequence identity to the reference amino acid sequence. Peptides having 20 to 23 amino acids and including two amino acid deletions with respect to the reference peptide will have between about 90% to about 92% (i.e., ~91.3%) sequence identity to the reference amino acid sequence. Peptides having 15 to 23 amino acids and including three amino acid deletions with respect to the reference peptide will have between about 80% to about 87% sequence identity to the reference amino acid sequence. Peptides having 20 to 23 amino acids and including three amino acid deletions with respect to the reference peptide will have between about 85% to about 87% sequence identity to the reference amino acid sequence. Peptides having 20 to 23 amino and including four amino acid deletions with respect to the reference peptide will have between about 80% to about 83% (i.e., ~82.6%) sequence identity to the reference amino acid sequence.

As stated above, one or more of the amino acids of the peptides may also be chemically modified. Any amino acid modifications known in the art may be made to the amino acids of the peptides using any method known in the art.

In some embodiments, the N-terminal and/or C-terminal amino acid may be modified. For example, the N-terminal amino acid of the peptides may be alkylated, amidated, or acylated at the N-terminal amino ($H_2N$—) group, and, for example, the C-terminal amino acid of the peptides may be amidated or esterified at the C-terminal carboxyl (—COOH) group. For example, the N-terminal amino group may be modified by acylation to include any acyl or fatty acyl group to form an amide, including an acetyl group (i.e., $CH_3$—C(=O)— or a myristoyl group. In some embodiments, the N-terminal amino group may be modified to include an acyl group having formula —C(O)R, wherein R is a linear or branched alkyl group having from 1 to 15 carbon atoms, or may be modified to include an acyl group having formula —C(O)R$^1$, wherein R$^1$ is a linear alkyl group having from 1 to 15 carbon atoms. The C-terminal amino acid of the peptides may also be chemically modified. For example, the C-terminal carboxyl group of the C-terminal amino acid may be chemically modified to include an amino group in place of the hydroxyl group. (i.e., amidated). In some embodiments, the N-terminal and/or C-terminal amino acids are not chemically modified.

The peptide may be acylated at the amino group of the N-terminal amino acid to form an N-terminal amide with an acid selected from the group consisting of:

(i) a $C_2$ to $C_{24}$ aliphatic (saturated or optionally unsaturated) carboxylic acid (for example, an N-terminal amide with acetic acid, with propanoic acid, with butanoic acid, with hexanoic acid, with octanoic acid, with decanoic acid, with dodecanoic acid, with tetradecanoic acid (myristic acid), with hexadecanoic acid, with 9-hexadecenoic acid, with octadecanoic acid, with 9-octadecenoic acid, with 11-octadecenoic acid, with 9,12-octadecadienoic acid, with 9,12,15-octadecatrienoic acid, with 6,9,12-octadecatrienoic acid, with eicosanoic acid, with 9-eicosenoic acid, with 5,8,11,14-eicosatetraenoic acid, with 5,8,11,14,17-eicosapentaenoic acid, with docosanoic acid, with 13-docosenoic acid, with 4,7,10, 13,16,19-docosahexaenoic acid, with tetracosanoic acid, and the like);

(ii) trifluoroacetic acid;

(iii) benzoic acid; and (iv) a $C_1$ to $C_{24}$ aliphatic alkyl sulfonic acid which forms an aliphatic alkyl sulfonamide, wherein the $C_1$ to $C_{24}$ aliphatic alkyl carbon chain structure of the sulfonic acid is analogous to that of the aliphatic alkyl carboxylic acid chains in the aliphatic alkyl carboxylic acids described above. For example, a peptide may be acylated using a carboxylic acid group represented as ($C_1$-$C_{23}$)-alkyl-C(O)OH through dehydrative coupling by way of activation of the carboxylic acid group to form an amide represented as ($C_1$-$C_{23}$)-alkyl-C(O)—NH-peptide. Analogously, a sulfonamide may be formed by reacting a sulfonic acid species (represented as ($C_1$-$C_{23}$)-alkyl-S($O_2$)—X, where X is halogen or $OCH_3$ or other compatible leaving group) with an N-terminal amino group to form a sulfonamide represented as ($C_1$-$C_{23}$)-alkyl-S($O_2$)—NH-peptide.

As another example, the N-terminal amino group of the N-terminal amino acid may be alkylated with a $C_1$ to $C_{24}$ aliphatic alkyl group, the structure of which aliphatic alkyl group is as described above. Alkylation may be effected, for example, using an aliphatic alkyl halide or an aliphatic alkyl sulfonic acid ester (mesylate, tosylate, etc.), preferably using a primary alkyl halide or a primary alkyl sulfonic acid ester. The N-terminal amino acid may be also modified at the terminal amino to include any acyl or aliphatic acyl fatty acyl group as an amide, including an acetyl group (i.e., —C(O) $CH_3$), a myristoyl group, a butanoyl group, a hexanoyl group, a octanoyl group, a decanoyl group, a dodecanoyl group, a tetradecanoyl group, a hexadecanoyl group, a 9-hexadecenoyl group, a octadecanoyl group, a 9-octadecenoyl group, a 11-octadecenoyl group, a 9,12-octadecadienoyl group, a 9,12,15-octadecatrienoyl group, a 6,9,12-octadecatrienoyl group, a eicosanoyl group, a 9-eicosenoyl group, a 5,8,11,14-eicosatetraenoyl group, a 5,8,11,14,17-eicosapentaenoyl group, a docosanoyl group, a 13-docosenoyl group, a 4,7,10, 13,16,19-docosahexaenoyl group, a tetracosanoyl group, which groups are covalently attached to the terminal amino group of the peptide by an amide bond.

The C-terminal carboxylic acid group of the C-terminal amino acid of the peptides of the invention may also be chemically modified. For example, the C-terminal amino acid may be chemically modified by reaction of the C-terminal carboxylic acid group of the peptide with an amine to form an amide group such as an amide of ammonia; an amide of a $C_1$ to $C_{24}$ aliphatic alkyl amine, preferably a linear aliphatic alkyl amine; an amide of a hydroxyl-substituted $C_2$ to $C_{24}$ aliphatic alkyl amine; an amide of a linear 2-($C_1$ to $C_{24}$ aliphatic alkyl) oxyethylamine group; and an amide of an omega-methoxy-poly(ethyleneoxy)$_n$-ethylamine group (also referred to as an omega-methoxy-PEG-alpha-amine group or an omega-methoxy-(polyethylene glycol)amine group), where n is from 0 to 10. The C-terminal carboxylic acid group of the C-terminal amino acid of the peptide may also be in the form of an ester selected from the group consisting of an ester of a $C_1$ to $C_{24}$ aliphatic alkyl alcohol and an ester of a 2-(omega-methoxy-poly(ethyleneoxy)$_n$)-ethanol group, where n is from 0 to 10.

The C-terminal carboxylic acid group on the peptide, which may be represented by the formula peptide-C(O)OH, may also be amidated by conversion to an activated form such as a carboxylic acid halide, carboxylic acid anhydride, N-hydroxysuccinimide ester, pentafluorophenyl (OPfp) ester, 3-hydroxy-2,3-dihydro-4-oxo-benzo-triazone (ODhbt) ester, and the like to facilitate reaction with ammonia or a primary or secondary amine, preferably ammonia or a primary amine, and preferably while any other reactive groups in the peptide are protected by synthetic chemically compatible protecting groups well known in the art of peptide synthesis, especially of peptide solid phase synthesis, such as a benzyl ester, a t-butyl ester, a phenyl ester, etc. A resulting peptide amide could be represented by the formula peptide-C(O)—NR$^3$R$^4$ (the amide being at the C-terminal end of the peptide) wherein R$^3$ and R$^4$ are independently selected from the group consisting of hydrogen; $C_1$ to $C_{24}$ alkyl such as methyl, ethyl, butyl, isobutyl, cyclopropylmethyl, hexyl, dodecyl, tetradecyl, and the like as described above.

The C-terminal carboxylic acid of the C-terminal amino acid may also be converted to an amide of a hydroxyl-substituted $C_2$ to $C_{24}$ aliphatic alkyl amine (the hydroxyl group being attached to a carbon atom rather than a nitrogen atom of the amine) such as 2-hydroxyethylamine, 4-hydroxybutylamine, and 12-hydroxydodecylamine, and the like.

The C-terminal carboxylic acid may also be converted to an amide of a hydroxyl-substituted $C_2$ to $C_{24}$ aliphatic alkyl amine, wherein the hydroxyl group could be acylated to form an ester with a $C_2$ to $C_{24}$ aliphatic carboxylic acid as described above. Preferably, in the peptide amide at the C-terminal end of the peptide represented by the formula peptide-C(O)R$^5$R$^6$, R$^5$ is hydrogen and R$^6$ is selected from the group consisting of hydrogen, $C_1$ to $C_{24}$ alkyl, and hydroxyl-substituted $C_2$ to $C_{24}$ alkyl.

The C-terminal carboxylic acid of the C-terminal amino acid may be converted to an amide of a linear 2-($C_1$ to $C_{24}$ aliphatic alkyl)oxyethylamine. Such an amide may be prepared, for example, by reaction of a linear $C_1$ to $C_{24}$ aliphatic alcohol with potassium hydride in diglyme with 2-chloroethanol to provide a linear $C_1$ to $C_{24}$ aliphatic alkyl ethanol, which can be converted to an amine by oxidation to an aldehyde, followed by reductive amination to an amine (for example using ammonia), or by conversion to an alkyl halide (e.g. using thionyl chloride) followed by treatment with an amine such as ammonia.

The C-terminal carboxylic acid of the C-terminal amino acid may also be converted to an amide of an omega-methoxy-poly(ethyleneoxy)$_n$-ethylamine, where n is from 0 to 10, which can be prepared from the corresponding omega-methoxy-poly(ethyleneoxy)$_n$-ethanol, for example, by conversion of the alcohol to an amine as described above.

In another embodiment, the C-terminal carboxyl may be converted to an amide represented by the formula peptide-C(O)—NR$^7$R$^8$, wherein R$^7$ is hydrogen and R$^8$ is a linear 2-($C_1$ to $C_{24}$ aliphatic alkyl)oxyethyl group wherein the $C_1$ to $C_{24}$ aliphatic alkyl portion is as described above and includes groups such as methoxyethyl (i.e., $CH_3O$—$CH_2CH_2$—), 2-dodecyloxyethyl, and the like; or R$^7$ is hydrogen and R$^8$ is an omega-methoxy-poly(ethyleneoxy)-ethyl group where the n of the poly(ethyleneoxy) portion is from 0 to 10, such as 2-methoxyethyl (i.e., $CH_3O$—$CH_2CH_2$—), omega-methoxyethoxyethyl (i.e., $CH_3O$—$CH_2CH_2O$—$CH_2CH_2$—) up to $CH_3O$—$(CH_2CH_2O)_{10}$—$CH_2CH_2$—.

The C-terminal carboxylic acid group of the C-terminal amino acid of the peptide may also be in the form of an ester of a $C_1$ to $C_{24}$ aliphatic alkyl alcohol, the aliphatic alkyl portion of the alcohol as described above. The C-terminal carboxylic acid group of the C-terminal amino acid of the peptide may also be in the form of an ester of a 2-(omega-methoxy-poly(ethyleneoxy)$_n$)-ethanol group where n is from 0 to 10, which can be prepared from reaction of 2-methoxyethanol as a sodium 2-methoxyethanolate with stoichiometric amounts of ethylene oxide, the stoichiometric amount dependent on the size of n.

A side chain in an amino acid of the peptides may also be chemically modified. For example, a phenyl group in phenylalanine or tyrosine may be substituted with a substituent selected from the group consisting of:

a $C_1$ to $C_{24}$ aliphatic alkyl group (i.e., linear or branched, and/or saturated or unsaturated, and/or containing a cyclic group) such as methyl, ethyl, propyl, isopropyl, butyl, isobutyl, cyclopropyl, 2-methylcyclopropyl, cyclohexyl, octyl, decyl, dodecyl, hexadecyl, octadecyl, eicosanyl, docosanyl, tetracosanyl, 9-hexadecenyl, 9-octadecenyl, 11-octadecenyl, 9,12-octadecadienyl, 9,12,15-octadecatrienyl, 6,9,12-octadecatrienyl, 9-eicosenyl, 5,8,11,14-eicosatetraenyl, 5,8,11,14,17-eicosapentaenyl, 13-docosenyl, and 4,7,10,13,16,19-docosahexaenyl;

a $C_1$ to $C_{24}$ aliphatic alkyl group substituted with a hydroxyl group at least one carbon atom away from a site of unsaturation, examples of which hydroxyalkyl group include hydroxymethyl, hydroxyethyl, hydroxydodecyl, and the like;

a $C_1$ to $C_{74}$ alkyl group substituted with a hydroxyl group that is esterified with a $C_2$ to $C_{24}$ aliphatic carboxyl group of an acid such as acetic acid, butanoic acid, hexanoic acid, octanoic acid, decanoic acid, dodecanoic acid, tetradecanoic acid, hexadecanoic acid, 9-hexadecenoic acid, octadecanoic acid, 9-octadecenoic acid, 11-octadecenoic acid, 9,12-octadecadienoic acid, 9,12,15-octadecatrienoic acid, 6,9,12-octadecatrienoic acid, eicosanoic acid, 9-eicosenoic acid, 5,8,11,14-eicosatetraenoic acid, 5,8,11,14,17-eicosapentaenoic acid, docosanoic acid, 13-docosenoic acid, 4,7,10,13,16,19-docosahexaenoic acid, tetracosanoic acid, and the like, a dicarboxylic acid such as succinic acid, or a hydroxyacid such as lactic acid, wherein the total number of carbon atoms of the ester substituent is between 3 and 25;

halogen such as fluoro-, chloro-, bromo-, and iodo-; nitro-; amino- such as $NH_2$, methyl amino, dimethylamino; trifluoromethyl-; carboxyl (—COOH);

a $C_1$ to $C_{24}$ alkoxy (such as can be formed by alkylation of tyrosine) such as methoxy, ethoxy, propyloxy, isopropyloxy, butyloxy, isobutyloxy, cyclopropyloxy, 2-methoxycyclopropyloxy, cyclohexyloxy, octyloxy, decyloxy, dodecyloxy, hexadecyloxy, octadecyloxy, eicosanyloxy, docosanyloxy, tetracosanyloxy, 9-hexadecenyloxy, 9-octadecenyloxy, 11-octadecenyloxy, 9,12-octadecadienyloxy, 9,12,15-octadecatrienyloxy, 6,9,12-octadecatrienyloxy, 9-eicosenyloxy, 5,8,11,14-eicosatetraenyloxy, 5,8,11,14,17-eicosapentaenyloxy, 13-docosenyloxy, and 4,7,10,13,16,19-docosahexaenyloxy; and a $C_2$ to $C_{24}$ hydroxyalkyloxy such as 2-hydroxyethyloxy and esters thereof with carboxylic acids as described above or with trifluoroacetic acid.

A serine hydroxyl group may be esterified with a substituent selected from the group consisting of:

a $C_2$ to $C_{24}$ aliphatic carboxylic acid group such as described above;

a trifluoroacetic acid group; and a benzoic acid group.

The epsilon amino group in lysine may be chemically modified, for example, by amide formation with: a $C_2$ to $C_{24}$ aliphatic carboxylic acid group (for example, by reaction of the amine with a chemically activated form of a carboxylic acid such as an acid chloride, an anhydride, an N-hydroxysuccinimide ester, a pentafluorophenyl (OPfp) ester, a 3-hydroxy-2,3-dihydro-4-oxo-benzo-triazone (ODhbt) ester, and the like) such as described above, or a benzoic acid group, or an amino acid group. Additionally, the epsilon amino group in lysine may be chemically modified by alkylation with one or two $C_1$ to $C_4$ aliphatic alkyl groups.

The carboxylic acid group in glutamic acid may be modified by formation of an amide with an amine such as: ammonia; a $C_1$ to $C_{24}$ primary aliphatic alkyl amine (the alkyl portion of which is as described above) including with methylamine; or an amino group of an amino acid.

The carboxylic acid group in glutamic acid may be modified by formation of an ester with a $C_1$ to $C_{24}$ aliphatic hydroxyalkyl group as described above, preferably an ester with a primary alcohol of a $C_1$ to $C_{24}$ aliphatic alkyl such as methanol, ethanol, propan-1-ol, n-dodecanol, and the like as described above.

The peptides of the invention have a mucin-inhibiting effect and/or mucus-inhibiting effect when administered to a mammal in a mucin- and/or mucus-inhibiting amount. The peptides may also have (1) a greater mucin-inhibiting effect in a mammal than MANS peptide when administered at equal concentrations, (2) a greater mucus-inhibiting effect in a mammal than MANS peptide when administered at equal concentrations, and/or (3) have greater aqueous solubility than the MANS peptide.

The MARCKS peptide and the MANS peptide each comprise a myristoyl group linked to the amine at the N-terminal amino acid by an amide bond. However, as disclosed herein, mucin hypersecretion-inhibiting activity of the peptides of the invention does not reside with the presence of a myristoyl group at the N-terminal amino acid of the peptide sequence. Indeed, certain peptides of the invention which do not contain an N-terminal chemical modification are found to exhibit mucin hypersecretion-inhibiting activity. Certain peptides of the invention which contain N-terminal chemical modification by groups other than myristoyl, such as an acetyl group as an N-terminal amide also are found to exhibit mucin hypersecretion-inhibiting activity. Indeed, an N-terminal acetylated version of the MANS peptide (non-myristylated) can exhibit mucin hypersecretion-inhibiting activity in the methods of this invention. In addition, the peptide sequence of amino acids comprising the MANS peptide amino acid sequence and variants thereof as described herein can exhibit mucin hypersecretion-inhibiting activity in the methods of this invention.

In one aspect, this invention provides a method of inhibiting mucin hypersecretion in a mammal, the method comprising administering to the mammal a mucin hypersecretion-inhibiting amount of a peptide that inhibits mucin hypersecretion, the peptide having an amino acid sequence selected from the group consisting of: (a) an amino acid sequence having the sequence, GAQFSKTAAKGEAAAER-PGEAAVA (SEQ ID NO. 1); and (b) an amino acid sequence substantially identical to the sequence defined in (a); wherein the N-terminal amino acid of the peptide is not myristoylated and the C-terminal amino acid of the peptide is optionally independently chemically modified, the peptide having a mucin hypersecretion-inhibiting effect when administered to a mammal in a mucin hypersecretion-inhibiting amount. In one embodiment, the N-terminal amino acid of this peptide is preferably acetylated. In another embodiment, the peptide exhibits at least one of the properties of (a) greater mucin hypersecretion-inhibiting effect on a mammal than SEQ ID NO. 1, wherein the N-terminal amino acid is myristoylated when administered to said mammal at equal concentrations or (b) greater aqueous solubility than SEQ ID NO. 1, wherein the N-terminal amino acid is myristoylated at equal concentrations in the same liquid.

In some embodiments, the N-terminal amino group may be modified to include an acyl group having formula —C(O)R, wherein R is a linear or branched alkyl group having from 1 to 15 carbon atoms, or may be modified to include an acyl group having formula —C(O)R$^1$, wherein R$^1$ is a linear alkyl group having from 1 to 15 carbon atoms. The C-terminal amino acid of the peptides may also be chemically modified. For example, the C-terminal carboxyl group of the C-terminal amino acid may be chemically modified to include an amino group in place of the hydroxyl group. (i.e., amidated). In some embodiments, the N-terminal and/or C-terminal amino acids are not chemically modified.

In some embodiments, the peptides may have a greater half-life in human bronchoalveolar lavage fluid (BALF) than in human plasma, and may also have a greater half-life in human mucus (e.g., in mucus from a subject with cystic fibrosis) than in human plasma.

The peptides may be used in methods of inhibiting mucin secretion and/or mucus production in a mammal, methods of treating hypersecretion of mucin and/or mucus in a mammal, and methods of treating pulmonary diseases causing hypersecretion of mucin and/or mucus in a mammal (such as, for example, asthma, chronic bronchitis, COPD, and cystic fibrosis). Conditions that may be suitable for treatment by the peptides include, but are not limited to, inflammatory, viral, or bacterial airway disease (e.g., asthma, chronic obstructive pulmonary disease (COPD), common cold, rhinitis, acute or chronic bronchitis, pneumonia, and kennel cough), allergic conditions (e.g., atopy, allergic inflammation), bronchiectasis, emphysema, bronchial asthma, and certain genetic conditions (e.g., cystic fibrosis). The peptides may also be suitable for treatment of conditions and diseases described in, as well as for methods described in, U.S. patent application Ser. No. 10/180,753 (Publication No. U.S. 2003/0013652) and Ser. No. 09/256,154 and International Application No. PCT/US00/05050 (International Publication Number WO 00/50062), the entire contents of which are incorporated herein by reference.

In addition to mucin hypersecretion associated with a disease, the term mucin hypersecretion also includes ATP-induced mucin hypersecretion as well as secretagogue-induced mucin hypersecretion and stimulated mucin hypersecretion.

In a preferred embodiment, the current invention provides a mucin hypersecretion-inhibiting peptide having an amino acid sequence of from 4 to 23 contiguous amino acids of a reference amino acid sequence, PEPTIDE 1, wherein the mucin hypersecretion-inhibiting peptide is selected from:

(a) the group consisting of peptide 2, peptide 3, peptide 4, peptide 5, peptide 6, peptide 7, peptide 8, peptide 9, peptide 10, peptide 11, peptide 12, peptide 13, peptide 14, peptide 15, peptide 16, peptide 17, peptide 18, peptide 19, peptide 20, peptide 21, peptide 22, peptide 23, peptide 24, peptide 25, peptide 26, peptide 27, peptide 28, peptide 29, peptide 30, peptide 31, peptide 32, peptide 33, peptide 34, peptide 35, peptide 36, peptide 37, peptide 38, peptide 39, peptide 40, peptide 41, peptide 42, peptide 43, peptide 44, peptide 45, peptide 46, peptide 47, peptide 48, peptide 49, peptide 50, peptide 51, peptide 52, peptide 53, peptide 54, peptide 56, peptide 57, peptide 58, peptide 59, peptide 60, peptide 61, peptide 62, peptide 63, peptide 64, peptide 67, peptide 68, peptide 69, peptide 70, peptide 71, peptide 72, peptide 73, peptide 74, peptide 75, peptide 79, peptide 80, peptide 81, peptide 82, peptide 83, peptide 84, peptide 85, peptide 86, peptide 87, peptide 92, peptide 93, peptide 94, peptide 95, peptide 96, peptide 97, peptide 98, peptide 99, peptide 100, peptide 106, peptide 107, peptide 108, peptide 109, peptide 110, peptide 111, peptide 112, peptide 113, peptide 114, peptide 122, peptide 123, peptide 124, peptide 125, peptide 126, peptide 127, peptide 128, peptide 129, peptide 139, peptide 140, peptide 141, peptide 142, peptide 143, peptide 144, peptide 145, peptide 157, peptide 158, peptide 159, peptide 160, peptide 161, peptide 162, peptide 176, peptide 177, peptide 178, peptide 179, peptide 180, peptide 196, peptide 197, peptide 198, peptide 199, peptide 217, and peptide 219 as described herein; and, (b) an amino acid sequence having between 80% to 96% sequence identity to the sequence defined in (a);

wherein the amine of the N-terminal amino acid of the mucin hypersecretion-inhibiting peptide amino acid sequence is optionally covalently bonded by an amide bond to a carboxylic acid selected from the group consisting of myristic acid and acetic acid, and wherein the carboxyl of the C-terminal amino acid of the mucin hypersecretion-inhibiting peptide amino acid sequence is optionally covalently bonded by an amide bond to ammonia.

The peptides may be administered locally or systemically (e.g., in the from of a pharmaceutical composition comprising a peptide of the invention and a pharmaceutically acceptable carrier) and may be administered to any part of a mammal's body, including, but not limited to, those parts of the body that produce mucus and/or mucin (e.g., preferably to respiratory passages, nasal cavity, oral cavity, trachea, lungs, gastrointestinal tract, eye, reproductive tract, etc.). The peptides may be administered in various ways, including, but not limited to, topical administration, parenteral administration, rectal administration, pulmonary administration, nasal administration, inhalation, insufflation, and oral administration. Pulmonary administration may be accomplished, for example, using an aerosolizer, a nebulizer, a dry powder inhaler, a metered dose inhaler, and the like.

The peptides may be prepared and administered as pharmaceutical formulations suitable for any pharmaceutically effective administration route. The peptides of the invention (or pharmaceutical formulations thereof) may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing).

The peptides may be administered to the airways of a mammal by any suitable method, including generating an aerosol that includes the peptide. Such an aerosol may be a solid or liquid, and may be aqueous-based. Suitable size particles of such an aerosol may be produced in various ways known in the art. Particles of such an aerosol are typically less than 50 micrometers in size, preferably in the range of about 0.1 micrometers to about 10 micrometers in size, more preferably in the range of about 1 micrometer to about 10 micrometers in size, and even more preferably in the range of about 2 to about 7 micrometers in size, and preferably about 2 to about 7 micrometers.

Nasal administration of a peptide (or a pharmaceutical formulation of a peptide) may be accomplished, for example, by spray application of an aqueous solution or suspension of a peptide or by application of an aqueous solution or suspension of a peptide as a drop or droplet such as from a dropper or pipette, for example in the form of a pharmaceutically acceptable, preferably sterile, saline (NaCl) solution which may be optionally buffered. Sterilization of an aqueous solution may be accomplished, for example, by sterile filtration of an aqueous solution comprising the peptide, optionally in the presence of pharmaceutically acceptable additives such as preservatives, antioxidants, buffering salts, tonicity modifiers, and the like. Sterilization of an aqueous suspension comprising the peptide may be accomplished, for example, by irradiation or sterile filtration when the suspended material is smaller in particle size than 0.2 micrometers, for example a suspension comprising a micelle, a liposome such as a phospholipid-stabilized liposome, or similar particle which can pass through a 0.2 micrometer filter. An aqueous solution (e.g., an isotonic saline solution or hypertonic saline solution, and optionally a sugar which will not chemically react with the peptide) of a therapeutically effective amount of a peptide of the invention can be sterilized, for example by sterile filtration, placed as an aliquot containing a therapeutically effective amount of peptide into a sterile vial, lyophilized to form a dried powder, and sealed, preferably in the presence of an inert atmosphere or gas, using a sterile stopper or cap. Prior to use, the dried powder can be rehydrated by the addition of sufficient water to form an isotonic solution as a single dose which can be administered as an aerosol to the airway of a mammal.

The amount of peptide or pharmaceutical formulation thereof administered to a mammal may vary depending upon multiple factors including, but not limited to, the particular peptide, the type of mammal, the mammal's degree of illness, the mammal's weight, and the mammal's age. In addition, it may be desirable to maintain some level of mucin secretion/mucus production (e.g., a normal or basal level) in a mammal being treated with a peptide. In one embodiment, a human is the preferred mammal in need of treatment, and the amount of peptide that is administered is sufficient to inhibit mucin hypersecretion which is administered in single or multiple dose. The single dose of peptide of the present invention may range from 0.1 mg to about 30 mg/kg body weight, preferably from about 0.1 mg to about 15 mg/kg body weight, and more preferably from about 0.1 mg to about 7.5 mg/kg body weight. The number of doses and duration of treatment is dependent upon the subject's response to treatment. Adjustments as to the amount of single dose, number of doses and duration of the treatment can be determined by the health care provider dependent upon the symptoms and severity of these symptoms.

In one embodiment, an isolated peptide consists of less than 24 amino acids and has an amino acid sequence selected from the group consisting of (a) an amino acid sequence having from 4 to 23 contiguous amino acids (or, in other embodiments, from 8 to 14 contiguous amino acids or from 10 to 12 contiguous amino acids) of the reference sequence PEPTIDE 1, wherein the amino acid sequence begins from the N-terminal amino acid of the reference sequence; (b) a sequence substantially similar to the amino acid sequence defined in (a); (c) an amino acid sequence having from 4 to 23 contiguous amino acids (or, in other embodiments, from 8 to 14 contiguous amino acids or from 10 to 12 contiguous amino acids) of the reference sequence PEPTIDE 1, wherein the amino acid sequence ends at the C-terminal amino acid of the reference sequence; and (d) a sequence substantially similar to the amino acid sequence defined in (c). The N-terminal amino group of the N-terminal amino acid and/or the C-terminal carboxyl group of the C-terminal amino acid may optionally be chemically modified as follows:

(1) the N-terminal amine group of the N-terminal amino acid of the peptide is optionally in the form of an amide selected from the group consisting of:
an amide of a $C_2$ to $C_{24}$ aliphatic carboxylic acid,
an amide of trifluoroacetic acid,
an amide of benzoic acid, and
an amide of a $C_1$ to $C_{24}$ aliphatic alkyl sulfonic acid; or
the N-terminal amine group of the N-terminal amino acid of the peptide is optionally alkylated with a group selected from the group consisting of:
a $C_1$ to $C_{24}$ aliphatic alkyl group,
a linear 2-($C_1$ to $C_{24}$ aliphatic alkyl)oxyethyl group,
an omega-methoxy-poly(ethyleneoxy)$_a$-ethyl group, where n is from 0 to 10; and (2) the C-terminal carboxylic acid group of the C-terminal amino acid of the peptide is optionally in the form of an amide selected from the group consisting of:
an amide of ammonia,
an amide of a $C_1$ to $C_{24}$ aliphatic alkyl amine,
an amide of a hydroxyl-substituted $C_2$ to $C_{24}$ aliphatic alkyl amine,
an amide of a linear 2-(C1 to C24 aliphatic alkyl)oxyethylamine group, and
an amide of an omega-methoxy-poly(ethyleneoxy)$_n$-ethylamine group, where n is from 0 to 10; or
the C-terminal carboxylic acid group of the C-terminal amino acid of the peptide is optionally in the form of an ester selected from the group consisting of:
an ester of a $C_1$ to $C_{24}$ aliphatic alkyl alcohol,
an ester of a 2-(omega-methoxy-poly(ethyleneoxy)$_n$)-ethanol group, where n is from 0 to 10.
The peptide has a mucin release-inhibiting effect when administered to a mammal in a mucin-inhibiting amount. The peptide may also have a greater mucin-inhibiting effect on a mammal than MANS peptide when administered at equal concentrations and/or greater aqueous solubility than MANS peptide.

In another embodiment, an isolated peptide consists of less than 24 amino acids and has an amino acid sequence consisting of a variant of an amino acid sequence having from 4 to 23 contiguous amino acids (or, in other embodiments, from 8 to 14 contiguous amino acids or from 10 to 12 contiguous amino acids) of the reference sequence PEPTIDE 1, wherein the amino acid sequence begins from the N-terminal amino acid of the reference sequence or wherein the amino acid sequence ends at the C-terminal amino acid of the reference sequence. The N-terminal amino group of the N-terminal amino acid and/or the C-terminal carboxyl group of the C-terminal amino acid may optionally be chemically modified as follows:

(1) the N-terminal amine group of the N-terminal amino acid of the peptide is optionally in the form of an amide selected from the group consisting of:
an amide of a $C_2$ to $C_{24}$ aliphatic carboxylic acid,
an amide of trifluoroacetic acid,
an amide of benzoic acid, and
an amide of a $C_1$ to $C_{24}$ aliphatic alkyl sulfonic acid; or
the N-terminal amine group of the N-terminal amino acid of the peptide is optionally alkylated with a group selected from the group consisting of:
a $C_1$ to $C_{24}$ aliphatic alkyl group,
a linear 2-($C_1$ to $C_{24}$ aliphatic alkyl)oxyethyl group,
an omega-methoxy-poly(ethyleneoxy)$_n$-ethyl group, where n is from 0 to 10; and (2) the C-terminal carboxylic acid group of the C-terminal amino acid of the peptide is optionally in the form of an amide selected from the group consisting of:
an amide of ammonia,
an amide of a $C_1$ to $C_{24}$ aliphatic alkyl amine,
an amide of a hydroxyl-substituted $C_2$ to $C_{24}$ aliphatic alkyl amine,
an amide of a linear 2-(C1 to C24 aliphatic alkyl)oxyethylamine group, and
an amide of an omega-methoxy-poly(ethyleneoxy)$_n$-ethylamine group, where n is from 0 to 10; or
the C-terminal carboxylic acid group of the C-terminal amino acid of the peptide is optionally in the form of an ester selected from the group consisting of:
an ester of a $C_1$ to $C_{24}$ aliphatic alkyl alcohol,
an ester of a 2-(omega-methoxy-poly(ethyleneoxy)$_n$)-ethanol group, where n is from 0 to 10.
The peptide has a mucin-inhibiting effect when administered to a mammal in a mucin-inhibiting amount. The peptide also has a greater mucin-inhibiting effect on a mammal than MANS peptide when administered at equal concentrations and/or has greater aqueous solubility than MANS peptide.

In a further embodiment, a method of inhibiting mucin hypersecretion in a mammal comprises administering to the mammal a mucin-inhibiting amount of an isolated peptide that inhibits mucin secretion. The isolated peptide consists of less than 24 amino acids and has an amino acid sequence selected from the group consisting of (a) an amino acid sequence having from 4 to 23 contiguous amino acids (or, in other embodiments, from 8 to 14 contiguous amino acids or from 10 to 12 contiguous amino acids) of the reference sequence PEPTIDE 1, wherein the amino acid sequence begins from the N-terminal amino acid of the reference sequence; (b) a sequence substantially similar to the amino acid sequence defined in (a); (c) an amino acid sequence having from 4 to 23 contiguous amino acids (or, in other embodiments, from 8 to 14 contiguous amino acids or from 10 to 12 contiguous amino acids) of the reference sequence PEPTIDE 1, wherein the amino acid sequence ends at the C-terminal amino acid of the reference sequence; and (d) a sequence substantially similar to the amino acid sequence defined in (c). The N-terminal amino group of the N-terminal amino acid and/or the C-terminal carboxyl group of the C-terminal amino acid may optionally be chemically modified as follows:

(1) the N-terminal amine group of the N-terminal amino acid of the peptide is optionally in the form of an amide selected from the group consisting of:
an amide of a $C_2$ to $C_{24}$ aliphatic carboxylic acid, an amide of trifluoroacetic acid, an amide of benzoic acid, and an amide of a $C_1$ to $C_{24}$ aliphatic alkyl sulfonic acid; or the N-terminal amine group of the N-terminal amino acid of the peptide is optionally alkylated with a group selected from the group consisting of:

a $C_1$ to $C_{24}$ aliphatic alkyl group, a linear 2-($C_1$ to $C_{24}$ aliphatic alkyl)oxyethyl group, an omega-methoxy-poly(ethyleneoxy)-ethyl group, where n is from 0 to 10; and (2) the C-terminal carboxylic acid group of the C-terminal amino acid of the peptide is optionally in the form of an amide selected from the group consisting of:

an amide of ammonia, an amide of a $C_1$ to $C_{24}$ aliphatic alkyl amine, an amide of a hydroxyl-substituted $C_2$ to $C_{24}$ aliphatic alkyl amine, an amide of a linear 2-(C1 to C24 aliphatic alkyl)oxyethylamine group, and an amide of an omega-methoxy-poly(ethyleneoxy)$_n$-ethylamine group, where n is from 0 to 10; or the C-terminal carboxylic acid group of the C-terminal amino acid of the peptide is optionally in the form of an ester selected from the group consisting of:

an ester of a $C_1$ to $C_{24}$ aliphatic alkyl alcohol, an ester of a 2-(omega-methoxy-poly(ethyleneoxy)$_n$)-ethanol group, where n is from 0 to 10.

The peptide may have a greater mucin-inhibiting effect on a mammal than MANS peptide when administered at equal concentrations and/or greater aqueous solubility than MANS peptide.

The peptides of the invention may be prepared by any suitable method, including solid-phase peptide synthesis techniques such as, for example, using fluorenylmethyloxycarbonyl (FMoc) chemistry and a suitable peptide synthesizer such as a CS-Bio Peptide Synthesizer, or using tert-butyoxycarbonyl (Boc) chemistry and a suitable peptide synthesizer such as an ABI 430A Peptide Synthesizer. Protected amino acids suitable for use in either FMoc or Boc synthesis are commercially available, for example from Calbiochem, a unit of EMD Biosciences, San Diego, Calif. In solid phase peptide synthesis, the C-terminal carboxyl group of the desired peptide as an N-alpha-protected amino acid is covalently bound to a polymer support. The N-alpha-amino protecting group is then removed and a second N-alpha-protected amino acid is coupled to the attached amino acid by formation of an amide bond to the deprotected N-alpha-amine of the amino acid linked to the resin. These steps are repeated with the respective protected amino acids of the desired peptide sequence until the desired sequence is obtained. At the end of the synthesis, the bond between the C-terminal amino acid and the polymer support is cleaved to liberate the peptide. The peptide can be isolated and purified by HPLC. Useful HPLC purification methods include ion exchange chromatography and reverse phase chromatography. Solutions of peptides can be evaporated or lyophilized to provide isolated peptide in solid form. Peptides containing oxidizable groups such as methionine, cysteine, tryptophan, residues are preferably maintained in an oxygen-free atmosphere, and, when formulated and stored in solution or suspension, used in oxygen-free solvents.

Coupling of activated ester to the amine end of the resin-linked peptide during synthesis can be done, for example, using an excess such as a 4-fold excess of amino acid and benzotriazol-1-yl-oxy-tris-dimethylamino-phosphonium hexafluorophosphate, and an excess such as a 6-fold excess of N,N-diisopropylethylamine. Peptides from Fmoc synthesis are cleaved from the resin with trifluoroacetic acid/thioanisole/triisopropylsilane/methanol (for example at a ratio of 90:5:2.5:2.5, vol/vol/vol/vol) at 20° C. for 4 h and those from Boc synthesis with for example HF/anisole (9:1, vol/vol) at 4° C. for 1 h.

In an Fmoc peptide strategy, the first Fmoc amino acid is attached to an insoluble support resin via an acid labile linker. Deprotection of Fmoc is accomplished by treatment of the amino acid with a base such as piperidine. A second Fmoc amino acid is coupled utilizing a pre-activated species or in situ activation (coupling reactions can be done in situ using activating reagents known in peptide chemistry such as DCC, HBTU, TBTU, BOP, BOP-Cl, and the like). After the desired peptide is synthesized, the resin bound peptide is deprotected and detached from the solid support by acidolysis cleavage with weak acids such as trifluoroacetic acid (TFA) or TMSBr in the presence of a scavenger such as a thiol compound, phenol, and water, for example. In one aspect, prior to deprotection of side chain functionality and cleavage from the resin, the terminal amine group of the peptide can be treated with a carboxylic (e.g., aliphatic carboxylic, trifluoroacetic, benzoic and the like), for example, with an aliphatic carboxylic acid species such as an activated form of an aliphatic carboxylic acid such as a pentafluoroester in a manner analogous to the formation of a peptide bond to form an amide of the carboxylic or with an aliphatic sulfonic acid species (such as a sulfonyl chloride) to form a sulfonamide at the N-terminal of the peptide. Alternatively, the N-terminal amine can be alkylated with, for example, an aliphatic alkylating agent (e.g., an aliphatic mesylate or tosylate) obtained by reaction of the corresponding sulfonyl chloride and a base such as pyridine with an aliphatic alcohol, which alcohol can be obtained by reduction (e.g., by lithium aluminum hydride) of an aliphatic carboxylic acid. In another aspect, corresponding D-amino acids (e.g., up to four D-amino acids) with the remainder as L-amino acids can be used in the peptide synthesis procedure to provide a peptide of the invention which can be optionally chemically modified as above. In another aspect, when the desired peptide amino acid sequence is formed, for example by solid phase synthesis, and the side chain protecting groups have been selected to withstand the ester cleaving step to liberate the peptide from the resin, a side-chain protected peptide having a free carboxylic acid at the C-terminal end of the peptide is formed. The C-terminal carboxylic acid can be converted to an active ester (e.g. a pentafluorophenyl ester) and treated with an amine such as ammonia to form an amide (represented as peptide-C(O)—$NH_2$), or with an aliphatic amine as described above to form an aliphatic amide of the peptide, and any remaining protecting groups can be removed to provide the desired peptide of the invention. Additionally, a C-terminal carboxylic ester can be formed from a C-terminal carboxylic acid and an aliphatic alcohol by dehydrative coupling such as by use of a carbodiimide reagent. Acid functional group-containing amino acids such as aspartic acid and glutamic acid can be converted to amides and esters in a fashion analogous to the above method, and the epsilon amine group in lysine can be converted to amides and aliphatic amines as described above for chemistry on the terminal amino group.

Examples of protected amino acids that are useful in FMoc solid phase synthesis of peptides of this invention include the following non-limiting examples: N-alpha-Fmoc-L-alanine pentafluorophenyl ester; N-alpha-Fmoc-N-alpha-(2-Fmoc-oxy-4-methoxybenzyl)-alanine pentafluorophenyl ester; N-alpha-Fmoc-glycine pentafluorophenyl ester; N-alpha-Fmoc-N-alpha-(2-Fmoc-oxy-4-methoxybenzyl)-glycine pentafluorophenyl ester; N-alpha-Fmoc-L-glutamic acid g-2-phenylisopropyl ester; N-alpha-Fmoc-L-glutamic acid alpha-4-{N-[1-(4,4-dimethyl-2,6-dioxocyclohexylidene)-3-methylbutyl]-amino}benzyl ester; N-alpha-Fmoc-L-glutamic acid gamma-4-{N-[1-(4,4-dimethyl-2,6-dioxocyclohexylidene)-3-methylbutyl]-amino} benzyl ester; N-alpha-Fmoc-L-glutamic acid alpha-allyl ester; N-alpha-Fmoc-L-glutamic acid g-benzyl ester; N-alpha-Fmoc-L-glutamic acid alpha-t-butyl ester; N-alpha-Fmoc-L-glutamic acid gamma-t-butyl ester; N-alpha-Fmoc-L-glutamic acid gamma-t-butyl ester pentafluorophenyl ester; N-alpha,epsilon-Di-Fmoc-L-lysine pentafluorophenyl ester; N-alpha,epsilon-di-Fmoc-L-lysine; N-alpha-1-(4,4-Dimethyl-2,6-dioxocyclohex-1-ylidene)ethyl-N-epsilon-Fmoc-L-lysine; N-alpha-Fmoc-L-lysine; N-alpha-Fmoc-N-alpha-(2-Fmoc-oxy-4-methoxybenzyl)-N-epsilon-t-butoxycarbonyl-L-lysine; N-alpha-Fmoc-N-epsilon-1-(4,4-dimethyl-2,6-dioxocyclohex-1-ylidene)-3-methylbutyl-L-lysine; N-alpha-Fmoc-N-epsilon-1-(4,4-dimethyl-2,6-dioxocyclohex-1-ylidene)ethyl-L-lysine; N-alpha-Fmoc-N-epsilon-2-chloro-CBZ-L-lysine; N-alpha-Fmoc-N-epsilon-4-methyltrityl-L-lysine; N-alpha-Fmoc-N-epsilon-acetyl-L-lysine; N-alpha-Fmoc-N-epsilon-benzyloxycarbonyl-L-lysine; N-alpha-Fmoc-N-epsilon-t-Boc-L-lysine; N-alpha-Fmoc-N-epsilon-t-Boc-L-lysine pentafluorophenyl ester; N-alpha-Fmoc-N-epsilon-trifluoroacetyl-L-lysine; N-alpha-Fmoc-4-chloro-L-phenylalanine; N-alpha-Fmoc-4-cyano-L-phenylalanine; N-alpha-Fmoc-4-fluoro-L-phenylalanine; N-alpha-Fmoc-4-nitro-L-phenylalanine; N-alpha-Fmoc-L-phenylalanine; N-alpha-Fmoc-L-phenylalanine pentafluorophenyl ester; N-alpha-Fmoc-N-alpha-(2-Fmoc-oxy-4-methoxybenzyl)-phenylalanine; N-alpha-Fmoc-N-alpha-methyl-L-phenylalanine; N-alpha-Fmoc-L-proline pentafluorophenyl ester; N-alpha-Fmoc-gamma-(4,4'-dimethoxybenzhydry)-L-glutamine; N-alpha-Fmoc-gamma-trityl-L-glutamine pentafluorophenyl ester; N-alpha-Fmoc-L-glutamine; N-alpha-Fmoc-L-glutamine pentafluorophenyl ester; N-alpha-Fmoc-N-gamma-trityl-L-glutamine; N-alpha-Fmoc-$N^G$-(4-methoxy-2,3,6-trimethylbenzenesulfonyl)-L-arginine N-methoxy-N-methyl amide; N-alpha-Fmoc-$N^G$-2,2,4,6,7-pentamethyldihydrobenzofuran-5-sulfonyl-L-arginine; N-alpha-Fmoc-$N^G$-2,2,5,7,8-pentamethylchroman-6-sulfonyl-L-arginine; N-alpha-Fmoc-$N^G$-4-methoxy-2,3,6-trimethylbenzenesulfonyl-L-arginine; N-alpha-Fmoc-$N^G$-4-methoxy-2,3,6-trimethylbenzenesulfonyl-L-arginine pentafluorophenyl ester; N-alpha-Fmoc-$N^G$-nitro-L-arginine; N-alpha-Fmoc-$N^G$-tosyl-L-arginine; N-alpha-Fmoc-O-(2-acetamido-2-deoxy-3,4,6-tri-O-acetyl-alpha-D-galactopyranosyl)-L-serine; N-alpha-Fmoc-L-serine; N-alpha-Fmoc-O-benzyl-L-phosphoserine; N-alpha-Fmoc-O-benzyl-L-serine; N-alpha-Fmoc-O-t-butyl-L-serine; N-alpha-Fmoc-O-t-butyl-L-serine N-hydroxysuccinimide; N-alpha-Fmoc-O-trityl-L-serine; N-alpha-Fmoc-L-threonine; N-alpha-Fmoc-O-benzyl-L-phosphothreonine; N-alpha-Fmoc-O-benzyl-L-threonine; N-alpha-Fmoc-O-t-butyl-L-threonine; N-alpha-Fmoc-O-trityl-L-threonine; N-alpha-Fmoc-O-(2-acetamido-2-deoxy-3,4,6-tri-O-acetyl-alpha-D-galactopyranosyl)-L-threonine; N-alpha-Fmoc-L-valine; N-alpha-Fmoc-L-valine pentafluorophenyl ester; N-alpha-Fmoc-N-alpha-(2-Fmoc-oxy-4-methoxybenzyl)-valine; N-alpha-Fmoc-N-alpha-(2-Fmoc-oxy-4-methoxybenzyl)-valine pentafluorophenyl ester; N-alpha-Fmoc-N-alpha-methyl-L-valine; N-alpha-Fmoc-O-(bis-dimethylaminophosphono)-L-tyrosine; N-alpha-Fmoc-L-tyrosine; N-alpha-Fmoc-O-2,6-dichlorobenzyl-L-tyrosine; N-alpha-Fmoc-O-2-bromo-CBZ-L-tyrosine; N-alpha-Fmoc-O-2-chlorotrityl-L-tyrosine; N-alpha-Fmoc-O-benzyl-L-phosphotyrosine; N-alpha-Fmoc-O-methyl-L-tyrosine; N-alpha-Fmoc-O-phospho-L-tyrosine; N-alpha-Fmoc-O-t-butyl-L-tyrosine; N-alpha-Fmoc-O-t-butyl-L-tyrosine pentafluorophenyl ester; N-alpha-Fmoc-L-aspartic acid beta-1-adamantyl ester; N-alpha-Fmoc-L-aspartic acid beta-2-adamantyl ester; -alpha-Fmoc-L-aspartic acid beta-2-phenylisopropyl ester; N-alpha-Fmoc-L-aspartic acid beta-4-{N-[1-(4,4-dimethyl-2,6-dioxocyclohexylidene)-3-methylbutyl]-amino}benzyl ester; N-alpha-Fmoc-L-aspartic acid alpha-4-{N-[1-(4,4-dimethyl-2,6-dioxocyclohexylidene)-3-methylbutyl]-amino} benzyl ester; N-alpha-Fmoc-L-aspartic acid alpha-allyl ester; N-alpha-Fmoc-L-aspartic acid beta-benzyl ester; N-alpha-Fmoc-L-aspartic acid alpha-t-butyl ester; N-alpha-Fmoc-L-aspartic acid beta-t-butyl ester; N-alpha-Fmoc-L-aspartic acid beta-t-butyl ester pentafluorophenyl ester; N-alpha-Fmoc-L-aspartic acid-beta-1-adamantyl ester pentafluorophenyl ester; N-alpha-Fmoc-L-aspartic acid-beta-2-adamantyl ester pentafluorophenyl ester; N-alpha-Fmoc-L-leucine; N-alpha-Fmoc-L-leucine pentafluorophenyl ester; N-alpha-Fmoc-N-alpha-(2-Fmoc-oxy-4-methoxybenzyl)-leucine; N-alpha-Fmoc-N-alpha-(2-Fmoc-oxy-4-methoxybenzyl)-leucine pentafluorophenyl ester; N-alpha-Fmoc-N-alpha-methyl-L-leucine; N-alpha-Fmoc-L-isoleucine; N-alpha-Fmoc-L-isoleucine pentafluorophenyl ester; N-alpha-Fmoc-N-alpha-methyl-L-isoleucine; N-alpha-Fmoc-beta-2,4,6-trimethoxybenzyl-L-asparagine; N-alpha-Fmoc-beta-trityl-L-asparagine pentafluorophenyl ester; N-alpha-Fmoc-L-asparagine; N-alpha-Fmoc-L-asparagine pentafluorophenyl ester; N-alpha-Fmoc-N-beta-(3,4,6-tri-O-acetyl-2-(acetylamino)-deoxy-2-beta-glucopyranosyl)-L-asparagine; N-alpha-Fmoc-N-beta-trityl-L-asparagine; N-alpha-Fmoc-N-im-methyltrityl-L-histidine; N-alpha-Fmoc-N-im-t-Boc-L-histidine cyclohexylammonium salt; N-alpha-Fmoc-N-im-tosyl-L-histidine; N-alpha-Fmoc-N-im-trityl-L-histidine; N-alpha-Fmoc-5-acetamidomethyl-L-cysteine; N-alpha-Fmoc-5-acetamidomethyl-L-cysteine pentafluorophenyl ester; N-alpha-Fmoc-S-benzyl-L-cysteine; N-alpha-Fmoc-S-p-methoxybenzyl-L-cysteine; N-alpha-Fmoc-S-p-methoxytrityl-L-cysteine; N-alpha-Fmoc-S-t-butyl-L-cysteine; N-alpha-Fmoc-S-t-butyl-L-cysteine pentafluorophenyl ester; N-alpha-Fmoc-S-t-butylthio-L-cysteine; N-alpha-Fmoc-S-t-butylthio-L-cysteine pentafluorophenyl ester; N-alpha-Fmoc-5-trityl-L-cysteine; N-alpha-Fmoc-5-trityl-L-cysteine pentafluorophenyl ester. These and other amino acid reagents for use in solid phase synthesis of peptides are commercially available, for example, from Calbiochem Corporation. Aliphatic carboxylic acids are also available from Sigma-Aldrich Chemical Company.

The peptides may also be produced by a solid phase synthesis using a Boc strategy, wherein a first Boc amino acid is attached to an insoluble support resin via a HF cleavable linker. Deprotection by removal of the Boc group is accomplished by treatment of the Boc-amino acid with TFA. A second Boc amino acid is then coupled utilizing a pre-activated species or in situ activation. After the desired peptide is synthesized, the resin-bound peptide is deprotected and detached from the solid support via cleavage using a strong acid such as HF, TFMSOTf, or TMSOTf. An additive such as a thiol compound is added to protect the peptide from any carbocations generated during cleavage. The following protecting groups are compatible with HF cleavage: Arg(Mts); Cys(4-MeOBzl); His(Z); Arg(Tos); Glu(OBzl); Lys(Cl-Z); Asp(OBzl); Glu(OcHex); Ser(Bzl); Asp(OcHex); His(Bom); Thr(Bzl); Cys(Acm); His(Dnp); Trp(CHO); Cys(4-MeBzl); His(Tos); Tyr(Br-Z); Asp(OtBu); His(Trt). The following protecting groups are compatible with TFMSOTf cleavage: Arg(Mts); His(Bom); Met(O); Asp(OBzl); His(Dnp)); Ser (Bzl); Cys(Acm); His(Tos); Thr(Bzl); Cys(4-MeBzl); His(Z); Trp(CHO); Glu(OBzl); Lys(Cl-Z); Tyr(Br-Z). The following protecting groups are compatible with TMSOTf cleavage: Arg(Mts); Glu(OcHex); Trp(CHO); Arg(Mbs); His (Bom); Trp(Mts); Asp(OBzl); Lys(Cl-Z); Tyr(Br-Z); Asp (OcHex); Met(O); Tyr(Bzl); Cys(Acm); Ser(Bzl); Tyr(Cl-Bzl); His(Bom); Thr(Bzl). Coupling of amino acid carboxylic acids and amines to form peptide amide bonds can be accomplished in a Boc strategy using carbodiimides such as dicyclohexylcarbodiimide (DCC), diisopropylcarbodiimide (DIC), t-butyl methyl- and t-butylethyl-carbodiimides; BOP; PyBroP; PyBOP; HBTU; TBTU; and HATU, all of which reagents require bases for activation and which act by the formation of symmetrical anhydride. Alternatively, carboxylic-carbonate or carboxylic-phosphinic mixed anhydride reagents, prepared by reacting isobutyl- or isopropyl-chloroformate and substituted phosphinic chlorides with the N-alpha-protected amino acid, or N-carboxyanhydrides (NCA's) or Leuchs' anhydride can be used. As with Fmoc chemistry, the N-terminal amine and the C-terminal carboxylic acid group can be chemically modified according to synthetic strategy outline above.

EXAMPLES

The invention will be further explained by the following illustrative examples that are intended to be non-limiting. These examples provide the results from testing of specific peptides that are representative of peptides disclosed in the application. The peptides are listed with any modifications to the N-terminal amino group of the N-terminal amino acid and/or the C-terminal carboxyl group of the C-terminal amino acid on the left- and right-hand sides, respectively, of the amino acid sequence, which is indicated by a Peptide # of the test peptides. Table IX contains the key to the peptide's sequence. Myr- and Ac- are abbreviations of myristoyl and acetyl, respectively, which are covalently bonded in amide bonds to the N-terminal amino acid in the respective peptide amino acid sequences; an —$NH_2$ denotes an amide of ammonia which is covalently bound to the C-terminal end of the peptide amino acid sequence.

Example 1A

Relative Efficacy of Test Peptides in a Mouse Model of Asthma

I. Protocols and Methods

Experiments were designed to test whether or not the MANS peptide and other test peptides related thereto inhibit hypersecretion of mucin in murine airway in vivo. The ovalbumin-sensitized mouse model of allergic inflammation and asthma used in these studies was as described by Singer et al. (2004), supra. As a negative control, a control peptide containing an N-terminal myristoyl group and the same amino acids as MANS peptide but arranged in random order (i.e., the random N-terminal sequence, RNS, myristoyl-peptide 232) was tested alongside the proposed active peptides. BP2 mice, aged 6-8 wks, were immunized subcutaneously twice at weekly intervals with 1 μg of ovalbumin. After 14 days of sensitization, the animals were exposed to aerosolized ovalbumin, which causes a pronounced goblet cell hyperplasia after 72 hours. At the 72 hr time point, the secretagogue, methacholine (60 mM) was delivered using a Buxco system nebulizer providing a fine aerosol for 90 seconds. Fifteen mM prior to the secretagogue challenge, 50 μL of the test peptide, at 3 different concentrations (10 μM, 100 μM, or 140 μM), was administered by intratracheal route. The RNS peptide was tested at the highest dose level only (50 μL of 140 μM solution). The MANS as well as RNS peptide were freely soluble in 120 mM sodium acetate, pH 7. The various controls used in these experiments are tabulated in Table I below. Each experiment was carried out in 6 mice per point, and each set of experiments was repeated 3 times. To test strain-to-strain variations, the above experiment was repeated in Balb/C mice under similar protocol. Both stimulated and unstimulated mucin secretion, in mice treated with 120 mM sodium acetate (data not shown), were identical to saline control. Following the methacholine challenge, the animals were sacrificed and bronchoalveolar lavage (BAL) performed on 6 animals per group for analysis of secreted mucin.

Table I indicates the general protocol for the experiment.

TABLE I

General protocol for methacholine-induced mucin hypersecretion in the presence of test peptide

| Test Group | # mice | Treatment | Peptides | Secretagogue Challenge |
|---|---|---|---|---|
| Saline control | 6 | Endotoxin-free 0.9% NaCl | None | Yes |
| Saline control | 6 | Endotoxin-free 0.9% NaCl | None | No |
| Test peptide | 6 | Endotoxin-free 0.9% NaCl + 140 μM Each test peptide | Each test peptide | Yes |
| Test peptide | 6 | Endotoxin-free 0.9% NaCl + 100 μM Each test peptide | Each test peptide | Yes |
| Test peptide | 6 | Endotoxin-free 0.9% NaCl + 100 μM Each test peptide | Each test peptide | No |
| Test peptide | 6 | Endotoxin-free 0.9% NaCl + 10 μM Each test peptide | Each test peptide | Yes |
| Test peptide | 6 | Endotoxin-free 0.9% NaCl + 10 μM Each test peptide | Each test peptide | No |
| Negative (control) peptide (RNS) | 6 | Endotoxin-free 0.9% NaCl + 140 μM RNS peptide | RNS | Yes |

II. Analyses of BAL Fluid

Mice were sacrificed by cervical dislocation, followed by rapid exposure of the trachea and insertion of a cannula through a small incision. Bronchoalveolar lavage (BAL) fluid was collected with 0.5 ml followed by 3×1 ml PBS containing PMSF (5 mM), EDTA (5 mM), and DTT (5 mM). BAL fluid was separated into cell-free and cell fractions via brief centrifugation prior to any analyses being performed. The cell-free supernatants were analyzed for the presence of mucin via an ELISA method using anti-mucin antibodies shown to react with mouse mucin. Specifically, a mouse anti-MUC5AC antibody that recognizes the carbohydrate portion of secreted mucin was used in these assays. Data generated from each BAL sample were normalized to total protein as determined by Bradford assay. Mucin content was expressed as the value obtained with the anti-mucin antibody minus that obtained with the non-immune control antibody. All ELISA data were statistically examined using a one-way ANOVA. The experimental data were considered significantly different from control when the p<0.05.

Tables II, III, IV, V and VI below summarize the effect of various peptides on mucin secretion in Balb/C mice and BP2 mice. As shown in Table II, at 100 μM of the various test peptides, mucin secretion was between 8% and 56% of that of the control (i.e., no peptide).

TABLE II

Mucin Secretion in a Murine Model of
Asthma (Experiments in Balb/C Mice)

| Peptide (peptide #/identifier) | % control | Mean error |
|---|---|---|
| No peptide | 100 | 4.2 |
| MANS, myr-peptide 1 | 33.8 | 5.8 |
| RNS, myr-peptide 232 | 96 | 5.2 |
| myr-peptide 79 | 50 | 10.8 |
| myr-peptide 233 | 21 | 14.2 |
| myr-peptide 234 | 8 | 4.2 |
| myr-peptide 235 | 13 | 3.3 |
| peptide 79 | 10 | 3.3 |
| myr-peptide 234-$NH_2$ | 27.8 | 1.6 |
| myr-peptide 106 | 33.6 | 5.8 |
| peptide 106) | 33.8 | 3.3 |
| myr-peptide 106-$NH_2$ | 29.3 | 4.2 |
| myr-peptide 236-$NH_2$ | 51 | 2.0 |
| Ac-peptide 106 | 21.5 | 18.3 |
| myr-peptide 137 | 55 | 4.2 |
| myr-peptide 137-$NH_2$ | 56 | 3.3 |

All peptides tested at 100 μM. All values significant vs. control (p < 0.001) except myr-peptide 137 (p < 0.01) and RNS.

TABLE III

Mucin Secretion in a Murine Model of
Asthma (Experiments in Balb/C Mice)

| Peptide (peptide #/identifier) | % control | Mean error |
|---|---|---|
| No peptide | 100 | 8.1 |
| MANS, myr-peptide 1 | 40 | 11.8 |
| RNS, myr-peptide 232 | 81** | 2.8 |
| myr-peptide 11 | 54 | 5.1 |
| myr-peptide 37 | 35** | 11.8 |
| myr-peptide 79 | 48 | 10.3 |
| myr-peptide 15 | 38* | 10.6 |
| myr-peptide 45 | 35** | 10.3 |
| myr-peptide 91 | 68 | 14.7 |
| myr-peptide 153 | 50 | 7.3 |

All peptides tested at 100 μM.
*= values significant vs. control (p < 0.05);
**= values significant vs. control (p < 0.01).

TABLE IV

Mucin Secretion in a Murine Model of
Asthma (Experiments in Balb/C Mice)

| Peptide (peptide #/identifier) | % of control | Mean error |
|---|---|---|
| No peptide | 100 | 5.3 |
| MANS, myr-peptide 1 (100 μM) | 29** | 4.2 |
| RNS, myr-peptide 232 (100 μM) | 108 | 8.5 |
| peptide 237 (10 μM) | 67*+ | 8.5 |
| peptide 237 (100 μM) | 8** | 3.8 |
| myr-peptide 106 (10 μM) | 74*+ | 10.6 |

TABLE IV-continued

Mucin Secretion in a Murine Model of
Asthma (Experiments in Balb/C Mice)

| Peptide (peptide #/identifier) | % of control | Mean error |
|---|---|---|
| myr-peptide 106 (100 μM) | 24** | 9.6 |
| peptide 106 (10 μM) | 64* | 4.2 |
| peptide 106 (100 μM) | 40** | 9.6 |
| myr-peptide 106-$NH_2$ (10 μM) | 67*+ | 4.2 |
| myr-peptide 106-$NH_2$ (100 μM) | 17** | 5.3 |

*= values significant vs. control (p < 0.05);
**= values significant vs. control (p < 0.01).
+= value significant vs. 100 μM treatment (p < 0.05).

TABLE V

Mucin Secretion in a Murine Model of Asthma
(Experiment in BP2 Mice) (% of Control)

| | Mucin Secretion (% of Control) | | |
|---|---|---|---|
| Peptide (Conc.) | 10 μM | 100 μM | 140 μM |
| MANS peptide | 35 | 12 | 8 |
| RNS peptide | — | 100 | 100 |

Experiments were designed to determine the duration of action of test peptides in a murine model of asthma. As described in Method 1A, Balb/C mice were immunized with ovalbumin. After 14 days, the animals were challenged with aerosolized ovalbumin. After 72 hours the secretagogue, methacholine was delivered by aerosolization. The test peptides (50 L of 100 M solution) were administered by intratracheal route 30 mM, 60 mM, or 120 min prior to methacholine challenge. The animals were sacrificed and BAL performed for analysis of secreted mucin The results of this experiment are given in Table VI.

TABLE VI

Duration of Action of Test Peptides in a Murine
(Experiments in Balb/C Mice) (% of Control)

| Peptide | 30 min | 60 min | 120 min |
|---|---|---|---|
| Control | 100 | 100 | 100 |
| MANS, myr-peptide 1 | 7 | 44 | 50 |
| RNS, myr-peptide 232 | 100 | 100 | 100 |
| Ac-peptide 106 | 21 | 72 | 70 |
| peptide 106 | 23 | 48 | 57 |

An alternative mouse test model and method of quantitatively determining mucin in mouse lungs is useful to evaluate the activity of peptides of the present invention. This method is described by Evans et al (Am. J. Respir. Cell Mol. Biol. Vol. 31, pp 382-394, 2004). Briefly, Balb/c female mice (5-8 weeks old, 20-25 g each) are sensitized weekly for four weeks by intraperitoneal (i.p.) injection of 100 μL solution containing 2.2 mg of alum salt and 20 vig of ovalbumin in normal saline. Seven days after the last i.p. injection, the mice are challenged by aerosol administration over 30 minutes of a 2.5% solution of ovalbumin dissolved in normal saline. The aerosol is generated with AeroMist CA-209 compressed air nebulizer (CIS-US, Inc., Bedford, Mass.).

Three days post ovalbumin challenge, 50 μL of the test peptide is delivered in each nostril of the mouse in 10 μL aliquots over 2-3 minutes. Fifteen minutes later the mice are treated with aerosolized 100 mM ATP solution over 5 minutes. After 20 minutes, the mice are anesthetized by i.p. injection of a mixture of ketamine, xylazine, and acepromazine and the lungs are perfused with saline via the right cardiac ventricle to clear blood from the pulmonary tissues. Under deep anesthesia, animals are tracheostomized using a 20 gauge blunt tip cannula and sacrificed by exsanguination via the abdominal aorta. Fixative (4% paraformaldehyde in 0.1 M phosphate buffer, pH 7.0) is infused intratracheally at 10-15 cm pressure and the lungs are fixed in situ for 30 minutes, removed from the thoracic cavity and fixed overnight at 4° C. Lungs are embedded in paraffin and cut into 6 μm sections.

For fluorescent labeling of mucin, tissues are stained using a periodic acid fluorescent Schiff (PAFS) staining procedure. Tissues are first oxidized in 1% periodic acid (10 min), rinsed, treated with acriflavine fluorescent Schiff s reagent (0.5% acriflavine HCl wt/vol, 1% sodium metabisulfite wt/vol, 0.01 N HCl) for 20 min, rinsed in double deionized H2O, and rinsed 2×5 min in acid alcohol (0.1 N HCl in 70% ethanol). Slides are dehydrated in graded ethanol solutions and allowed to air dry in the dark. Once dry, PAFS-stained slides are coverslipped with Canada balsam mounting medium (50% Canada balsam resin, 50% methyl salicylate; Fisher Chemicals).

For the quantitation of mucin, PAFS-stained slides are examined under the 40× objective. Images of 10 fields from the axial bronchi are captured, and camera settings are managed using MagnaFire 2.1 (Optronics). PAFS imaging is performed by exciting specimens using a dual excitation filter (500 nm and 573 nm peaks) and observing specimens using a dual emission filter with peaks at 531 nm (green) and 628 nm (red). For each field, an image is first generated using only the red acquisition channel on the camera (590 ms exposure). The same image was then recaptured using both the red and green channels on the camera (590 ms red, 450 ms green). For morphometric analysis, the volume density and fluorescence intensity of mucin staining are then measured using ImagePro Plus. Volume density of mucin staining in the airway epithelium is calculated stereologically. Briefly, the ratio of surface area of staining to total surface area of the epithelium is divided by a boundary length measurement, which is a product of the total epithelial surface area, the basement membrane length, and the geometric constant 4/π. As a result, data is presented as the volume of intracellular mucin contents per surface area of the basement membrane. The mucin secretion is expressed as a fraction of total epithelial content.

Example 1B

Effect of Aerosolized Ac-peptide 106 Peptide Administration on Mucin Hypersecretion in a Mouse Model with Goblet Cell Metaplasia and Airway Obstruction The efficacy of aerosolized Ac-peptide 106 on mucin hypersecretion in a mouse model of asthma was determined at two concentrations. Briefly, 5- to 8 week old BALB/c mice were immunized weekly as described above in Example 1A for 3 weeks with ovalbumin. On Day 28 the mice were challenged with aerosolized 2.5% ovalbumin in normal saline for 30 minutes. Three days after ovalbumin challenge, each group of mice (n=2) was administered an aerosolized isotonic solution of Ac-peptide 106 at 10 mM or 30 mM for 1 hour with an AeroMist CA-209 nebulizer. The mass median aerodynamic diameter of the aerosol particles was 1.49 um (range 0.4 to 4.7 um). Given these concentrations of Ac-peptide 106 and this particle size, the calculated pulmonary deposition of Ac-peptide 106 was 0.38 mg/kg body weight and 1.1 mg/kg body weight, respectively.

Ac-peptide 106 administration was immediately followed by aerosol administration of the secretagogue adenosine triphosphate (ATP) (100 mM in saline) for 5 minutes. The mice were sacrificed, and the lungs were harvested within 20 minutes. The lungs were rinsed with saline, fixed with paraformaldehyde, embedded in paraffin, and sectioned. The sections were quantitatively analyzed for the presence of mucin by quantitative immunohistochemistry according to the method of Evans et al. (Am. J. Respir. Cell Mol. Biol. Vol. 31, pp 382-394, 2004). The results indicate that Ac-peptide 106 was effective as an inhibitor of ATP-induced mucin hypersecretion by 30 to 67% at 0.38 and 1.1 mg/kg body weight, respectively.

Example 2

Evaluation of Qualitative Solubility of Test Peptides in 0.5 Normal Saline

Various test peptides (1 to 5 mg each) were weighed out accurately in individual 2 mL screw cap glass vials and aliquots of 25 μL of 0.5 N saline, pH 6.5, were added at 25° C. and ambient pressure. The solubility was evaluated visually. If the test peptide dissolves completely with the first aliquot of saline, its solubility was calculated and designated as more than the calculated amount. Thus, if 3.5 mg of a test peptide dissolves instantly with the first 25 μL aliquot of 0.5 N saline, its solubility is stated as >140 mg/mL. Similarly, if 1.7 mg of a test peptide fails to dissolve in 1.7 mL of 0.5 N saline, its solubility is stated as <1.0 mg/mL. The results of the evaluation of solubility of various test peptides are listed in Table VII.

The solubility of various peptides in half-normal saline can also be determined by one of the following two semi-quantitative methods, Method 1 and Method 2. Method 1 can be used for those peptides whose solubility in half-normal saline will be less than about 10 mg/mL, while Method 2 can be used for peptides that will be soluble in half-normal saline at more than about 30 mg/mL.

Method 1

Each peptide is dissolved in dimethylsulfoxide (DMSO) at a concentration of 1 mg/mL. An aliquot of this solution is diluted five fold with half-normal saline to provide 0.2 mg/mL solution. The latter peptide solution is subjected to HPLC analysis using C18/5 micron column. The elution buffers consist of 0.1% trifluoroacetic acid (TFA) in water (buffer A) and 0.1% TFA in 100% acetonitrile (buffer B). The peptide is eluted with a gradient from 5% B to 45% B during about 20 min. The area under the curve (AUC) for each peptide peak can be thus determined. This AUC value can be used as a standard (AUC-Std) to determine the concentration of each corresponding peptide in the supernatant of a saturated solution.

Saturated solution of each peptide can be prepared by adding sufficient quantity of a peptide to 1 mL of half-normal saline until a cloudy suspension is obtained. The latter is then centrifuged at 10,000×g for about 10 min. The supernatant is then subjected to HPLC analysis. The supernatant is further diluted with half-normal saline, if necessary, prior to HPLC analysis. The AUC (AUC-Sat) obtained from this analysis is used to determine the concentration of the peptide in the saturated solution by the following formula:

Concentration of the peptide in saturated solution=AUC-Std×0.2/AUC-Sat.

Method 2

This method can provide an estimate of peptide solubility in half-normal saline. The method consists of adding a weighed quantity (denoted as "xx" milligrams) of a peptide to dissolve in 1 mL of half-normal saline. The results are presented as >xx mg/mL, where xx is the amount of peptide added to the half-normal saline.

TABLE VII

Peptide Solubility at 20° C. in 0.5 N saline, pH 6.5

| Sequence No. | Solubility in 0.5 N Saline (mg/mL) |
|---|---|
| myr-peptide 1 | <5.0 |
| Ac-peptide 1 | >125 |
| myr-peptide 232 | >15 |
| myr-peptide 11 | >2.0 |
| myr-peptide 37 | >2.0 |
| myr-peptide 79 | >2.0 |
| myr-peptide 238 | >2.0 |
| myr-peptide 233 | >3.0 |
| myr-peptide 234 | >3.0 |
| myr-peptide 235 | >60 |
| peptide 79 | >60 |
| myr-peptide 79-NH$_2$ | <1.0 |
| myr-peptide 237 | <1.0 |
| myr-peptide 237-NH$_2$ | <1.0 |
| peptide 237 | >80 |
| myr-peptide 234-NH$_2$ | <2.0 |
| Ac-peptide 79-NH$_2$ | >60 |
| Ac-peptide 79 | >100 |
| Ac-peptide 239 | >50 |
| Ac-peptide 240 | N/A |
| Ac-peptide 241 | >50 |
| myr-peptide 106 | >10 |
| peptide 106 | >70 |
| myr-peptide 106-NH$_2$ | <10 |
| myr-peptide 236 | <10 |
| myr-peptide 236-NH$_2$ | <10 |
| peptide 106-NH$_2$ | >100 |
| Ac-peptide 106 | >100 |
| cyclic-peptide 106 | >150 |
| Ac-peptide 242 | >100 |
| Ac-peptide 243 | >50 |
| Ac-peptide 236 | >80 |
| Ac-peptide 244 | >120 |
| Ac-peptide 245 | >100 |
| Ac-peptide 247 | >100 |
| Ac-peptide 248 | >100 |
| Ac-peptide 249 | <1 |
| myr-peptide 121 | <1.0 |
| Ac-peptide 121 | >20 |
| myr-peptide 137 | <1.0 |
| myr-peptide 137-NH$_2$ | N/A |
| Ac-peptide 250 | N/A |
| Ac-peptide 137 | >200 |
| myr-peptide 15 | >80 |
| myr-peptide 45 | >80 |
| myr-peptide 91 | <20 |
| myr-peptide 153 | <10 |
| myr-peptide 143 | <1.0 |
| Ac-peptide 143 | >230 |
| myr-peptide 179 | <1.0 |
| Ac-peptide 179 | >150 |
| myr-peptide 219 | <1.0 |
| Ac-peptide 219 | >200 |
| Ac-peptide 219-NH$_2$ | >200 |
| Ac-peptide 251 | >200 |
| Ac-peptide 93-NH$_2$ | >90 |
| Ac-peptide 108-NH$_2$ | >150 |
| Ac-peptide 124-NH$_2$ | >100 |
| Ac-peptide 141-NH$_2$ | >200 |
| Ac-peptide 159-NH$_2$ | >200 |
| Ac-peptide 246 | <30 |
| Ac-peptide 252 | <30 |

Example 3

Stability of Test Peptides in Biological Fluids

Various test peptides in human plasma, human BALF, and CF patient mucus were analyzed to determine the susceptability of the test peptide to proteolysis in the biological fluids. In addition, first order kinetic analyses were performed on samples that exhibited concentration decays in order to determine the test peptide half-life. The samples were analyzed either on the same day as received or stored at −20° C. and analyzed within the following two days.

I. Collection and Processing of Biological Fluids

A. Human Plasma:

Fresh human blood samples were collected in citrate buffered vacuutrainers (in absence of EDTA or heparin). Red blood cells (RBC) were removed by centrifugation of the blood at 4000×g for 10 min at 4° C. Plasma aliquots (0.9 mL) were then spiked with 0.1 mL of 0.5 mg/mL solution of the test peptide in 75 mM sodium acetate buffer at pH 7.0 and incubated in a water bath maintained at 37° C. Duplicate aliquots of 10 µL were withdrawn at 5, 15, 30, 60, and 180 minutes intervals and immediately "quenched" with 990 µL of a solution consisting of 50% acetonitrile+50% water containing 0.2% formic acid. The samples were then subjected to liquid chromatography-mass spectrometry (LCMS) analysis.

B. Human BAL Fluid:

Samples of BALF collected from COPD patients were obtained and frozen. The BALF samples were thawed, mixed together and centrifuged at 10,000×g for 10 min at 4-8° C. The supernatant (0.9 mL) was spiked with 0.1 mL of 0.5 mg/mL solution of the peptide in 75 mM sodium acetate buffer at pH 7.0 and processed and analyzed as described above.

C. Human CF Mucus:

The frozen mucus (sputum) from a CF patient was thawed and mixed with 2 volumes of 75 mM sodium acetate buffer, pH 7 with the help of a glass tissue grinder, centrifuged at 10,000×g for 10 min at 4-8° C. The pellet was re-suspended in 1 volume of the acetate buffer and centrifuged. The two supernatants were combined and used as follows. The supernatant (450 µL) was spiked with 50 µL of 0.5 mg/mL solution of the peptide in 75 mM sodium acetate buffer at pH 7.0 and processed and analyzed as described above.

II. Concentration Analysis

All samples were analyzed using LC/MS/MS (MDS/SCIEX, API 4000 Model). Chromatography was performed using a Phenomenex Luna C18 column, while mass spectrometry was performed using positive ion electrospray ionization.

A. Analysis of peptides Ac-PEPTIDE 79-NH$_2$, Ac-PEPTIDE 106 in Human Plasma and BALF and analysis of peptides myr-PEPTIDE 106, PEPTIDE 106, PEPTIDE 106-NH$_2$, Ac-PEPTIDE 106, and cyc-PEPTIDE 106 (a cyclic peptide) in Human Plasma and Human CF Mucus Calibration standards were analyzed by LCMS at concentrations of 0.100 µg/mL, 1.00 µg/mL, 10.0 µg/mL, and 100 µg/mL for each peptide, with the exception of the calibration standards for peptides myr-PEPTIDE 106, PEPTIDE 106, PEPTIDE 106-NH$_2$, PEPTIDE 106, and cyclic peptide, cyc-PEPTIDE 106, in human mucus, which were analyzed at concentrations of 0.100 µg/mL, 1.00 µg/mL, 10.0 µg/mL, and 75 µg/mL. Standards were prepared in 1% human BALF, plasma, or mucus in 50/50 water/acetonitrile mixture containing 0.2% formic acid. The instrument response values for each set of standards were fit using a 1/(concentration)$^2$ linear least-squares line. Sample concentrations were calculated using the slope and intercept of this line. Concentrations outside of the calibration range were determined by extrapolating the calibration curve.

B. Analysis of peptides myr-PEPTIDE 234-NH$_2$, myr-PEPTIDE 234, PEPTIDE 106, and myr-PEPTIDE 106 in human plasma and BALF Duplicate calibration standards were analyzed at a concentration of 50 μg/mL for each peptide. The instrument response values for each set of standards were fit through an intercept of 0 using an unweighted, linear least-squares line. Sample concentrations were calculated using the slope and intercept of this line.

C. Analysis of Peptides PEPTIDE 237, myr-PEPTIDE 106-NH$_2$, myr-PEPTIDE 236, and myr-PEPTIDE 236-NH$_2$ in Human Plasma and BALF For the analysis of peptide concentration in plasma, duplicate calibration standards were analyzed at a concentration of 25 μg/mL and 50 μg/mL for each peptide. The instrument response values for each set of standards were fit through an intercept of 0 using an unweighted, linear least-squares line. Sample concentrations were calculated using the slope and intercept of this line. Concentrations outside of the calibration range were determined by extrapolating the calibration curve.

For the analysis of peptide concentration in BALF samples, one 50 μg/mL calibration standard prepared in a mixture of BALF, water, acetonitrile, and formic acid was analyzed with each sample set.

III. Kinetic Profiles

First order kinetic profiles were determined using the software program Watson for all samples that exhibited a noticeable decay in concentration. Watson fits the log transformed data with a least-squares line to determine parameters such as $C_{max}$ (maximum concentration), intercept, rate constant, slope, and $T_{1/2}$ (half-life). The resulting kinetic parameters were based on the linear fit, not the actual concentration values.

Time-zero calibration standards in solution were not included as part of the kinetic profiles. However, true first order kinetics do not require inclusion of time-zero data points to accurately describe changes in concentration as a function of time.

The half-life of the test peptides in human plasma (Plasma $t_{1/2}$), human BALF (BALF $t_{1/2}$), and human CF mucus (Mucus $t_{1/2}$) are listed in the Table VIII.

The peptide, myr-peptide 236, is myristoyl-PEPTIDE 236. All other peptides used in the experiment are described above.

Example 4

Efficacy of MANS Peptide on Mucus Secretion in Upper Respiratory Tract of Primates The purpose of the experiment was to determine the ability of MANS peptide to inhibit mucus secretion in the upper respiratory tract of healthy adult rhesus monkeys. The test used is a standard method for evaluation of nasal secretory activity, and non-human primates typically provide a good correlation to activity in man.

Methods

A total of 17 healthy young adult male rhesus monkeys without any prior history of rhinitis were used for the experiment. None of the monkeys had rhinitis before or after the study. The nasal mucus secretion of each monkey was measured in its left nostril prior to any treatment. This value is considered 100% mucus secretion. The monkeys were then randomly divided into the following 4 groups:

Group 1: Normal saline, control (n=3);
Group 2: Sodium acetate, solvent control (n=4);
Group 3: RNS peptide, negative control (n=5); and
Group 4: MANS peptide, test peptide (n=5).

Saline was placed in the left nostril of all 17 animals prior to any treatment. The right nostrils were treated with 2.0 mL of either saline, sodium acetate, RNS peptide or the MANS peptide. Thus, each animal had its own internal control. Nasal lavage was performed on both nostrils of each animal 1 hour after the treatment with the test articles. All lavages were immediately frozen at −80° C. and analyzed for mucus content by ELISA.

A. Test Articles:

Normal saline, filter sterilized; Sodium acetate, 150 μM, filter sterilized 3. RNS Peptide—140 μM solution in 150 μM filter sterilized sodium acetate and MANS Peptide—140 μM solution in 150 μM filter sterilized sodium acetate B. Test Animals:

Rhesus monkeys; Number of animals: 17; Sex: all healthy males; Age: 3 to 4 years; Body weight: 4 to 7 Kg., Average 5.03 Kg.; Acclimatization Period: 7 days; Identification Method: Unique tattoo with a 5 digit II) number. History: All animals were used for a vaccine study for immunization

TABLE VIII

| Peptide identifier [#] | Plasma $t_{1/2}$ (hours) (1st exp.) | Plasma $t_{1/2}$ (hours) (2nd exp.) | BALF $t_{1/2}$ (hours) (1st exp.) | BALF $t_{1/2}$ (hours) (2nd exp.) | Mucus $t_{1/2}$ (hours) (1st exp.) | Mucus $t_{1/2}$ (hours) (2nd exp.) |
|---|---|---|---|---|---|---|
| myr-peptide 234-NH$_2$ | 3.82 | — | 1.70 | — | — | — |
| myr-peptide 234 | * | — | 1.08 | — | — | — |
| peptide 106 | 0.28 | 0.15 | 1.88 | — | 0.23 | 0.37 |
| myr-peptide 106 | 1.23 | 0.90 | 1.03 | — | 9.53 | 3.00 |
| peptide 237 | 0.49 | — | * | * | — | — |
| myr-peptide 106-NH$_2$ | * | — | 10.52 | 12.81 | — | — |
| myr-peptide 236 | 0.72 | — | 3.55 | 2.94 | — | — |
| myr-peptide 236-NH$_2$ | * | — | 4.16 | 4.08 | — | — |
| Ac-peptide 79-NH$_2$ | 2.64 | — | * | — | — | — |
| peptide 106-NH$_2$ | 0.30 | 0.13 | 4.00 | — | 0.08 | 0.13 |
| Ac-peptide 106 | * | 0.03 | 1.89 | — | 0.55 | 0.47 |
| cyclic-peptide 106 | — | 1.04 | — | — | 1.10 | 2.00 |

[#] myr and Ac are respectively myristoyl and acetyl groups covalently bonded to the peptide at the N-terminal amine site; —NH$_2$ is a covalently bonded amide at the C-terminal carboxylic group of the peptide; seq no. and cyc are abbreviations for sequence number and cyclic, respectively.
—: Experiment not performed.
* Not enough data from experiment to calculate half-life.

against meningitis 12-24 months prior to this test. All animals also received the routine immunization against measles and tetanus during their infancy.

C. Animal Management:

Husbandry: Conditions conformed to Standard Operating Procedures, which are based on the "Guide for the Care and Use of Laboratory Animals". Food: Standard rhesus monkey diet was provided daily. Water: Freely available, municipal water was delivered through an automatic watering system. Housing: Animals were housed individually in approved stainless steel cages identified by a card indicating the animal numbers, test code, sex, animal code. Environmental: The room temperature was monitored daily. The temperature range for the room was within a range of 20-26° C. The humidity range for the room, monitored daily, was 40-70%. The light cycle was controlled using an automatic timer (12 hours light, 12 hours dark.) Personnel: Associates involved were appropriately qualified and trained for primates.

Results

The results provide data that the RNS peptide, sodium acetate buffer, or normal saline did not have any effect on mucus secretion whereas mucus secretion was inhibited by almost 75% with MANS peptide.

Example 5

Tissue Culture Method for Determination of Secreted Mucin in Human Bronchial Epithelial Cells HBE1 is a papilloma virus-transformed human bronchial epithelial cell line capable of mucin secretion when cultured in air/liquid interface. HBE1 cells were cultured in the air/liquid interface as described previously (Li et al, J. Biol. Chem., volume 276, pp 40982-40990, 2001). Briefly, HBE1 cells were cultured in air/liquid interface by seeding an appropriate number of cells in 12-well Transwell clear culture inserts (Costar, Cambridge, Mass.) that were thinly coated with rat tail collagen, type I (Collaborative Biomedical, Bedford, Mass.). Cells were initially cultured submerged in medium in a humidified 95% air, 5% $CO_2$ environment for 5-7 days until nearly confluent. At that time, the air/liquid interface was created by removing the apical medium and feeding cells basalaterally. Medium was renewed daily thereafter. Cells were cultured for an additional 14 days to allow full differentiation. The accumulated mucin at the apical surface of the cells was removed by washing with phosphate-buffered saline, pH 7.2. To collect the baseline mucin secretion, cells were incubated for 30 min with medium alone and secreted mucin in the apical medium was collected, and quantitated by ELISA. To determine the mucin hypersecretion induced by a mucin secretagogue, cells were exposed to medium containing 0.5 µM phorbol myristate acetate, (PMA) for 30 min. and mucin was collected and quantitated by ELISA. In order to determine the inhibition of PMA-induced mucin hypersecretion by a test peptide, cells were pre-incubated with medium containing 25 or 50 µM test peptide for 15 min followed by 30 min incubation with 0.5 µM PMA. Six wells were used for each test peptides and for each control. Secreted mucin in the apical medium was collected and quantitated by sandwich ELISA method using alkaline phosphatase-conjugated mucin (MUC5A) specific antibody (Zymed Laboratories, San Francisco, Calif.).

Treatment of HBE1 cells with 0.5 µM PMA resulted in a 20% increase in mucin secretion. This PMA-induced increase in mucin secretion was 100% blocked by pretreatment with 25 µM MANS peptide or with 25 µM Ac-peptide no: 106. Ac-peptide no: 219 at 25 µM not only inhibited 100% of PMA-induced mucin secretion, but also inhibited mucin secretion to a level 20% below the unstimulated medium control. Ac-peptide no: 251 had a minimal 6% inhibitory effect on PMA-induced increase in mucin secretion.

Table IX contains a listing of peptides of this invention and their respective amino acid sequences and corresponding SEQ ID NOS.

TABLE IX

Peptides and Amino Acid Sequences

| Peptide No. | Sequence | Seqence ID No. |
|---|---|---|
| peptide 1 | GAQFSKTAAKGEAAAERPGEAAVA | SEQ ID NO. 1 |
| peptide 2 | GAQFSKTAAKGEAAAERPGEAAV | SEQ ID NO. 2 |
| peptide 3 | AQFSKTAAKGEAAAERPGEAAVA | SEQ ID NO. 3 |
| peptide 4 | GAQFSKTAAKGEAAAERPGEAA | SEQ ID NO. 4 |
| peptide 5 | AQFSKTAAKGEAAAERPGEAAV | SEQ ID NO. 5 |
| peptide 6 | QFSKTAAKGEAAAERPGEAAVA | SEQ ID NO. 6 |
| peptide 7 | GAQFSKTAAKGEAAAERPGEA | SEQ ID NO. 7 |
| peptide 8 | AQFSKTAAKGEAAAERPGEAA | SEQ ID NO. 8 |
| peptide 9 | QFSKTAAKGEAAAERPGEAAV | SEQ ID NO. 9 |
| peptide 10 | FSKTAAKGEAAAERPGEAAVA | SEQ ID NO. 10 |
| peptide 11 | GAQFSKTAAKGEAAAERPGE | SEQ ID NO. 11 |
| peptide 12 | AQFSKTAAKGEAAAERPGEA | SEQ ID NO. 12 |
| peptide 13 | QFSKTAAKGEAAAERPGEAA | SEQ ID NO. 13 |
| peptide 14 | FSKTAAKGEAAAERPGEAAV | SEQ ID NO. 14 |
| peptide 15 | SKTAAKGEAAAERPGEAAVA | SEQ ID NO. 15 |
| peptide 16 | GAQFSKTAAKGEAAAERPG | SEQ ID NO. 16 |
| peptide 17 | AQFSKTAAKGEAAAERPGE | SEQ ID NO. 17 |
| peptide 18 | QFSKTAAKGEAAAERPGEA | SEQ ID NO. 18 |
| peptide 19 | FSKTAAKGEAAAERPGEAA | SEQ ID NO. 19 |
| peptide 20 | SKTAAKGEAAAERPGEAAV | SEQ ID NO. 20 |
| peptide 21 | KTAAKGEAAAERPGEAAVA | SEQ ID NO. 21 |
| peptide 22 | GAQFSKTAAKGEAAAERP | SEQ ID NO. 22 |
| peptide 23 | AQFSKTAAKGEAAAERPG | SEQ ID NO. 23 |
| peptide 24 | QFSKTAAKGEAAAERPGE | SEQ ID NO. 24 |
| peptide 25 | FSKTAAKGEAAAERPGEA | SEQ ID NO. 25 |
| peptide 26 | SKTAAKGEAAAERPGEAA | SEQ ID NO. 26 |
| peptide 27 | KTAAKGEAAAERPGEAAV | SEQ ID NO. 27 |
| peptide 28 | TAAKGEAAAERPGEAAVA | SEQ ID NO. 28 |
| peptide 29 | GAQFSKTAAKGEAAAER | SEQ ID NO. 29 |
| peptide 30 | AQFSKTAAKGEAAAERP | SEQ ID NO. 30 |
| peptide 31 | QFSKTAAKGEAAAERPG | SEQ ID NO. 31 |
| peptide 32 | FSKTAAKGEAAAERPGE | SEQ ID NO. 32 |
| peptide 33 | SKTAAKGEAAAERPGEA | SEQ ID NO. 33 |

TABLE IX-continued

Peptides and Amino Acid Sequences

| Peptide No. | Sequence | Seqence ID No. |
|---|---|---|
| peptide 34 | KTAAKGEAAAERPGEAA | SEQ ID NO. 34 |
| peptide 35 | TAAKGEAAAERPGEAAV | SEQ ID NO. 35 |
| peptide 36 | AAKGEAAAERPGEAAVA | SEQ ID NO. 36 |
| peptide 37 | GAQFSKTAAKGEAAAE | SEQ ID NO. 37 |
| peptide 38 | AQFSKTAAKGEAAAER | SEQ ID NO. 38 |
| peptide 39 | QFSKTAAKGEAAAERP | SEQ ID NO. 39 |
| peptide 40 | FSKTAAKGEAAAERPG | SEQ ID NO. 40 |
| peptide 41 | SKTAAKGEAAAERPGE | SEQ ID NO. 41 |
| peptide 42 | KTAAKGEAAAERPGEA | SEQ ID NO. 42 |
| peptide 43 | TAAKGEAAAERPGEAA | SEQ ID NO. 43 |
| peptide 44 | AAKGEAAAERPGEAAV | SEQ ID NO. 44 |
| peptide 45 | AKGEAAAERPGEAAVA | SEQ ID NO. 45 |
| peptide 46 | GAQFSKTAAKGEAAA | SEQ ID NO. 46 |
| peptide 47 | AQFSKTAAKGEAAAE | SEQ ID NO. 47 |
| peptide 48 | QFSKTAAKGEAAAER | SEQ ID NO. 48 |
| peptide 49 | FSKTAAKGEAAAERP | SEQ ID NO. 49 |
| peptide 50 | SKTAAKGEAAAERPG | SEQ ID NO. 50 |
| peptide 51 | KTAAKGEAAAERPGE | SEQ ID NO. 51 |
| peptide 52 | TAAKGEAAAERPGEA | SEQ ID NO. 52 |
| peptide 53 | AAKGEAAAERPGEAA | SEQ ID NO. 53 |
| peptide 54 | AKGEAAAERPGEAAV | SEQ ID NO. 54 |
| peptide 55 | KGEAAAERPGEAAVA | SEQ ID NO. 55 |
| peptide 56 | GAQFSKTAAKGEAA | SEQ ID NO. 56 |
| peptide 57 | AQFSKTAAKGEAAA | SEQ ID NO. 57 |
| peptide 58 | QFSKTAAKGEAAAE | SEQ ID NO. 58 |
| peptide 59 | FSKTAAKGEAAAER | SEQ ID NO. 59 |
| peptide 60 | SKTAAKGEAAAERP | SEQ ID NO. 60 |
| peptide 61 | KTAAKGEAAAERPG | SEQ ID NO. 61 |
| peptide 62 | TAAKGEAAAERPGE | SEQ ID NO. 62 |
| peptide 63 | AAKGEAAAERPGEA | SEQ ID NO. 63 |
| peptide 64 | AKGEAAAERPGEAA | SEQ ID NO. 64 |
| peptide 65 | KGEAAAERPGEAAV | SEQ ID NO. 65 |
| peptide 66 | GEAAAERPGEAAVA | SEQ ID NO. 66 |
| peptide 67 | GAQFSKTAAKGEA | SEQ ID NO. 67 |
| peptide 68 | AQFSKTAAKGEAA | SEQ ID NO. 68 |
| peptide 69 | QFSKTAAKGEAAA | SEQ ID NO. 69 |
| peptide 70 | FSKTAAKGEAAAE | SEQ ID NO. 70 |
| peptide 71 | SKTAAKGEAAAER | SEQ ID NO. 71 |
| peptide 72 | KTAAKGEAAAERP | SEQ ID NO. 72 |
| peptide 73 | TAAKGEAAAERPG | SEQ ID NO. 73 |
| peptide 74 | AAKGEAAAERPGE | SEQ ID NO. 74 |
| peptide 75 | AKGEAAAERPGEA | SEQ ID NO. 75 |
| peptide 76 | KGEAAAERPGEAA | SEQ ID NO. 76 |
| peptide 77 | GEAAAERPGEAAV | SEQ ID NO. 77 |
| peptide 78 | EAAAERPGEAAVA | SEQ ID NO. 78 |
| peptide 79 | GAQFSKTAAKGE | SEQ ID NO. 79 |
| peptide 80 | AQFSKTAAKGEA | SEQ ID NO. 80 |
| peptide 81 | QFSKTAAKGEAA | SEQ ID NO. 81 |
| peptide 82 | FSKTAAKGEAAA | SEQ ID NO. 82 |
| peptide 83 | SKTAAKGEAAAE | SEQ ID NO. 83 |
| peptide 84 | KTAAKGEAAAER | SEQ ID NO. 84 |
| peptide 85 | TAAKGEAAAERP | SEQ ID NO. 85 |
| peptide 86 | AAKGEAAAERPG | SEQ ID NO. 86 |
| peptide 87 | AKGEAAAERPGE | SEQ ID NO. 87 |
| peptide 88 | KGEAAAERPGEA | SEQ ID NO. 88 |
| peptide 89 | GEAAAERPGEAA | SEQ ID NO. 89 |
| peptide 90 | EAAAERPGEAAV | SEQ ID NO. 90 |
| peptide 91 | AAAERPGEAAVA | SEQ ID NO. 91 |
| peptide 92 | GAQFSKTAAKG | SEQ ID NO. 92 |
| peptide 93 | AQFSKTAAKGE | SEQ ID NO. 93 |
| peptide 94 | QFSKTAAKGEA | SEQ ID NO. 94 |
| peptide 95 | FSKTAAKGEAA | SEQ ID NO. 95 |
| peptide 96 | SKTAAKGEAAA | SEQ ID NO. 96 |
| peptide 97 | KTAAKGEAAAE | SEQ ID NO. 97 |
| peptide 98 | TAAKGEAAAER | SEQ ID NO. 98 |
| peptide 99 | AAKGEAAAERP | SEQ ID NO. 99 |
| peptide 100 | AKGEAAAERPG | SEQ ID NO. 100 |
| peptide 101 | KGEAAAERPGE | SEQ ID NO. 101 |
| peptide 102 | GEAAAERPGEA | SEQ ID NO. 102 |
| peptide 103 | EAAAERPGEAA | SEQ ID NO. 103 |
| peptide 104 | AAAERPGEAAV | SEQ ID NO. 104 |
| peptide 105 | AAERPGEAAVA | SEQ ID NO. 105 |
| peptide 106 | GAQFSKTAAK | SEQ ID NO. 106 |
| peptide 107 | AQFSKTAAKG | SEQ ID NO. 107 |
| peptide 108 | QFSKTAAKGE | SEQ ID NO. 108 |
| peptide 109 | FSKTAAKGEA | SEQ ID NO. 109 |

TABLE IX-continued

Peptides and Amino Acid Sequences

| Peptide No. | Sequence | Seqence ID No. |
|---|---|---|
| peptide 110 | SKTAAKGEAA | SEQ ID NO. 110 |
| peptide 111 | KTAAKGEAAA | SEQ ID NO. 111 |
| peptide 112 | TAAKGEAAAE | SEQ ID NO. 112 |
| peptide 113 | AAKGEAAAER | SEQ ID NO. 113 |
| peptide 114 | AKGEAAAERP | SEQ ID NO. 114 |
| peptide 115 | KGEAAAERPG | SEQ ID NO. 115 |
| peptide 116 | GEAAAERPGE | SEQ ID NO. 116 |
| peptide 117 | EAAAERPGEA | SEQ ID NO. 117 |
| peptide 118 | AAAERPGEAA | SEQ ID NO. 118 |
| peptide 119 | AAERPGEAAV | SEQ ID NO. 119 |
| peptide 120 | AERPGEAAVA | SEQ ID NO. 120 |
| peptide 121 | GAQFSKTAA | SEQ ID NO. 121 |
| peptide 122 | AQFSKTAAK | SEQ ID NO. 122 |
| peptide 123 | QFSKTAAKG | SEQ ID NO. 123 |
| peptide 124 | FSKTAAKGE | SEQ ID NO. 124 |
| peptide 125 | SKTAAKGEA | SEQ ID NO. 125 |
| peptide 126 | KTAAKGEAA | SEQ ID NO. 126 |
| peptide 127 | TAAKGEAAA | SEQ ID NO. 127 |
| peptide 128 | AAKGEAAAE | SEQ ID NO. 128 |
| peptide 129 | AKGEAAAER | SEQ ID NO. 129 |
| peptide 130 | KGEAAAERP | SEQ ID NO. 130 |
| peptide 131 | GEAAAERPG | SEQ ID NO. 131 |
| peptide 132 | EAAAERPGE | SEQ ID NO. 132 |
| peptide 133 | AAAERPGEA | SEQ ID NO. 133 |
| peptide 134 | AAERPGEAA | SEQ ID NO. 134 |
| peptide 135 | AERPGEAAV | SEQ ID NO. 135 |
| peptide 136 | ERPGEAAVA | SEQ ID NO. 136 |
| peptide 137 | GAQFSKTA | SEQ ID NO. 137 |
| peptide 138 | AQFSKTAA | SEQ ID NO. 138 |
| peptide 139 | QFSKTAAK | SEQ ID NO. 139 |
| peptide 140 | FSKTAAKG | SEQ ID NO. 140 |
| peptide 141 | SKTAAKGE | SEQ ID NO. 141 |
| peptide 142 | KTAAKGEA | SEQ ID NO. 142 |
| peptide 143 | TAAKGEAA | SEQ ID NO. 143 |
| peptide 144 | AAKGEAAA | SEQ ID NO. 144 |
| peptide 145 | AKGEAAAE | SEQ ID NO. 145 |
| peptide 146 | KGEAAAER | SEQ ID NO. 146 |
| peptide 147 | GEAAAERP | SEQ ID NO. 147 |
| peptide 148 | EAAAERPG | SEQ ID NO. 148 |
| peptide 149 | AAAERPGE | SEQ ID NO. 149 |
| peptide 150 | AAERPGEA | SEQ ID NO. 150 |
| peptide 151 | AERPGEAA | SEQ ID NO. 151 |
| peptide 152 | ERPGEAAV | SEQ ID NO. 152 |
| peptide 153 | RPGEAAVA | SEQ ID NO. 153 |
| peptide 154 | GAQFSKT | SEQ ID NO. 154 |
| peptide 155 | AQFSKTA | SEQ ID NO. 155 |
| peptide 156 | QFSKTAA | SEQ ID NO. 156 |
| peptide 157 | FSKTAAK | SEQ ID NO. 157 |
| peptide 158 | SKTAAKG | SEQ ID NO. 158 |
| peptide 159 | KTAAKGE | SEQ ID NO. 159 |
| peptide 160 | TAAKGEA | SEQ ID NO. 160 |
| peptide 161 | AAKGEAA | SEQ ID NO. 161 |
| peptide 162 | AKGEAAA | SEQ ID NO. 162 |
| peptide 163 | KGEAAAE | SEQ ID NO. 163 |
| peptide 164 | GEAAAER | SEQ ID NO. 164 |
| peptide 165 | EAAAERP | SEQ ID NO. 165 |
| peptide 166 | AAAERPG | SEQ ID NO. 166 |
| peptide 167 | AAERPGE | SEQ ID NO. 167 |
| peptide 168 | AERPGEA | SEQ ID NO. 168 |
| peptide 169 | ERPGEAA | SEQ ID NO. 169 |
| peptide 170 | RPGEAAV | SEQ ID NO. 170 |
| peptide 171 | PGEAAVA | SEQ ID NO. 171 |
| peptide 172 | GAQFSK | SEQ ID NO. 172 |
| peptide 173 | AQFSKT | SEQ ID NO. 173 |
| peptide 174 | QFSKTA | SEQ ID NO. 174 |
| peptide 175 | FSKTAA | SEQ ID NO. 175 |
| peptide 176 | SKTAAK | SEQ ID NO. 176 |
| peptide 177 | KTAAKG | SEQ ID NO. 177 |
| peptide 178 | TAAKGE | SEQ ID NO. 178 |
| peptide 179 | AAKGEA | SEQ ID NO. 179 |
| peptide 180 | AKGEAA | SEQ ID NO. 180 |
| peptide 181 | KGEAAA | SEQ ID NO. 181 |
| peptide 182 | GEAAAE | SEQ ID NO. 182 |
| peptide 183 | EAAAER | SEQ ID NO. 183 |
| peptide 184 | AAAERP | SEQ ID NO. 184 |
| peptide 185 | AAERPG | SEQ ID NO. 185 |

TABLE IX-continued

Peptides and Amino Acid Sequences

| Peptide No. | Sequence | Seqence ID No. |
|---|---|---|
| peptide 186 | AERPGE | SEQ ID NO. 186 |
| peptide 187 | ERPGEA | SEQ ID NO. 187 |
| peptide 188 | RPGEAA | SEQ ID NO. 188 |
| peptide 189 | PGEAAV | SEQ ID NO. 189 |
| peptide 190 | GEAAVA | SEQ ID NO. 190 |
| peptide 191 | GAQFS | SEQ ID NO. 191 |
| peptide 192 | AQFSK | SEQ ID NO. 192 |
| peptide 193 | QFSKT | SEQ ID NO. 193 |
| peptide 194 | FSKTA | SEQ ID NO. 194 |
| peptide 195 | SKTAA | SEQ ID NO. 195 |
| peptide 196 | KTAAK | SEQ ID NO. 196 |
| peptide 197 | TAAKG | SEQ ID NO. 197 |
| peptide 198 | AAKGE | SEQ ID NO. 198 |
| peptide 199 | AKGEA | SEQ ID NO. 199 |
| peptide 200 | KGEAA | SEQ ID NO. 200 |
| peptide 201 | GEAAA | SEQ ID NO. 201 |
| peptide 202 | EAAAE | SEQ ID NO. 202 |
| peptide 203 | AAAER | SEQ ID NO. 203 |
| peptide 204 | AAERP | SEQ ID NO. 204 |
| peptide 205 | AERPG | SEQ ID NO. 205 |
| peptide 206 | ERPGE | SEQ ID NO. 206 |
| peptide 207 | RPGEA | SEQ ID NO. 207 |
| peptide 208 | PGEAA | SEQ ID NO. 208 |
| peptide 209 | GEAAV | SEQ ID NO. 209 |
| peptide 210 | EAAVA | SEQ ID NO. 210 |
| peptide 211 | GAQF | SEQ ID NO. 211 |
| peptide 212 | AQFS | SEQ ID NO. 212 |
| peptide 213 | QFSK | SEQ ID NO. 213 |
| peptide 214 | FSKT | SEQ ID NO. 214 |
| peptide 215 | SKTA | SEQ ID NO. 215 |
| peptide 216 | KTAA | SEQ ID NO. 216 |
| peptide 217 | TAAK | SEQ ID NO. 217 |
| peptide 218 | AAKG | SEQ ID NO. 218 |
| peptide 219 | AKGE | SEQ ID NO. 219 |
| peptide 220 | KGEA | SEQ ID NO. 220 |
| peptide 221 | GEAA | SEQ ID NO. 221 |
| peptide 222 | EAAA | SEQ ID NO. 222 |
| peptide 223 | AAAE | SEQ ID NO. 223 |
| peptide 224 | AAER | SEQ ID NO. 224 |
| peptide 225 | AERP | SEQ ID NO. 225 |
| peptide 226 | ERPG | SEQ ID NO. 226 |
| peptide 227 | RPGE | SEQ ID NO. 227 |
| peptide 228 | PGEA | SEQ ID NO. 228 |
| peptide 229 | GEAA | SEQ ID NO. 229 |
| peptide 230 | EAAV | SEQ ID NO. 230 |
| peptide 231 | AAVA | SEQ ID NO. 231 |
| peptide 232 | GTAPAAEGAGAEVKRASAEAKQAF | SEQ ID NO. 232 |
| peptide 233 | GKQFSKTAAKGE | SEQ ID NO. 233 |
| peptide 234 | GAQFSKTKAKGE | SEQ ID NO. 234 |
| peptide 235 | GKQFSKTKAKGE | SEQ ID NO. 235 |
| peptide 236 | GAQASKTAAK | SEQ ID NO. 236 |
| peptide 237 | GAQASKTAAKGE | SEQ ID NO. 237 |
| peptide 238 | GAEFSKTAAKGE | SEQ ID NO. 238 |
| peptide 239 | GAQFSKTAAAGE | SEQ ID NO. 239 |
| peptide 240 | GAQFSKTAAKAE | SEQ ID NO. 240 |
| peptide 241 | GAQFSKTAAKGA | SEQ ID NO. 241 |
| peptide 242 | AAQFSKTAAK | SEQ ID NO. 242 |
| peptide 243 | GAAFSKTAAK | SEQ ID NO. 243 |
| peptide 244 | GAQFAKTAAK | SEQ ID NO. 244 |
| peptide 245 | GAQFSATAAK | SEQ ID NO. 245 |
| peptide 246 | KAATKSFQAG | SEQ ID NO. 246 |
| peptide 247 | GAQFSKAAAK | SEQ ID NO. 247 |
| peptide 248 | GAQFSKTAAA | SEQ ID NO. 248 |
| peptide 249 | GAQFSATAAA | SEQ ID NO. 249 |
| peptide 250 | GAQASKTA | SEQ ID NO. 250 |
| peptide 251 | AAGE | SEQ ID NO. 251 |
| peptide 252 | GKASQFAKTA | SEQ ID NO. 252 |

While the invention has been described in detail and with reference to specific embodiments thereof, it will be apparent to one skilled in the art that various changes and modifications can be made without departing from the spirit and scope of the invention.

What is claimed is:

1. An N-terminal- and/or C-terminal-chemically modified peptide, which peptide consists of an amino acid sequence consisting of
a contiguous 4 to 6 amino acid segment of a reference sequence, GAQFSKTAAKGEAAAERPGEAAVA (SEQ ID NO:1), wherein the amino acid segment is selected from the group consisting of SEQ ID NO: 176 to SEQ ID NO: 180, SEQ ID NO: 196 to SEQ ID NO: 199, SEQ ID NO: 217 and SEQ ID NO: 219;
wherein
(i) the C-terminal amino acid of said chemically modified peptide is chemically modified and the N-terminal amino acid of the peptide is alkylated or acylated at the N-terminal amino group;
or
(ii) the C-terminal amino acid of said chemically modified peptide is not chemically modified and the N-terminal amino acid of the peptide is alkylated or acylated at the N-terminal amino group and is not myristoylated;
with the proviso that said chemically modified peptide contains no more than 6 amino acids; and
wherein said chemically modified peptide has a mucin hypersecretion-inhibiting effect when administered to a mammal in a mucin hypersecretion-inhibiting amount.

2. The modified peptide of claim 1, wherein the amino acid sequence of the peptide includes the contiguous residues AKGE (SEQ ID NO: 219) of the reference sequence.

3. The modified peptide of claim 1, wherein the N-terminal amino acid of the peptide is acetylated at the N-terminal amino group.

4. The modified peptide of claim 1, wherein said peptide is acetyl-PEPTIDE 179, acetyl-PEPTIDE 219, or acetyl-PEPTIDE 219-NH$_2$.

5. The modified peptide of claim 1, wherein the amino acid sequence is selected from the group consisting of the amino acid sequence of SEQ ID NO: 178 to SEQ ID NO: 180, SEQ ID NO: 198, SEQ ID NO: 199 and SEQ ID NO: 219.

6. The modified peptide of claim 1, wherein the N-terminal amino acid is alkylated at the N-terminal amine with a C1 to C24 aliphatic alkyl group, a linear 2-(C1 to C24 aliphatic alkyl)oxyethyl group, or an omega-methoxy-poly(ethyleneoxy)$_n$-ethyl group, where n is from 0 to 10.

7. The modified peptide of claim 1, wherein the N-terminal amino acid is acylated at the N-terminal amine with a-trifluoroacetic acid, benzoic acid, or a $C_1$ to $C_{24}$ aliphatic carboxylic acid.

8. The modified peptide of claim 1, wherein the C-terminal amino acid of the peptide is amidated or esterified at the C-terminal carboxyl group.

9. The modified peptide of claim 1, wherein the C-terminal amino acid is amidated at the C-terminal carboxyl group with ammonia, a C1 to C24 aliphatic alkyl amine, a hydroxyl-substituted C2 to C24 aliphatic alkyl amine, a linear 2-(C1 to C24 aliphatic alkyl)oxyethylamine group, or an omega-methoxy-poly(ethyleneoxy)$_n$-ethylamine group, where n is from 0 to 10.

10. The modified peptide of claim 1, wherein the C-terminal amino acid is esterified at the C-terminal carboxyl group with a C1 to C24 aliphatic alkyl alcohol or a 2-(omega-methoxy-poly(ethyleneoxy)$_n$)-ethanol group, where n is from of 0 to 10.

11. The modified peptide of claim 1, wherein the modified peptide exhibits at least one of the properties of (a) greater mucin hypersecretion-inhibiting effect on a mammal than a peptide with reference sequence, GAQFSKTAAKGEAAAERPGEAAVA (SEQ ID NO:1), wherein the N-terminal amino acid of the reference sequence is myristoylated, when administered to said mammal at equal concentrations or (b) greater aqueous solubility than SEQ ID NO:1, wherein the N-terminal amino acid of the reference sequence is myristoylated, at equal concentrations in the same liquid.

12. A pharmaceutical composition comprising the peptide of claim 1 and a pharmaceutically acceptable carrier.

13. The pharmaceutical composition of claim 12, wherein said composition is suitable for pulmonary administration.

14. An N-terminal- and/or C-terminal-chemically modified peptide, which peptide consists of an amino acid sequence selected from
 a contiguous 4 to 6 amino acid segment of a reference sequence, GAQFSKTAAKGEAAAERPGEAAVA (SEQ ID NO:1), which amino acid segment is selected from the group consisting of SEQ ID NO: 176 to SEQ ID NO: 180, SEQ ID NO: 196 to SEQ ID NO: 199, SEQ ID NO: 217 and SEQ ID NO: 219;
 wherein
 (i) the C-terminal amino acid of said chemically modified peptide is chemically modified and the N-terminal amino acid of the peptide is alkylated or acylated at the N-terminal amino group; or
 (ii) the C-terminal amino acid of said chemically modified peptide is chemically modified and the N-terminal amino acid of the peptide is not chemically modified; or
 (iii) the N-terminal amino acid of said chemically modified peptide is alkylated or acylated at the N-terminal amino group and is not myristoylated and the C-terminal amino acid of the peptide is not chemically modified;
 with the proviso that said chemically modified peptide contains no more than 6 amino acids; and
 wherein said chemically modified peptide has a mucin hypersecretion-inhibiting effect when administered to a mammal in a mucin hypersecretion-inhibiting amount.

15. The modified peptide of claim 14, wherein the N-terminal amino acid of the peptide is myristoylated at the N-terminal amino group.

16. The modified peptide of claim 14, wherein the C-terminal amino acid of the peptide is amidated or esterified at the C-terminal carboxyl group.

17. A pharmaceutical composition comprising the peptide of claim 14 and a pharmaceutically acceptable carrier.

18. The pharmaceutical composition of claim 17, wherein said composition is suitable for pulmonary administration.

* * * * *

SEQUENCE LISTING

<160> NUMBER OF SEQ ID NOS: 252

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 1

Gly Ala Gln Phe Ser Lys Thr Ala Ala Lys Gly Glu Ala Ala Ala Glu
1               5                   10                  15

Arg Pro Gly Glu Ala Ala Val Ala
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 2

Gly Ala Gln Phe Ser Lys Thr Ala Ala Lys Gly Glu Ala Ala Ala Glu
1               5                   10                  15

Arg Pro Gly Glu Ala Ala Val
            20

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 3

Ala Gln Phe Ser Lys Thr Ala Ala Lys Gly Glu Ala Ala Ala Glu Arg
1               5                   10                  15

Pro Gly Glu Ala Ala Val Ala
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 4

Gly Ala Gln Phe Ser Lys Thr Ala Ala Lys Gly Glu Ala Ala Ala Glu
1               5                   10                  15

Arg Pro Gly Glu Ala Ala
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 5

Ala Gln Phe Ser Lys Thr Ala Ala Lys Gly Glu Ala Ala Ala Glu Arg
1               5                   10                  15

Pro Gly Glu Ala Ala Val
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 6

Gln Phe Ser Lys Thr Ala Ala Lys Gly Glu Ala Ala Ala Glu Arg Pro
1               5                   10                  15

Gly Glu Ala Ala Val Ala
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 7

Gly Ala Gln Phe Ser Lys Thr Ala Ala Lys Gly Glu Ala Ala Ala Glu
1               5                   10                  15

Arg Pro Gly Glu Ala
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 8

Ala Gln Phe Ser Lys Thr Ala Ala Lys Gly Glu Ala Ala Ala Glu Arg
1               5                   10                  15

Pro Gly Glu Ala Ala
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 9

Gln Phe Ser Lys Thr Ala Ala Lys Gly Glu Ala Ala Ala Glu Arg Pro
1               5                   10                  15

Gly Glu Ala Ala Val
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 10

Phe Ser Lys Thr Ala Ala Lys Gly Glu Ala Ala Ala Glu Arg Pro Gly
1               5                   10                  15

Glu Ala Ala Val Ala
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 11

Gly Ala Gln Phe Ser Lys Thr Ala Ala Lys Gly Glu Ala Ala Ala Glu
1               5                   10                  15

Arg Pro Gly Glu
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 12

Ala Gln Phe Ser Lys Thr Ala Ala Lys Gly Glu Ala Ala Ala Glu Arg
1               5                   10                  15

-continued

Pro Gly Glu Ala
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 13

Gln Phe Ser Lys Thr Ala Ala Lys Gly Glu Ala Ala Ala Glu Arg Pro
1               5                   10                  15

Gly Glu Ala Ala
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 14

Phe Ser Lys Thr Ala Ala Lys Gly Glu Ala Ala Ala Glu Arg Pro Gly
1               5                   10                  15

Glu Ala Ala Val
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 15

Ser Lys Thr Ala Ala Lys Gly Glu Ala Ala Ala Glu Arg Pro Gly Glu
1               5                   10                  15

Ala Ala Val Ala
            20

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 16

Gly Ala Gln Phe Ser Lys Thr Ala Ala Lys Gly Glu Ala Ala Ala Glu
1               5                   10                  15

Arg Pro Gly

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 17

Ala Gln Phe Ser Lys Thr Ala Ala Lys Gly Glu Ala Ala Ala Glu Arg
1               5                   10                  15

Pro Gly Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 18

Gln Phe Ser Lys Thr Ala Ala Lys Gly Glu Ala Ala Ala Glu Arg Pro
1               5                   10                  15

Gly Glu Ala

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 19

Phe Ser Lys Thr Ala Ala Lys Gly Glu Ala Ala Ala Glu Arg Pro Gly
1               5                   10                  15

Glu Ala Ala

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 20

Ser Lys Thr Ala Ala Lys Gly Glu Ala Ala Ala Glu Arg Pro Gly Glu
1               5                   10                  15

Ala Ala Val

```
<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 21

Lys Thr Ala Ala Lys Gly Glu Ala Ala Ala Glu Arg Pro Gly Glu Ala
1               5                   10                  15

Ala Val Ala

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 22

Gly Ala Gln Phe Ser Lys Thr Ala Ala Lys Gly Glu Ala Ala Ala Glu
1               5                   10                  15

Arg Pro

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 23

Ala Gln Phe Ser Lys Thr Ala Ala Lys Gly Glu Ala Ala Ala Glu Arg
1               5                   10                  15

Pro Gly

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 24

Gln Phe Ser Lys Thr Ala Ala Lys Gly Glu Ala Ala Ala Glu Arg Pro
1               5                   10                  15

Gly Glu

<210> SEQ ID NO 25
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 25

Phe Ser Lys Thr Ala Ala Lys Gly Glu Ala Ala Ala Glu Arg Pro Gly
1               5                   10                  15

Glu Ala

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 26

Ser Lys Thr Ala Ala Lys Gly Glu Ala Ala Ala Glu Arg Pro Gly Glu
1               5                   10                  15

Ala Ala

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 27

Lys Thr Ala Ala Lys Gly Glu Ala Ala Ala Glu Arg Pro Gly Glu Ala
1               5                   10                  15

Ala Val

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 28

Thr Ala Ala Lys Gly Glu Ala Ala Ala Glu Arg Pro Gly Glu Ala Ala
1               5                   10                  15

Val Ala

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

<223> OTHER INFORMATION: Peptide may or may not be C-term and/or N-term
      modified

<400> SEQUENCE: 29

Gly Ala Gln Phe Ser Lys Thr Ala Ala Lys Gly Glu Ala Ala Ala Glu
1               5                   10                  15
Arg

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 30

Ala Gln Phe Ser Lys Thr Ala Ala Lys Gly Glu Ala Ala Ala Glu Arg
1               5                   10                  15
Pro

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 31

Gln Phe Ser Lys Thr Ala Ala Lys Gly Glu Ala Ala Ala Glu Arg Pro
1               5                   10                  15
Gly

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 32

Phe Ser Lys Thr Ala Ala Lys Gly Glu Ala Ala Ala Glu Arg Pro Gly
1               5                   10                  15
Glu

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 33

```
Ser Lys Thr Ala Ala Lys Gly Glu Ala Ala Ala Glu Arg Pro Gly Glu
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 34

Lys Thr Ala Ala Lys Gly Glu Ala Ala Ala Glu Arg Pro Gly Glu Ala
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 35

Thr Ala Ala Lys Gly Glu Ala Ala Ala Glu Arg Pro Gly Glu Ala Ala
1               5                   10                  15

Val

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 36

Ala Ala Lys Gly Glu Ala Ala Ala Glu Arg Pro Gly Glu Ala Ala Val
1               5                   10                  15

Ala

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 37

Gly Ala Gln Phe Ser Lys Thr Ala Ala Lys Gly Glu Ala Ala Ala Glu
1               5                   10                  15
```

```
<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 38

Ala Gln Phe Ser Lys Thr Ala Ala Lys Gly Glu Ala Ala Ala Glu Arg
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 39

Gln Phe Ser Lys Thr Ala Ala Lys Gly Glu Ala Ala Ala Glu Arg Pro
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 40

Phe Ser Lys Thr Ala Ala Lys Gly Glu Ala Ala Ala Glu Arg Pro Gly
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 41

Ser Lys Thr Ala Ala Lys Gly Glu Ala Ala Ala Glu Arg Pro Gly Glu
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified
```

```
<400> SEQUENCE: 42

Lys Thr Ala Ala Lys Gly Glu Ala Ala Ala Glu Arg Pro Gly Glu Ala
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 43

Thr Ala Ala Lys Gly Glu Ala Ala Ala Glu Arg Pro Gly Glu Ala Ala
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 44

Ala Ala Lys Gly Glu Ala Ala Ala Glu Arg Pro Gly Glu Ala Ala Val
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 45

Ala Lys Gly Glu Ala Ala Ala Glu Arg Pro Gly Glu Ala Ala Val Ala
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 46

Gly Ala Gln Phe Ser Lys Thr Ala Ala Lys Gly Glu Ala Ala Ala
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued peptide
<220> FEATURE:
<223> OTHER INFORMATION: Peptide may or may not be C-term and/or N-term
      modified

<400> SEQUENCE: 47

Ala Gln Phe Ser Lys Thr Ala Ala Lys Gly Glu Ala Ala Ala Glu
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 48

Gln Phe Ser Lys Thr Ala Ala Lys Gly Glu Ala Ala Ala Glu Arg
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 49

Phe Ser Lys Thr Ala Ala Lys Gly Glu Ala Ala Ala Glu Arg Pro
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 50

Ser Lys Thr Ala Ala Lys Gly Glu Ala Ala Ala Glu Arg Pro Gly
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 51

Lys Thr Ala Ala Lys Gly Glu Ala Ala Ala Glu Arg Pro Gly Glu
1               5                   10                  15

<210> SEQ ID NO 52

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 52

Thr Ala Ala Lys Gly Glu Ala Ala Ala Glu Arg Pro Gly Glu Ala
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 53

Ala Ala Lys Gly Glu Ala Ala Ala Glu Arg Pro Gly Glu Ala Ala
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 54

Ala Lys Gly Glu Ala Ala Ala Glu Arg Pro Gly Glu Ala Ala Val
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 55

Lys Gly Glu Ala Ala Ala Glu Arg Pro Gly Glu Ala Ala Val Ala
1               5                   10                  15

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 56
```

```
Gly Ala Gln Phe Ser Lys Thr Ala Ala Lys Gly Glu Ala Ala
1               5                   10
```

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 57

```
Ala Gln Phe Ser Lys Thr Ala Ala Lys Gly Glu Ala Ala Ala
1               5                   10
```

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 58

```
Gln Phe Ser Lys Thr Ala Ala Lys Gly Glu Ala Ala Ala Glu
1               5                   10
```

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 59

```
Phe Ser Lys Thr Ala Ala Lys Gly Glu Ala Ala Ala Glu Arg
1               5                   10
```

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 60

```
Ser Lys Thr Ala Ala Lys Gly Glu Ala Ala Ala Glu Arg Pro
1               5                   10
```

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: Peptide may or may not be C-term and/or N-term
      modified

<400> SEQUENCE: 61

Lys Thr Ala Ala Lys Gly Glu Ala Ala Ala Glu Arg Pro Gly
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 62

Thr Ala Ala Lys Gly Glu Ala Ala Ala Glu Arg Pro Gly Glu
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 63

Ala Ala Lys Gly Glu Ala Ala Ala Glu Arg Pro Gly Glu Ala
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 64

Ala Lys Gly Glu Ala Ala Ala Glu Arg Pro Gly Glu Ala Ala
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 65

Lys Gly Glu Ala Ala Ala Glu Arg Pro Gly Glu Ala Ala Val
1               5                   10

<210> SEQ ID NO 66
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 66

Gly Glu Ala Ala Ala Glu Arg Pro Gly Glu Ala Ala Val Ala
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 67

Gly Ala Gln Phe Ser Lys Thr Ala Ala Lys Gly Glu Ala
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 68

Ala Gln Phe Ser Lys Thr Ala Ala Lys Gly Glu Ala Ala
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 69

Gln Phe Ser Lys Thr Ala Ala Lys Gly Glu Ala Ala Ala
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 70

Phe Ser Lys Thr Ala Ala Lys Gly Glu Ala Ala Ala Glu
1               5                   10
```

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 71

Ser Lys Thr Ala Ala Lys Gly Glu Ala Ala Ala Glu Arg
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 72

Lys Thr Ala Ala Lys Gly Glu Ala Ala Ala Glu Arg Pro
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 73

Thr Ala Ala Lys Gly Glu Ala Ala Ala Glu Arg Pro Gly
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 74

Ala Ala Lys Gly Glu Ala Ala Ala Glu Arg Pro Gly Glu
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

```
<400> SEQUENCE: 75

Ala Lys Gly Glu Ala Ala Ala Glu Arg Pro Gly Glu Ala
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 76

Lys Gly Glu Ala Ala Ala Glu Arg Pro Gly Glu Ala Ala
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 77

Gly Glu Ala Ala Ala Glu Arg Pro Gly Glu Ala Ala Val
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 78

Glu Ala Ala Ala Glu Arg Pro Gly Glu Ala Ala Val Ala
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 79

Gly Ala Gln Phe Ser Lys Thr Ala Ala Lys Gly Glu
1               5                   10

<210> SEQ ID NO 80
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 80

Ala Gln Phe Ser Lys Thr Ala Ala Lys Gly Glu Ala
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 81

Gln Phe Ser Lys Thr Ala Ala Lys Gly Glu Ala Ala
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 82

Phe Ser Lys Thr Ala Ala Lys Gly Glu Ala Ala Ala
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 83

Ser Lys Thr Ala Ala Lys Gly Glu Ala Ala Ala Glu
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 84

Lys Thr Ala Ala Lys Gly Glu Ala Ala Ala Glu Arg
1               5                   10
```

```
<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 85

Thr Ala Ala Lys Gly Glu Ala Ala Ala Glu Arg Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 86

Ala Ala Lys Gly Glu Ala Ala Ala Glu Arg Pro Gly
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 87

Ala Lys Gly Glu Ala Ala Ala Glu Arg Pro Gly Glu
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 88

Lys Gly Glu Ala Ala Ala Glu Arg Pro Gly Glu Ala
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 89
```

```
Gly Glu Ala Ala Ala Glu Arg Pro Gly Glu Ala Ala
1               5                   10
```

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 90

```
Glu Ala Ala Ala Glu Arg Pro Gly Glu Ala Ala Val
1               5                   10
```

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 91

```
Ala Ala Ala Glu Arg Pro Gly Glu Ala Ala Val Ala
1               5                   10
```

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 92

```
Gly Ala Gln Phe Ser Lys Thr Ala Ala Lys Gly
1               5                   10
```

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 93

```
Ala Gln Phe Ser Lys Thr Ala Ala Lys Gly Glu
1               5                   10
```

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: Peptide may or may not be C-term and/or N-term
      modified

<400> SEQUENCE: 94

Gln Phe Ser Lys Thr Ala Ala Lys Gly Glu Ala
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 95

Phe Ser Lys Thr Ala Ala Lys Gly Glu Ala Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 96

Ser Lys Thr Ala Ala Lys Gly Glu Ala Ala Ala
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 97

Lys Thr Ala Ala Lys Gly Glu Ala Ala Ala Glu
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 98

Thr Ala Ala Lys Gly Glu Ala Ala Ala Glu Arg
1               5                   10

<210> SEQ ID NO 99
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 99

Ala Ala Lys Gly Glu Ala Ala Ala Glu Arg Pro
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 100

Ala Lys Gly Glu Ala Ala Ala Glu Arg Pro Gly
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 101

Lys Gly Glu Ala Ala Ala Glu Arg Pro Gly Glu
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 102

Gly Glu Ala Ala Ala Glu Arg Pro Gly Glu Ala
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 103

Glu Ala Ala Ala Glu Arg Pro Gly Glu Ala Ala
```

```
<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 104

Ala Ala Ala Glu Arg Pro Gly Glu Ala Ala Val
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 105

Ala Ala Glu Arg Pro Gly Glu Ala Ala Val Ala
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 106

Gly Ala Gln Phe Ser Lys Thr Ala Ala Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 107

Ala Gln Phe Ser Lys Thr Ala Ala Lys Gly
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
``` modified

<400> SEQUENCE: 108

Gln Phe Ser Lys Thr Ala Ala Lys Gly Glu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 109

Phe Ser Lys Thr Ala Ala Lys Gly Glu Ala
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 110

Ser Lys Thr Ala Ala Lys Gly Glu Ala Ala
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 111

Lys Thr Ala Ala Lys Gly Glu Ala Ala Ala
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 112

Thr Ala Ala Lys Gly Glu Ala Ala Ala Glu
1               5                   10

<210> SEQ ID NO 113
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 113

Ala Ala Lys Gly Glu Ala Ala Ala Glu Arg
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 114

Ala Lys Gly Glu Ala Ala Ala Glu Arg Pro
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 115

Lys Gly Glu Ala Ala Ala Glu Arg Pro Gly
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 116

Gly Glu Ala Ala Ala Glu Arg Pro Gly Glu
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 117

Glu Ala Ala Ala Glu Arg Pro Gly Glu Ala
1               5                   10
```

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: Peptide may or may not be C-term and/or N-term
    modified

<400> SEQUENCE: 118

Ala Ala Ala Glu Arg Pro Gly Glu Ala Ala
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: Peptide may or may not be C-term and/or N-term
    modified

<400> SEQUENCE: 119

Ala Ala Glu Arg Pro Gly Glu Ala Ala Val
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: Peptide may or may not be C-term and/or N-term
    modified

<400> SEQUENCE: 120

Ala Glu Arg Pro Gly Glu Ala Ala Val Ala
1               5                   10

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: Peptide may or may not be C-term and/or N-term
    modified

<400> SEQUENCE: 121

Gly Ala Gln Phe Ser Lys Thr Ala Ala
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: Peptide may or may not be C-term and/or N-term
    modified

```
<400> SEQUENCE: 122

Ala Gln Phe Ser Lys Thr Ala Ala Lys
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 123

Gln Phe Ser Lys Thr Ala Ala Lys Gly
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 124

Phe Ser Lys Thr Ala Ala Lys Gly Glu
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 125

Ser Lys Thr Ala Ala Lys Gly Glu Ala
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 126

Lys Thr Ala Ala Lys Gly Glu Ala Ala
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                      peptide
<220> FEATURE:
<223> OTHER INFORMATION: Peptide may or may not be C-term and/or N-term
      modified

<400> SEQUENCE: 127

Thr Ala Ala Lys Gly Glu Ala Ala Ala
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 128

Ala Ala Lys Gly Glu Ala Ala Ala Glu
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 129

Ala Lys Gly Glu Ala Ala Ala Glu Arg
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 130

Lys Gly Glu Ala Ala Ala Glu Arg Pro
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 131

Gly Glu Ala Ala Ala Glu Arg Pro Gly
1               5

<210> SEQ ID NO 132
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 132

Glu Ala Ala Ala Glu Arg Pro Gly Glu
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 133

Ala Ala Ala Glu Arg Pro Gly Glu Ala
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 134

Ala Ala Glu Arg Pro Gly Glu Ala Ala
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 135

Ala Glu Arg Pro Gly Glu Ala Ala Val
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 136
```

```
Glu Arg Pro Gly Glu Ala Ala Val Ala
1               5
```

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 137

```
Gly Ala Gln Phe Ser Lys Thr Ala
1               5
```

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 138

```
Ala Gln Phe Ser Lys Thr Ala Ala
1               5
```

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 139

```
Gln Phe Ser Lys Thr Ala Ala Lys
1               5
```

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 140

```
Phe Ser Lys Thr Ala Ala Lys Gly
1               5
```

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Peptide may or may not be C-term and/or N-term
      modified

<400> SEQUENCE: 141

Ser Lys Thr Ala Ala Lys Gly Glu
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 142

Lys Thr Ala Ala Lys Gly Glu Ala
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 143

Thr Ala Ala Lys Gly Glu Ala Ala
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 144

Ala Ala Lys Gly Glu Ala Ala Ala
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 145

Ala Lys Gly Glu Ala Ala Ala Glu
1               5

<210> SEQ ID NO 146
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 146

Lys Gly Glu Ala Ala Ala Glu Arg
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 147

Gly Glu Ala Ala Ala Glu Arg Pro
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 148

Glu Ala Ala Ala Glu Arg Pro Gly
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 149

Ala Ala Ala Glu Arg Pro Gly Glu
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 150

Ala Ala Glu Arg Pro Gly Glu Ala
1               5
```

```
<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 151

Ala Glu Arg Pro Gly Glu Ala Ala
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 152

Glu Arg Pro Gly Glu Ala Ala Val
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 153

Arg Pro Gly Glu Ala Ala Val Ala
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 154

Gly Ala Gln Phe Ser Lys Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified
```

```
<400> SEQUENCE: 155

Ala Gln Phe Ser Lys Thr Ala
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 156

Gln Phe Ser Lys Thr Ala Ala
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 157

Phe Ser Lys Thr Ala Ala Lys
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 158

Ser Lys Thr Ala Ala Lys Gly
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 159

Lys Thr Ala Ala Lys Gly Glu
1               5

<210> SEQ ID NO 160
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 160

Thr Ala Ala Lys Gly Glu Ala
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 161

Ala Ala Lys Gly Glu Ala Ala
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 162

Ala Lys Gly Glu Ala Ala Ala
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 163

Lys Gly Glu Ala Ala Ala Glu
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 164

Gly Glu Ala Ala Ala Glu Arg
1               5
```

```
<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 165

Glu Ala Ala Ala Glu Arg Pro
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 166

Ala Ala Ala Glu Arg Pro Gly
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 167

Ala Ala Glu Arg Pro Gly Glu
1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 168

Ala Glu Arg Pro Gly Glu Ala
1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 169
```

```
Glu Arg Pro Gly Glu Ala Ala
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 170

Arg Pro Gly Glu Ala Ala Val
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 171

Pro Gly Glu Ala Ala Val Ala
1               5

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 172

Gly Ala Gln Phe Ser Lys
1               5

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 173

Ala Gln Phe Ser Lys Thr
1               5

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Peptide may or may not be C-term and/or N-term
      modified

<400> SEQUENCE: 174

Gln Phe Ser Lys Thr Ala
1               5

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 175

Phe Ser Lys Thr Ala Ala
1               5

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 176

Ser Lys Thr Ala Ala Lys
1               5

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 177

Lys Thr Ala Ala Lys Gly
1               5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 178

Thr Ala Ala Lys Gly Glu
1               5

<210> SEQ ID NO 179
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 179

Ala Ala Lys Gly Glu Ala
1               5

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 180

Ala Lys Gly Glu Ala Ala
1               5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 181

Lys Gly Glu Ala Ala Ala
1               5

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 182

Gly Glu Ala Ala Ala Glu
1               5

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 183

Glu Ala Ala Ala Glu Arg
```

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 184

Ala Ala Ala Glu Arg Pro
1               5

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 185

Ala Ala Glu Arg Pro Gly
1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 186

Ala Glu Arg Pro Gly Glu
1               5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 187

Glu Arg Pro Gly Glu Ala
1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term

```
                       modified

<400> SEQUENCE: 188

Arg Pro Gly Glu Ala Ala
1               5

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 189

Pro Gly Glu Ala Ala Val
1               5

<210> SEQ ID NO 190
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 190

Gly Glu Ala Ala Val Ala
1               5

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 191

Gly Ala Gln Phe Ser
1               5

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 192

Ala Gln Phe Ser Lys
1               5

<210> SEQ ID NO 193
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 193

Gln Phe Ser Lys Thr
1               5

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 194

Phe Ser Lys Thr Ala
1               5

<210> SEQ ID NO 195
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 195

Ser Lys Thr Ala Ala
1               5

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 196

Lys Thr Ala Ala Lys
1               5

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 197

Thr Ala Ala Lys Gly
1               5
```

```
<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 198

Ala Ala Lys Gly Glu
1               5

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 199

Ala Lys Gly Glu Ala
1               5

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 200

Lys Gly Glu Ala Ala
1               5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 201

Gly Glu Ala Ala Ala
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified
```

```
<400> SEQUENCE: 202

Glu Ala Ala Ala Glu
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 203

Ala Ala Ala Glu Arg
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 204

Ala Ala Glu Arg Pro
1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 205

Ala Glu Arg Pro Gly
1               5

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 206

Glu Arg Pro Gly Glu
1               5

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: Peptide may or may not be C-term and/or N-term
      modified

<400> SEQUENCE: 207

Arg Pro Gly Glu Ala
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 208

Pro Gly Glu Ala Ala
1               5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 209

Gly Glu Ala Ala Val
1               5

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 210

Glu Ala Ala Val Ala
1               5

<210> SEQ ID NO 211
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 211

Gly Ala Gln Phe
1

<210> SEQ ID NO 212
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 212

Ala Gln Phe Ser
1

<210> SEQ ID NO 213
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 213

Gln Phe Ser Lys
1

<210> SEQ ID NO 214
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 214

Phe Ser Lys Thr
1

<210> SEQ ID NO 215
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 215

Ser Lys Thr Ala
1

<210> SEQ ID NO 216
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 216
```

```
Lys Thr Ala Ala
1

<210> SEQ ID NO 217
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 217

Thr Ala Ala Lys
1

<210> SEQ ID NO 218
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 218

Ala Ala Lys Gly
1

<210> SEQ ID NO 219
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 219

Ala Lys Gly Glu
1

<210> SEQ ID NO 220
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 220

Lys Gly Glu Ala
1

<210> SEQ ID NO 221
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: Peptide may or may not be C-term and/or N-term
      modified

<400> SEQUENCE: 221

Gly Glu Ala Ala
1

<210> SEQ ID NO 222
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 222

Glu Ala Ala Ala
1

<210> SEQ ID NO 223
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 223

Ala Ala Ala Glu
1

<210> SEQ ID NO 224
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 224

Ala Ala Glu Arg
1

<210> SEQ ID NO 225
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 225

Ala Glu Arg Pro
1

<210> SEQ ID NO 226
<211> LENGTH: 4
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 226

Glu Arg Pro Gly
1

<210> SEQ ID NO 227
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 227

Arg Pro Gly Glu
1

<210> SEQ ID NO 228
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 228

Pro Gly Glu Ala
1

<210> SEQ ID NO 229
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 229

Gly Glu Ala Ala
1

<210> SEQ ID NO 230
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 230

Glu Ala Ala Val
1
```

```
<210> SEQ ID NO 231
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 231

Ala Ala Val Ala
1

<210> SEQ ID NO 232
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 232

Gly Thr Ala Pro Ala Ala Glu Gly Ala Gly Ala Glu Val Lys Arg Ala
1               5                   10                  15

Ser Ala Glu Ala Lys Gln Ala Phe
            20

<210> SEQ ID NO 233
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 233

Gly Lys Gln Phe Ser Lys Thr Ala Ala Lys Gly Glu
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 234

Gly Ala Gln Phe Ser Lys Thr Lys Ala Lys Gly Glu
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Peptide may or may not be C-term and/or N-term
      modified

<400> SEQUENCE: 235

Gly Lys Gln Phe Ser Lys Thr Lys Ala Lys Gly Glu
1               5                   10

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 236

Gly Ala Gln Ala Ser Lys Thr Ala Ala Lys
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 237

Gly Ala Gln Ala Ser Lys Thr Ala Ala Lys Gly Glu
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 238

Gly Ala Glu Phe Ser Lys Thr Ala Ala Lys Gly Glu
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 239

Gly Ala Gln Phe Ser Lys Thr Ala Ala Ala Gly Glu
1               5                   10

<210> SEQ ID NO 240
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 240

Gly Ala Gln Phe Ser Lys Thr Ala Ala Lys Ala Glu
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 241

Gly Ala Gln Phe Ser Lys Thr Ala Ala Lys Gly Ala
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 242

Ala Ala Gln Phe Ser Lys Thr Ala Ala Lys
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 243

Gly Ala Ala Phe Ser Lys Thr Ala Ala Lys
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 244

Gly Ala Gln Phe Ala Lys Thr Ala Ala Lys
```

```
<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 245

Gly Ala Gln Phe Ser Ala Thr Ala Ala Lys
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 246

Lys Ala Ala Thr Lys Ser Phe Gln Ala Gly
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 247

Gly Ala Gln Phe Ser Lys Ala Ala Ala Lys
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 248

Gly Ala Gln Phe Ser Lys Thr Ala Ala Ala
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
```

```
                              modified

<400> SEQUENCE: 249

Gly Ala Gln Phe Ser Ala Thr Ala Ala Ala
1               5                   10

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 250

Gly Ala Gln Ala Ser Lys Thr Ala
1               5

<210> SEQ ID NO 251
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 251

Ala Ala Gly Glu
1

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 252

Gly Lys Ala Ser Gln Phe Ala Lys Thr Ala
1               5                   10
```